(12) United States Patent
Panescu et al.

(10) Patent No.: US 11,304,771 B2
(45) Date of Patent: Apr. 19, 2022

(54) SURGICAL SYSTEM WITH HAPTIC FEEDBACK BASED UPON QUANTITATIVE THREE-DIMENSIONAL IMAGING

(71) Applicant: Intuitive Surgical Operations, Inc., Sunnyvale, CA (US)

(72) Inventors: Dorin Panescu, San Jose, CA (US); Daniel H. Jones, Alexandria, VA (US); Christopher B. Allenby, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 191 days.

(21) Appl. No.: 16/570,917

(22) Filed: Sep. 13, 2019

(65) Prior Publication Data

US 2020/0022769 A1    Jan. 23, 2020

Related U.S. Application Data

(63) Continuation of application No. 15/300,263, filed as application No. PCT/US2015/023214 on Mar. 28, 2015, now Pat. No. 10,555,788.
(Continued)

(51) Int. Cl.
*A61B 34/00* (2016.01)
*A61B 34/32* (2016.01)
(Continued)

(52) U.S. Cl.
CPC .......... *A61B 34/76* (2016.02); *A61B 1/00055* (2013.01); *A61B 1/04* (2013.01);
(Continued)

(58) Field of Classification Search
CPC ..... A61B 34/76; A61B 34/10; A61B 1/00055; A61B 1/04; A61B 1/06; A61B 34/30;
(Continued)

(56) References Cited

U.S. PATENT DOCUMENTS

| 5,394,455 A | 2/1995 | Roeck et al. |
| 5,704,897 A | 1/1998 | Truppe |

(Continued)

FOREIGN PATENT DOCUMENTS

| BR | PI0803388 A2 | 6/2010 |
| CA | 2859998 A1 | 5/2013 |

(Continued)

OTHER PUBLICATIONS

International Preliminary Report on Patentability for Application No. PCT/US2015/023210, dated Oct. 13, 2016, 12 pages.
(Continued)

*Primary Examiner* — Aaron B Fairchild
*Assistant Examiner* — Shankar Raj Ghimire
(74) *Attorney, Agent, or Firm* — Schwegman Lundberg & Woessner, P.A.

(57) ABSTRACT

A system is provided to provide haptic feedback during a medical procedure comprising: a quantitative three-dimensional (Q3D); a surgical instrument disposed to deform a tissue structure; a haptic user interface device configured to provide an indication of tissue structure deformation in response to information indicative of the measure of tissue structure deformation; and a processor configured to produce a Q3D model that includes information indicative of a measure of tissue structure deformation and to provide the information indicative of the measure of tissue structure deformation to the haptic user interface device.

20 Claims, 39 Drawing Sheets

Related U.S. Application Data

(60) Provisional application No. 62/096,522, filed on Dec. 23, 2014, provisional application No. 61/971,749, filed on Mar. 28, 2014.

(51) Int. Cl.

| | | |
|---|---|---|
| *A61B 1/00* | (2006.01) | |
| *A61B 34/30* | (2016.01) | |
| *A61B 34/37* | (2016.01) | |
| *A61B 34/20* | (2016.01) | |
| *A61B 34/10* | (2016.01) | |
| *A61B 1/04* | (2006.01) | |
| *A61B 1/06* | (2006.01) | |
| *A61B 17/00* | (2006.01) | |

(52) U.S. Cl.
CPC ............ *A61B 1/06* (2013.01); *A61B 34/10* (2016.02); *A61B 34/20* (2016.02); *A61B 34/30* (2016.02); *A61B 34/32* (2016.02); *A61B 34/37* (2016.02); *A61B 2017/00119* (2013.01); *A61B 2034/2059* (2016.02)

(58) Field of Classification Search
CPC ......... A61B 34/37; A61B 34/20; A61B 34/32; A61B 2034/2059; A61B 2017/00119
See application file for complete search history.

(56) References Cited

U.S. PATENT DOCUMENTS

| | | | |
|---|---|---|---|
| 5,735,277 | A | 4/1998 | Schuster |
| 5,749,362 | A | 5/1998 | Funda et al. |
| 5,833,633 | A * | 11/1998 | Sarvazyan ............ A61B 8/0833 600/587 |
| 6,320,979 | B1 * | 11/2001 | Melen ............... H04N 5/232123 382/154 |
| 6,346,940 | B1 | 2/2002 | Fukunaga |
| 6,491,702 | B2 | 12/2002 | Heilbrun et al. |
| 6,503,195 | B1 | 1/2003 | Keller et al. |
| 6,522,906 | B1 | 2/2003 | Salisbury, Jr. |
| 6,594,552 | B1 | 7/2003 | Nowlin et al. |
| 6,650,927 | B1 | 11/2003 | Keidar |
| 6,932,610 | B2 | 8/2005 | Ono et al. |
| 6,950,550 | B1 | 9/2005 | Sumi et al. |
| 7,728,868 | B2 | 6/2010 | Razzaque et al. |
| 7,907,166 | B2 | 3/2011 | Lamprecht et al. |
| 8,231,522 | B2 | 7/2012 | Endo et al. |
| 8,262,559 | B2 | 9/2012 | Krattiger |
| 8,334,900 | B2 | 12/2012 | Qu et al. |
| 8,514,491 | B2 | 8/2013 | Duparre |
| 8,561,473 | B2 | 10/2013 | Blumenkranz |
| 8,861,089 | B2 | 10/2014 | Duparre |
| 8,866,920 | B2 | 10/2014 | Venkataraman et al. |
| 8,902,321 | B2 | 12/2014 | Venkataraman et al. |
| 9,041,829 | B2 | 5/2015 | Venkataraman et al. |
| 9,060,142 | B2 | 6/2015 | Venkataraman et al. |
| 9,119,552 | B2 * | 9/2015 | Baumann ............... A61B 5/065 |
| 9,188,765 | B2 | 11/2015 | Venkataraman et al. |
| 9,235,898 | B2 | 1/2016 | Venkataraman et al. |
| 9,264,610 | B2 | 2/2016 | Duparre |
| 9,485,496 | B2 | 11/2016 | Venkataraman et al. |
| 10,052,157 | B2 | 8/2018 | Frimer et al. |
| 10,334,227 | B2 | 6/2019 | Panescu et al. |
| 10,350,009 | B2 | 7/2019 | Panescu et al. |
| 10,368,054 | B2 | 7/2019 | Panescu et al. |
| 10,555,788 | B2 | 2/2020 | Panescu et al. |
| 2001/0051761 | A1 | 12/2001 | Khadem |
| 2002/0022765 | A1 | 2/2002 | Belson |
| 2002/0049375 | A1 | 4/2002 | Strommer et al. |
| 2002/0054208 | A1 | 5/2002 | Goldstein et al. |
| 2003/0036714 | A1 * | 2/2003 | Kuth ..................... A61B 5/441 600/587 |
| 2003/0158477 | A1 | 8/2003 | Panescu |
| 2003/0181800 | A1 | 9/2003 | Bonutti |
| 2003/0220541 | A1 | 11/2003 | Salisbury et al. |
| 2005/0151839 | A1 | 7/2005 | Ito et al. |
| 2005/0182295 | A1 | 8/2005 | Soper et al. |
| 2005/0219205 | A1 | 10/2005 | Bailey et al. |
| 2005/0254720 | A1 | 11/2005 | Tan et al. |
| 2006/0183992 | A1 | 8/2006 | Kawashima et al. |
| 2006/0281971 | A1 | 12/2006 | Sauer et al. |
| 2007/0055128 | A1 | 3/2007 | Glossop et al. |
| 2007/0060792 | A1 | 3/2007 | Draxinger et al. |
| 2007/0083098 | A1 | 4/2007 | Stern et al. |
| 2007/0135803 | A1 | 6/2007 | Belson |
| 2007/0147707 | A1 | 6/2007 | Coste-Maniere et al. |
| 2007/0151391 | A1 | 7/2007 | Larkin et al. |
| 2007/0171369 | A1 | 7/2007 | Grundig |
| 2007/0236514 | A1 | 10/2007 | Agusanto et al. |
| 2007/0276501 | A1 | 11/2007 | Betz et al. |
| 2008/0004603 | A1 | 1/2008 | Larkin et al. |
| 2008/0009674 | A1 | 1/2008 | Yaron et al. |
| 2008/0058593 | A1 | 3/2008 | Gu et al. |
| 2008/0071140 | A1 | 3/2008 | Gattani et al. |
| 2008/0188716 | A1 | 8/2008 | Heckele et al. |
| 2008/0207997 | A1 | 8/2008 | Higgins et al. |
| 2009/0043161 | A1 | 2/2009 | Doi |
| 2009/0054910 | A1 | 2/2009 | Zheng et al. |
| 2009/0076476 | A1 * | 3/2009 | Barbagli ............ A61B 5/6885 604/500 |
| 2009/0088634 | A1 | 4/2009 | Zhao et al. |
| 2009/0088897 | A1 | 4/2009 | Zhao et al. |
| 2009/0133260 | A1 | 5/2009 | Durbin et al. |
| 2009/0157059 | A1 * | 6/2009 | Allen .................... A61B 34/25 606/1 |
| 2009/0157659 | A1 | 6/2009 | Allen et al. |
| 2009/0189749 | A1 * | 7/2009 | Salada .................. G06F 3/033 340/407.2 |
| 2009/0192524 | A1 | 7/2009 | Itkowitz et al. |
| 2009/0221908 | A1 | 9/2009 | Glossop et al. |
| 2009/0259102 | A1 | 10/2009 | Koninckx et al. |
| 2009/0306474 | A1 | 12/2009 | Wilson |
| 2009/0317727 | A1 | 12/2009 | Beck |
| 2010/0111389 | A1 | 5/2010 | Strobel et al. |
| 2010/0149183 | A1 | 6/2010 | Loewke et al. |
| 2010/0169815 | A1 | 7/2010 | Zhao et al. |
| 2010/0249506 | A1 | 9/2010 | Prisco |
| 2010/0274087 | A1 * | 10/2010 | Diolaiti ................. A61B 90/37 600/118 |
| 2010/0281370 | A1 | 11/2010 | Rohaly et al. |
| 2010/0312129 | A1 * | 12/2010 | Schecter ............. A61B 5/0031 600/508 |
| 2010/0312696 | A1 | 12/2010 | Guttman et al. |
| 2011/0032088 | A1 * | 2/2011 | Kim ...................... G06F 3/016 340/407.1 |
| 2011/0044521 | A1 | 2/2011 | Tewfik et al. |
| 2011/0122229 | A1 | 5/2011 | Cinquin et al. |
| 2011/0163946 | A1 * | 7/2011 | Tartz .................... G06F 3/016 345/156 |
| 2011/0193938 | A1 | 8/2011 | Oderwald et al. |
| 2011/0282143 | A1 | 11/2011 | Matsumoto |
| 2011/0282151 | A1 * | 11/2011 | Trovato ................ G06T 7/248 600/117 |
| 2012/0041345 | A1 * | 2/2012 | Rajamani ............. A61B 5/103 600/587 |
| 2012/0063644 | A1 * | 3/2012 | Popovic ............... A61B 34/20 382/103 |
| 2012/0101370 | A1 | 4/2012 | Razzaque et al. |
| 2012/0139828 | A1 * | 6/2012 | Lok ..................... G09B 23/28 345/156 |
| 2012/0155731 | A1 | 6/2012 | Weersink et al. |
| 2012/0182294 | A1 | 7/2012 | Cordon et al. |
| 2012/0190923 | A1 | 7/2012 | Kunz |
| 2012/0265062 | A1 | 10/2012 | Sliwa et al. |
| 2012/0289777 | A1 | 11/2012 | Chopra et al. |
| 2013/0035583 | A1 | 2/2013 | Park et al. |
| 2013/0038689 | A1 * | 2/2013 | McDowall ............ H04N 5/232 348/45 |
| 2013/0070060 | A1 | 3/2013 | Chatterjee et al. |
| 2013/0079620 | A1 | 3/2013 | Kuth et al. |
| 2013/0085329 | A1 | 4/2013 | Morrissette et al. |
| 2013/0197357 | A1 | 8/2013 | Green |

(56) References Cited

U.S. PATENT DOCUMENTS

| | | | |
|---|---|---|---|
| 2013/0202676 A1 | 8/2013 | Koob et al. | |
| 2013/0211244 A1 | 8/2013 | Nathaniel et al. | |
| 2013/0211418 A1 | 8/2013 | Lim et al. | |
| 2013/0230837 A1 | 9/2013 | Meglan et al. | |
| 2013/0250081 A1 | 9/2013 | Pandey | |
| 2013/0296872 A1 | 11/2013 | Davison et al. | |
| 2013/0321262 A1* | 12/2013 | Schecter | G06F 19/00 345/156 |
| 2014/0005684 A1* | 1/2014 | Kim | A61B 17/0469 606/130 |
| 2014/0039527 A1 | 2/2014 | Avelar et al. | |
| 2014/0071239 A1 | 3/2014 | Yokota et al. | |
| 2014/0163359 A1 | 6/2014 | Sholev et al. | |
| 2014/0194896 A1 | 7/2014 | Frimer et al. | |
| 2014/0253684 A1 | 9/2014 | Kumar et al. | |
| 2014/0276093 A1 | 9/2014 | Zeien et al. | |
| 2014/0336501 A1 | 11/2014 | Masumoto | |
| 2015/0011894 A1* | 1/2015 | Sarrafzadeh | G06T 7/586 600/476 |
| 2015/0025316 A1 | 1/2015 | Hasegawa et al. | |
| 2015/0031990 A1 | 1/2015 | Boctor et al. | |
| 2015/0049167 A1 | 2/2015 | Suzuki et al. | |
| 2015/0062299 A1* | 3/2015 | Brown | A61B 1/051 348/45 |
| 2015/0112237 A1 | 4/2015 | Amedi et al. | |
| 2015/0134095 A1 | 5/2015 | Hemani et al. | |
| 2015/0185849 A1* | 7/2015 | Levesque | G06F 3/011 340/636.1 |
| 2015/0209003 A1 | 7/2015 | Halmann et al. | |
| 2015/0230697 A1* | 8/2015 | Phee | A61B 1/05 600/106 |
| 2015/0230869 A1* | 8/2015 | Shim | A61B 34/37 606/130 |
| 2015/0271483 A1 | 9/2015 | Sun et al. | |
| 2015/0374210 A1 | 12/2015 | Durr et al. | |
| 2016/0151646 A1 | 6/2016 | Bonutti et al. | |
| 2017/0172662 A1 | 6/2017 | Panescu et al. | |
| 2017/0180704 A1 | 6/2017 | Panescu et al. | |
| 2017/0181798 A1 | 6/2017 | Panescu et al. | |
| 2017/0181808 A1 | 6/2017 | Panescu et al. | |
| 2017/0181809 A1 | 6/2017 | Panescu et al. | |
| 2017/0188011 A1 | 6/2017 | Panescu et al. | |
| 2017/0212723 A1 | 7/2017 | Atarot et al. | |
| 2019/0167354 A1 | 6/2019 | Heaney et al. | |

FOREIGN PATENT DOCUMENTS

| | | | |
|---|---|---|---|
| CN | 1788684 A | 6/2006 | |
| CN | 1874734 A | 12/2006 | |
| CN | 100998511 A | 7/2007 | |
| CN | 101053517 A | 10/2007 | |
| CN | 101065052 A | 10/2007 | |
| CN | 101090670 A | 12/2007 | |
| CN | 102046065 A | 5/2011 | |
| CN | 102595998 A | 7/2012 | |
| CN | 102625670 A | 8/2012 | |
| CN | 102636130 A | 8/2012 | |
| CN | 102711650 A | 10/2012 | |
| CN | 102781303 A | 11/2012 | |
| CN | 102908158 A | 2/2013 | |
| CN | 102933163 A | 2/2013 | |
| CN | 103108602 A | 5/2013 | |
| CN | 103269430 A | 8/2013 | |
| CN | 103315908 A | 9/2013 | |
| CN | 103356155 A | 10/2013 | |
| CN | 103596521 A | 2/2014 | |
| EP | 1382297 A1 | 1/2004 | |
| EP | 1577010 A2 | 9/2005 | |
| EP | 1710828 A2 | 10/2006 | |
| EP | 1826726 A1 | 8/2007 | |
| EP | 2043499 A1 | 4/2009 | |
| EP | 2245982 A1 * | 11/2010 | A61B 1/042 |
| EP | 2444006 A2 | 4/2012 | |
| EP | 2548495 A1 | 1/2013 | |
| EP | 2641561 A1 | 9/2013 | |
| JP | S6160087 A | 3/1986 | |
| JP | H04176429 A | 6/1992 | |
| JP | H04325147 A | 11/1992 | |
| JP | H0630896 A | 2/1994 | |
| JP | H06160087 A | 6/1994 | |
| JP | H07240945 A | 9/1995 | |
| JP | H0998985 A | 4/1997 | |
| JP | H11309 A | 1/1999 | |
| JP | 2000065532 A | 3/2000 | |
| JP | 2002027502 A | 3/2000 | |
| JP | 2000149017 A | 5/2000 | |
| JP | 2002171537 A | 6/2002 | |
| JP | 2003235785 A | 8/2003 | |
| JP | 2004358096 A | 12/2004 | |
| JP | 2005087468 A | 4/2005 | |
| JP | 2005091265 A | 4/2005 | |
| JP | 2006109939 A | 4/2006 | |
| JP | 2006305332 A | 11/2006 | |
| JP | 2009204991 A | 9/2009 | |
| JP | 2010085240 A | 4/2010 | |
| JP | 2011200515 A | 10/2011 | |
| JP | 2011528252 A | 11/2011 | |
| JP | 2012518517 A | 8/2012 | |
| JP | 2013031660 A | 2/2013 | |
| JP | 2013515959 A | 5/2013 | |
| JP | 2014000118 A | 1/2014 | |
| KR | 20020014751 A | 2/2002 | |
| KR | 20130015146 A | 2/2013 | |
| WO | WO-2006080076 A | 8/2006 | |
| WO | WO-2007047782 A | 4/2007 | |
| WO | WO-2010122145 A1 | 4/2007 | |
| WO | WO-2010147729 A1 | 12/2010 | |
| WO | WO-2012059253 A1 | 5/2012 | |
| WO | WO-2012136223 A1 | 10/2012 | |
| WO | WO-2012155152 A1 | 11/2012 | |
| WO | WO-2013027201 A2 | 2/2013 | |
| WO | WO-2013038403 A2 | 3/2013 | |
| WO | WO-2013073061 A1 | 5/2013 | |
| WO | WO-2013134782 A1 | 9/2013 | |
| WO | WO-2014002849 A1 | 1/2014 | |

OTHER PUBLICATIONS

International Preliminary Report on Patentability for Application No. PCT/US2015/023211, dated Oct. 13, 2016, 10 pages.
International Preliminary Report on Patentability for Application No. PCT/US2015/023212, dated Oct. 13, 2016, 7 pages.
International Preliminary Report on Patentability for Application No. PCT/US2015/023213, dated Oct. 13, 2016, 11 pages.
International Preliminary Report on Patentability for Application No. PCT/US2015/023214, dated Oct. 13, 2016, 7 pages.
International Preliminary Report on Patentability for Application No. PCT/US2015/023217, dated Oct. 13, 2016, 08 pages.
Kaczmarek K.A. et al., "Maximal Dynamic Range Electrotactile Stimulation Waveforms," IEEE Transactions on Biomedical Engineering, Jul. 1999, vol. 39 (7), pp. 701-715.
Schick, A et al., "3D Measuring in the Field of Endoscopy," Proceedings of the SPIE, vol. 8082, 2011, pp. 1-12.
Schmalz, C. et al., "An Endoscopic 3D Scanner Based on Structured Light," Medical Image Analysis, vol. 16 (5) Jul. 2012. pp. 1063-1072.
Agus M., et al., "Real-time Cataract Surgery Simulation for Training," In Eurographics Italian Chapter Conference, Eurographics Association, 2006, 5 pages.
Coelho M., et al., "Shape-Changing interfaces." Personal and Ubiquitous Computing, M. Coelho, J. Zigelbaum, MIT Media Lab, 75 Amherst St., E14-548H, Cambridge, MA, USA. Springer-Verlag, published online Jul. 29, 2010. vol. 15 (2), pp. 181-173.
Cotin S., et al., "Real-time Elastic Deformations of Soft Tissues for Surgery Simulation," IEEE Transactions on Visualization and Computer Graphics, 1999, vol. 5, pp. 62-73.
Culnat M., et al., "Pneumatic Balloon Actuators for Tactile Feedback in Robotic Surgery," Industrial Robot: An International Journal, 2008. vol. 35 (5), pp. 449-455.

(56) References Cited

OTHER PUBLICATIONS

Delingette H., "Simplex Meshes: A General Representation for 3D Shape Reconstruction." Technical Report 2214, INRIA, Mar. 1994, 59 pages.
Eltaib, M.E.H., et al., "Tactite Sensing Technology for Minimal Access Surgery—a Review." Mechatronics, Pergamon Press, Oxford, GB, vol. 13(10). Dec. 1, 2003 (Dec. 1, 2003), pp. 1163-1177, XP004448741, DOI: 10.1016/S0957-4158(03)00048-5.
Extended European Search Report for Aoplication No. 15769234.4, dated Oct. 17, 2017, 11 pages.
Extended European Search Report for Application No. EP1 5767964. 8, dated Apr. 24, 2018, 19 pages.
Extended European Search Report for Application No. EP15768409. 3, dated Feb. 26, 2018, 9 pages.
Extended European Search Report for Application No. EP15769289. 8, dated Dec. 12, 2017, 11 pages.
Extended European Search Report for Application No. EP16770100. 4, dated Feb. 16, 2018, 14 pages.
Extended European Search Report for Application No. EP16770259. 8, dated Feb. 21, 2018, 18 pages.
Follmer S., et al., "inFORM: Dynamic Physical Affordances and Constraints through Shape and Object Actuation," Proceedings of the 26th Annual ACM Symposium on UIST, ACM, 2013, New York, NY, USA, vol. 13, pp. 417-426.
Garcia O., et al., "Real-time 3D Modeling from Endoscope Image Sequences," ICRA 2009 Workshop—Advanced Sensing and Sensor Integration in Medical Robotics, May 13, 2009 (May 13, 2009), Retrieved from the Internet: URL: http://webdiis.unizar.es/~jcivera/papers/garcia_etal_icra09.pdf [retrieved on Oct. 5, 2017], 3 pages, XP055412801.
Hassanfiroozi A., et al., Liquid Crystal Lens Array for 3D Endoscope Application, in: Three-Dimensional Imaging, Visualization, and Display, Javidi B., et al., eds., Proceedings of SPIE, vol. 9117 91170E 1-7, 7 pages, [online], [retrieved Aug. 21, 2814]. Retrieved from the Internet: URL: http://proceedings.spiedigitallibrary.org/.
Howe, Robert D. et al., "Remote Palpation Technology." IEEE Engineering in Medicine and Biology, 1995. pp 318-323, vol. 14—Issue 3, IEEE.
International Search Report and Written Opinion for Application No. PCT/US16/23210, dated Jun. 29, 2015, 17 pages.
International Search Report and Written Opinion for Application No. PCT/US15/23211, dated Jul. 1, 2015, 13 pages.
International Search Report and Written Opinion for Application No. PCT/US15/23217, dated Jun. 29, 2015, 12 pages.
International Search Report and Written Opinion for Application No. PCT/US2015/023214, dated Jun. 29, 2015, 10 pages.
International Search Report and Written Opinion for Application No. PCT/US2015/23212, dated Jun. 30, 2015, 8 pages.
International Search Report and Written Opinion for Application No. PCT/US2015/23213, dated Jul. 14, 2015, 13 pages.
Iwata H., et al., "Project FEELEX: Adding Haptic Surface to Graphics," SIGGRAPH'01, 2001, pp. 469-476.
J. Montegnat and H. Delingette, "Volumetric Medical Images Segmentation Using Shape Constrained Deformable Models," Proceedings of CVRMed-MRCAS '97, Grenoble, France, J. Troccaz, E. Grimson, and R. Mosges, eds. Mar. 1997, pp. 13-22.
K. Chinzei and K. Miller, "Compression of Swine Brain Tissue; Experiment in Vitro," Journel of Mechanical Engineering Laboratory, Jul. 1996, vol. 50(4), pp. 106-115.
Killebrew J.H., et al., "A Dense Array Stimulator to Generate Arbitrary Spatia-Tempora Tactile Stimuli," Journal of Neuroscience Methods, 2007, vol. 161 (1), pp. 62-74.

Laks Raghupathi, Laurent Grisoni, Fran?ois Faure, Damien Marchal, Marie-Paule Cani, Christophe Chaillou, "An Intestinal Surgery Simulator: Real-Time Collision Processing and Visualization," IEEE Transactions on Visualization and Computer Graphics, vol. 10, No. 6, pp. 708-718. Nov./Dec., 2004.
Monserrat C., et al., "GeRTISS: A Generic Multi-model Surqery Simulator," Springer-Verlag Berlin Heidelberg, IS4TM 2003, LNCS 2673, 2003, pp. 59-66.
Moore M., et al., "Collision Detection and Response for Computer Animation," Computer Graphics, SIGGRAPH, 1988, vol. 22 (4), pp. 289-298.
Moy G., et al., "A Compliant Tactile Display for Teletaction." Proceedings of ICRA in Robotics and Automation, 2000, IEEE, vol. 4, 7 pages.
Office Action dated Sep. 1, 2017 for Chinese Application No. 201680024436.7 filed Mar. 28, 2015, 25 pages.
Office Action dated Jul. 4, 2018 for Chinese Application No. 201580024439.0 filed Mar. 28, 2015, 13 pages.
Okamura A.M., "Haptic Feedback in Robot-Assisted Minimally Invasive Surgery," Current Opinion in Urology, 2009. vol. 19 (1), pp. 102-107.
Oosten, J.V., "Understanding the View Matrix—3D Game Engine Programming 3D Game Engine Programming," Jul. 6, 2011 (Jul. 6, 2011), Retrieved from the Internet: URL: http://www.3dgep.com/understanding-the-view-matrix/ [retrieved on Oct. 14, 2014], 34 pages, XP055220667.
Ottermo M.V., et al., "Electromechanical Design of a Miniature Tactile Shape Display for Minimally Invasive Surgery," Proceedings of the First Joint Eurohaptics Conference and Symposium on Haptic Interlaces for Virtual Environment and Teleoperator Systems, IEEE, 2005, 2 pages.
Partial Supplementary European Search Report for Application No. 15767964.8. dated Dec. 13, 2017, 17 pages.
Partial Supplementary European Search Report for Application No. 15770100.4, dated Oct. 18, 2017, 17 pages.
Partial Supplementary European Search Report for Application No. EP15770259.8, dated Oct. 24, 2017, 20 pages.
Rasmussen M.K., et al., "Shape-Ghanging Interfaces: A Review of the Design Space and Open Research Questions," Proceedings of the SIGCHI Conference on Human Factors in Computing Systems on CHI, ACM, 2012, pp. 735-744.
Reiley, Carol E. et al., "Effects of visual force feedback on robot-assisted surgical task performance," Journal of Thoracic and Cardiovascular Surgery, Jan. 2008, vol. 35 (1), pp. 196-202.
Rigel, D. S., et al., "The Evolution of Melanoma Diagnosis: 25 Years Beyond the ABCDs." CA Cancer J Clin. Vol. 60 (5), Jul. 29, 2010 (Jul. 29, 2010), pp. 301-310, XP055384411, ISSN: 0007-9235, DOI: 10.3322/caac.20074.
Thormahlen T., et al., "Three-Dimensional Endoscopy." Falk Symposium, vol. 124, Jan. 1, 2002 (Jan. 1, 2002), 6 pages, XP055413139, ISBN: 978-0-7923-8774-9.
Vertut, Jean and Philipe Coiffet, Robot Technology: Teleportation and Robotics Evolution and Development, English translation, Prentice-Hall, Inc., Inglewood Cliffs, NJ, USA 1986, vol. 3A, 332 pages.
Wu C., "3D Reconstruction of Anatomical Structures from Endoscopic Images," CMU-R1-TR-10-04, Jan. 1, 2010 (Jan. 1, 2010), Retrieved from the Internet: URL:https://www.cs.cmu.edu/-ILIM/publications/PDFs/W-THESIS09.pdf [retrieved on Oct. 5, 2017], pp. 1-113, XP055412730.

\* cited by examiner

SURGICAL SYSTEM WITH HAPTIC FEEDBACK BASED UPON QUANTITATIVE THREE-DIMENSIONAL IMAGING

RELATED APPLICATIONS

This application is a continuation of and claims the benefit of priority under 35 U.S.C. § 120 to U.S. patent application Ser. No. 15/300,263, filed on Sep. 28, 2016, which is a U.S. National Stage Filing under 35 U.S.C. 371 from International Application No. PCT/US2015/023214, filed on Mar. 28, 2015, and published as WO 2015/149044 A1 on Oct. 1, 2015, which claims the benefit of priority to U.S. provisional patent application No. 61/971,749, filed on Mar. 28, 2014, and entitled "QUANTITATIVE THREE-DIMENSIONAL IMAGING OF SURGICAL SCENES"; and to U.S. provisional patent application No. 62/096,522, filed on Dec. 23, 2014, and entitled "SURGICAL SYSTEM WITH HAPTIC FEEDBACK BASED UPON QUANTITATIVE THREE-DIMENSIONAL IMAGING", each of which is incorporated herein by reference in its entirety.

FIELD

The invention relates in general to surgical endoscopy systems having associated image sensors, and more particularly, to determining three-dimensional coordinates of physical structures displayed in surgical images.

BACKGROUND

Quantitative three-dimensional (Q3D) vision provides numerical information about the actual physical (x, y, z) 3D coordinates of target points in a real world scene. With quantitative 3D vision, a person not only can obtain a three-dimensional perception of a real world scene, but also can obtain numerical information about physical dimensions of objects in the scene and physical distances between objects in the scene. In the past, some Q3D systems have been proposed that use time-of-flight related information or phase information to determine 3D information about a scene. Other Q3D systems have used structured light to determine 3D information about a scene.

The use of time-of-flight information is disclosed in U.S. Pat. No. 6,323,942, entitled, "CMOS-compatible three-dimensional image sensor IC", which discloses a three-dimensional imaging system that includes a two-dimensional array of pixel light sensing detectors fabricated on a common IC using CMOS fabrication techniques. Each detector has an associated high speed counter that accumulates clock pulses in number directly proportional to time-of-flight (TOF) for a system-emitted pulse to reflect from an object point and be detected by a pixel detector focused upon that point. The TOF data provides a direct digital measure of distance from the particular pixel to a point on the object reflecting the emitted light pulse. In a second embodiment, the counters and high speed clock circuits are eliminated, and instead each pixel detector is provided with a charge accumulator and an electronic shutter. The shutters are opened when a light pulse is emitted and closed thereafter such that each pixel detector accumulates charge as a function of return photon energy falling upon the associated pixel detector. The amount of accumulated charge provides a direct measure of round-trip TOF.

The use of time delay information is disclosed in U.S. Pat. No. 8,262,559, entitled, "Apparatus and method for endoscopic 3D data collection", which discloses a modulated measuring beam and a light-transmitting mechanism for conducting the measuring beam onto an area to be observed, where the light-transmitting mechanism includes an illuminating lens, in addition to a light-imaging mechanism for imaging a signal beam from the area to be observed at least onto a phase-sensitive image sensor. Time delays, which may correspond to differences in depth in the millimeter range, result in phase information that makes possible the production of an image that depicts depth and distance information.

The use of structured light to determine physical coordinates of objects in a visual image is disclosed in U.S. Pat. App. Pub. No. 2012/0190923, entitled "Endoscope"; and in C. Schmalz et al., "An endoscopic 3D scanner based on structured light", Medical Image Analysis, 16 (2012) 1063-1072. A triangulation method is used to measure the topography of a surface. Structured light in the form of projection rays, which may have a range of different color spectra, are incident upon and are reflected from a surface. The reflected rays are observed by a camera that is calibrated to use the reflected color spectra information to determine 3D coordinates of the surface. More specifically, the use of structured light typically involves shining a light pattern on a 3D surface, and determining physical distances based upon a deformation pattern of the light due to contours of the physical object.

An imager array camera has been built that includes a plurality of pixel arrays that can be used to compute scene depth information for pixels in the array. High resolution (HR) images are generated from multiple low resolution (LR) images. A reference viewpoint is selected and an HR image is generated as seen by that viewpoint. A parallax processing technique utilizes the effects of aliasing to determine pixel correspondences for non-reference images with respect to the reference image pixels. Fusion and superresolution are utilized to produce the HR image from the multiple LR images. See e.g., U.S. Pat. No. 8,514,491, entitled "Capturing and Processing Images using Monolithic Camera Array with Heterogeneous Imager"; U.S. Pat. App. Pub. No. 2013/0070060, entitled, "Systems and Methods for Determining Depth from multiple Views of a Scene that include Aliasing using Hypothesized Fusion"; and K. Venkataraman et al., "PiCam: An ultra-Thin high Performance Monolithic Camera Array".

FIG. 1 is an illustrative drawing showing details of a known imager sensor 180 in accordance with some embodiments. The image sensor 180 includes an arrangement of sensors 184. Each sensor in the arrangement includes a two dimensional arrangement of pixels having at least two pixels in each dimension. Each sensor includes a lens stack 186. Each lens stack 186 has a corresponding focal plane 188. Each lens stack 186 creates a separate optical channel that resolves an image onto a corresponding arrangement of pixels disposed in its corresponding focal 188 plane. The pixels act as light sensors, and each focal plane 188 with its multiple pixels acts as an image sensor. Each sensor with its focal plane 188 occupies a region of the sensor arrangement different from regions of the sensor arrangement occupied by other sensors and focal planes.

FIG. 2 is an illustrative drawing showing a simplified plan view of the known arrangement of sensors 184 of FIG. 1 that includes sensors labeled as sensors $S_{11}$ through $S_{33}$. The imager sensor arrangement 184 is fabricated on a semiconductor chip to include a plurality of sensors $S_{11}$ through $S_{33}$. Each of the sensors $S_{11}$ through $S_{33}$ includes a plurality of pixels (e.g., 0.32 megapixels) and is coupled to peripheral circuitry (not shown) that includes independent read-out control and pixel digitization. In some embodiments, the sensors $S_{11}$ through $S_{33}$ are arranged into a grid format as illustrated in FIG. 2. In other embodiments, the sensors are arranged in a non-grid format. For example, the sensors may be arranged in a circular pattern, zigzagged pattern, scattered pattern, or irregular pattern including sub-pixel offsets.

Each individual pixel of the sensors 184 of FIGS. 1-2 includes a microlens pixel stack. FIG. 3 is an illustrative drawing of a known microlens pixel stack of the sensors of FIGS. 1-2. The pixel stack 800 includes a microlens 802, which is positioned above an oxide layer 804. Typically beneath the oxide layer 804 there may be a color filter 806, which is disposed above a nitride layer 808, which is disposed above a second oxide layer 810, which sits atop a silicon layer 812 that includes the active area 814 (typically a photodiode) of the individual pixel. The primary role of the microlens 802 is to gather the light incident on its surface and to focus that light onto the small active area 814. The pixel aperture 816 is determined by the spread of the microlens.

Additional information concerning the above-described known imager sensor arrangement architecture is provided in U.S. Pat. No. 8,514,491 B2 (filed Nov. 22, 2010), and in U.S. Patent Application Pub. No. U.S. 2013/0070060 A1 (filed Sep. 19, 2012),

SUMMARY

In one aspect, a system is provided to provide haptic feedback during a medical procedure. A quantitative three-dimensional (Q3D) endoscope is disposed to image a scene within its field of view. A surgical instrument disposed within the field of view is operable to deform a tissue structure within the field of view. A haptic user interface device is configured to provide an indication of tissue structure deformation in response to information indicative of a measure of tissue structure deformation. One or more processors are configured to produce a Q3D model that includes information indicative of a measure of tissue structure deformation and to provide the information indicative of the measure of tissue structure deformation to the haptic user interface device.

In another aspect, a system is provided to provide haptic feedback during a medical procedure. A quantitative three-dimensional (Q3D) endoscope is disposed to image a scene within its field of view. A surgical instrument disposed within the field of view is operable to deform a tissue structure within the field of view. One or more processors are configured to produce a Q3D model that includes information indicative of a measure of tissue structure deformation. Based on measured tissue deformation and on knowledge of the tissue stiffness, the one or more processors compute or estimate the force exerted by the instrument onto tissue. The processor, or processors, provides the information indicative of the exerted force to a haptic user interface device.

In another aspect, a system is provided to provide haptic feedback during a medical procedure. A quantitative three-dimensional (Q3D) endoscope is disposed to image a scene within its field of view. An instrument disposed within the field of view is operable to palpate a tissue structure within the field of view. One or more processors are configured to produce a Q3D model that includes information indicative of a measure of tissue structure deformation during palpation. Based on measured tissue deformation and on knowledge of applied force the one or more processors compute or estimate a measure of tissue stiffness. The processor, or processors, provides the information indicative of the palpated tissue stiffness to a haptic user interface device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Figure 1:
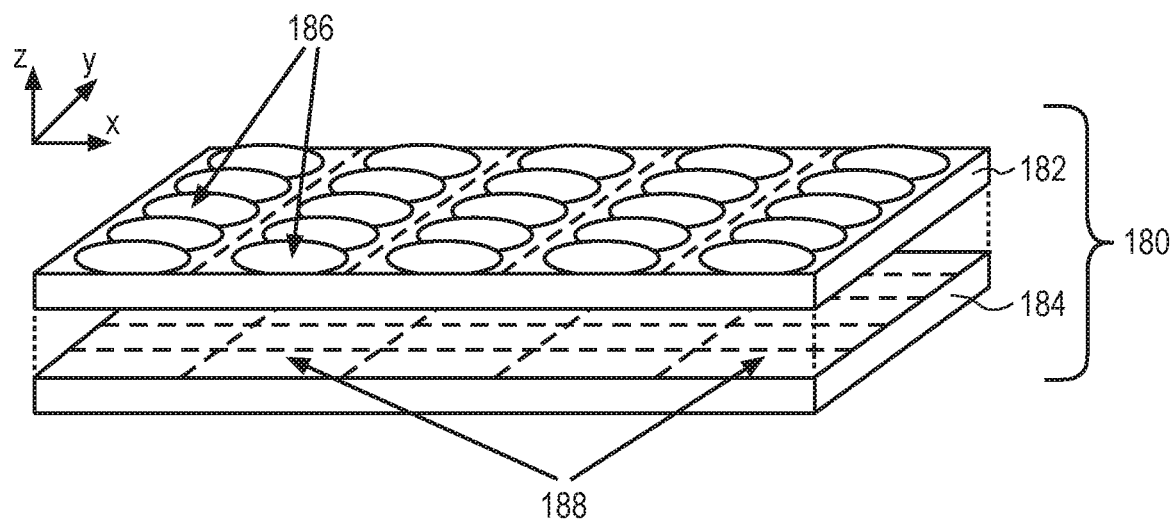
FIG. 1 is an illustrative drawing showing details of a known imager sensor array.
Figure 2:
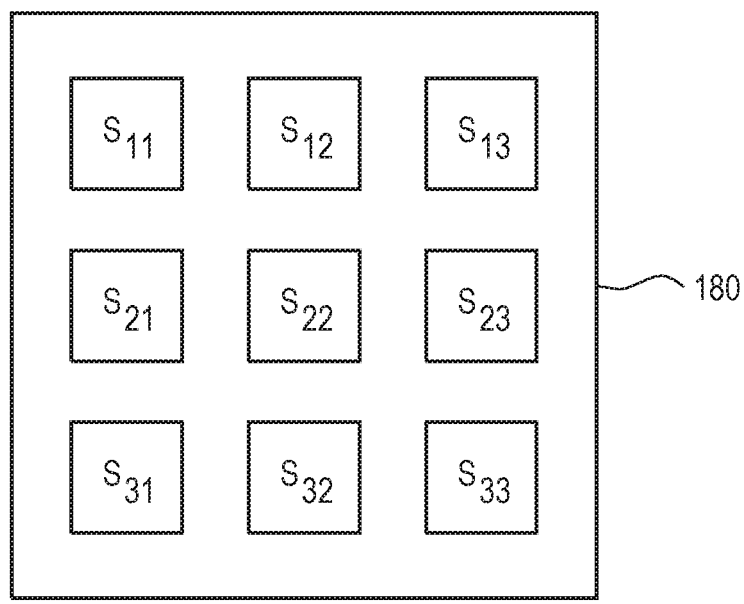
FIG. 2 is an illustrative drawing showing a simplified plan view of a known imager sensor array that includes multiple sensors.
Figure 3:
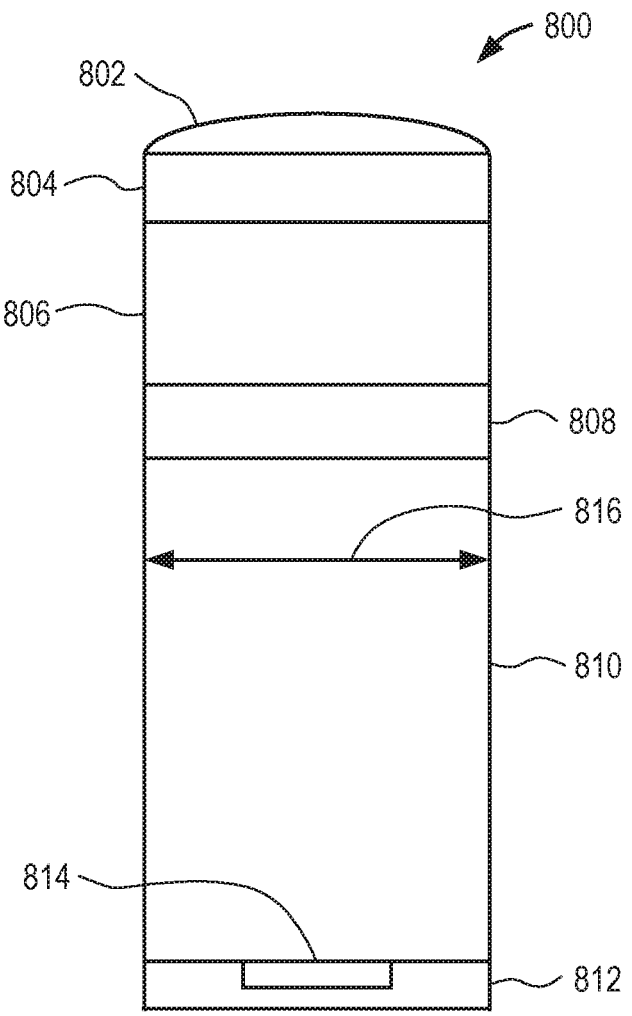
FIG. 3 is an illustrative drawing of a known microlens pixel stack.

The following description is presented to enable any person skilled in the art to create and use a surgical endoscopy system that captures quantitative three-dimensional (Q3D) information and that produces haptic feedback based upon the Q3D information. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Brief Overview

In accordance with some embodiments, an imager that includes that includes a sensor array is associated with an endoscope. The image sensor array includes multiple sensors, and each sensor includes an array of pixels. A portion of the endoscope is inserted into a human body cavity, and a target object in a field of view of the image sensor array is illuminated using a light source. A physical location and/or dimensions of the target object is determined based upon images of the target object projected onto individual sensors of the array.

Figure 4:
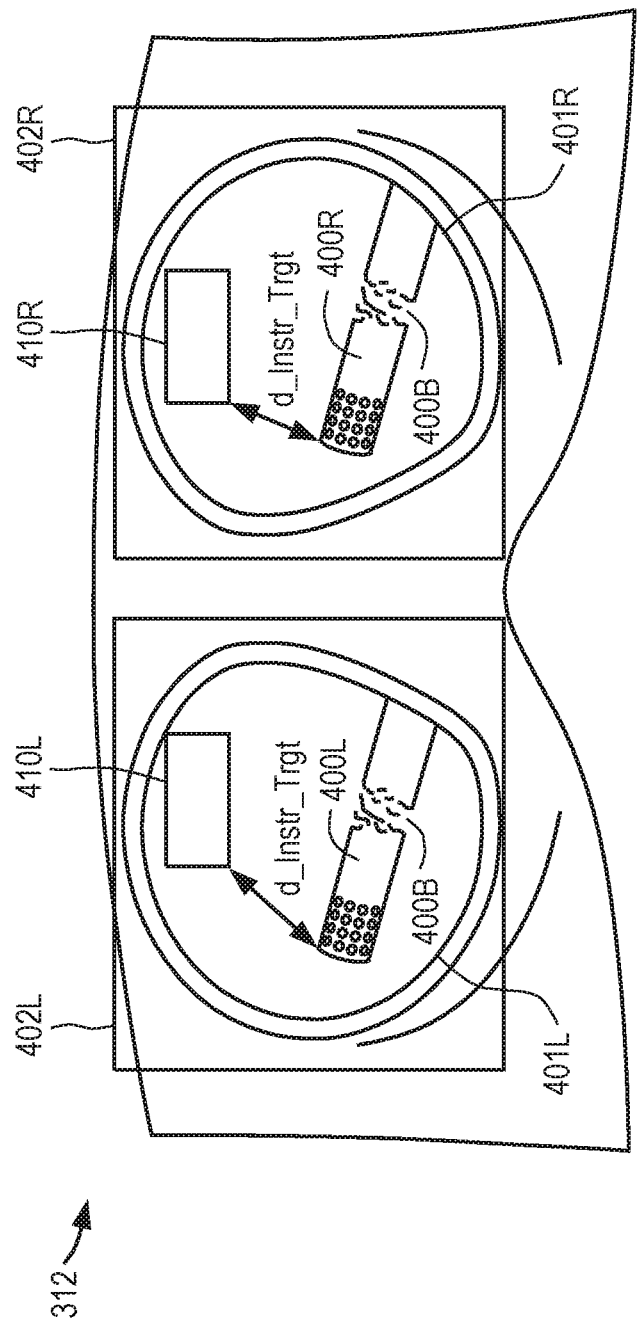
FIG. 4 is an illustrative drawing showing a perspective view of a surgical scene through a viewer in accordance with some embodiments.

FIG. 4 is an illustrative drawing showing a perspective view of a surgical scene through a viewer 312 in accordance with some embodiments. A viewing system having two viewing elements 401R, 401L can provide a good 3D viewing perspective. Numerical values representing physical dimension and/or location information for physical structures in the surgical scene are shown overlaid onto the surgical scene image. For example, a numerical distance value "d_Instr_Trgt" is shown displayed within the scene between instrument 400 and target 410.

Teleoperation Medical System

Teleoperation refers to operation of a machine at a distance. In a minimally invasive teleoperation medical system, a surgeon may use an endoscope that includes a camera to view a surgical site within a patient's body. Stereoscopic images have been captured, which allow the perception of depth during a surgical procedure. A camera system, which is mounted on an endoscope and which includes an imager sensor array, provides quantitative three-dimensional information plus color and illumination data that can be used to generate three-dimensional images in accordance with some embodiments.

Figure 5:
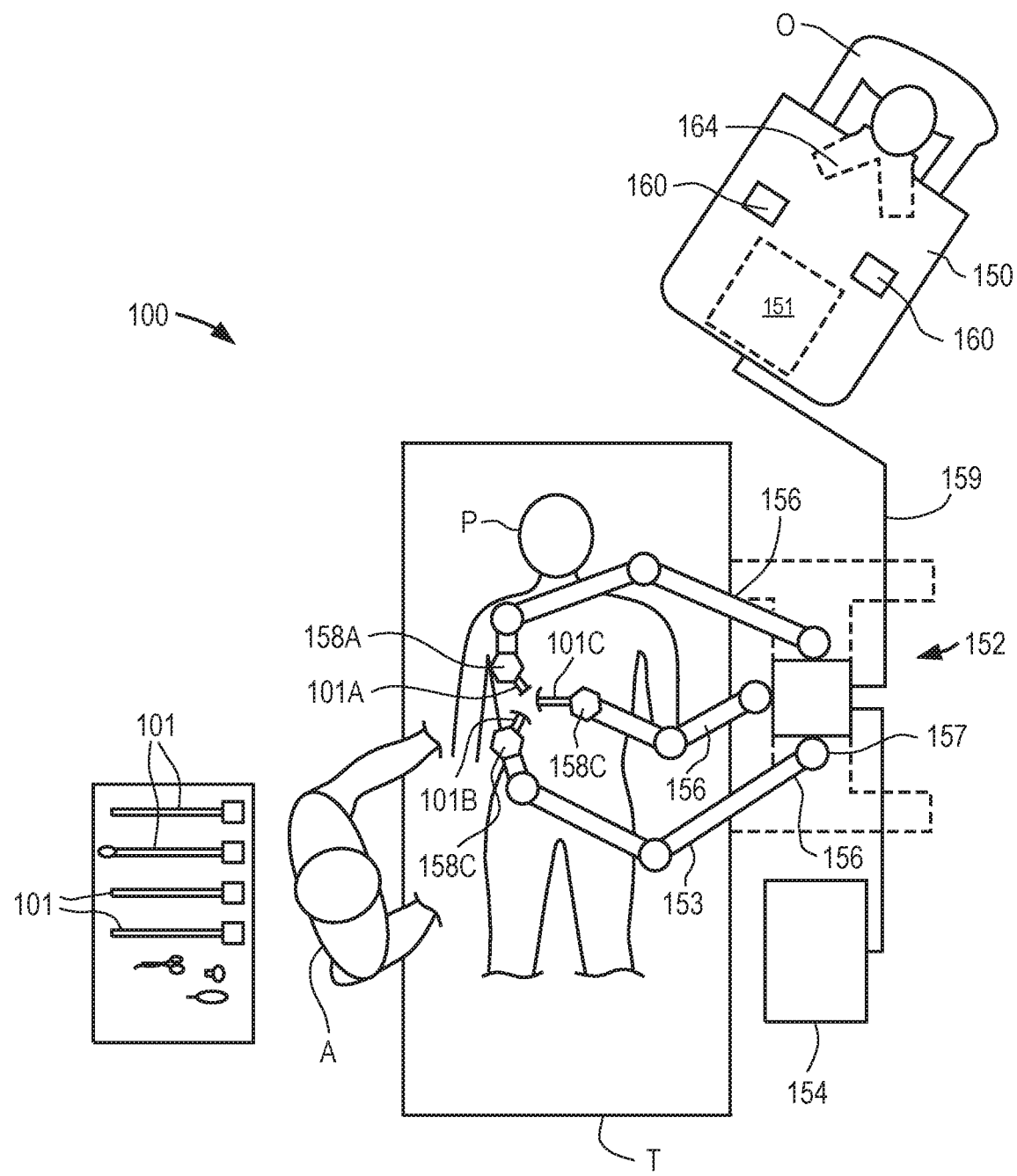
FIG. 5 is an illustrative block diagram of a teleoperation surgery system to perform minimally invasive surgical procedures using one or more mechanical arms in accordance with some embodiments.

FIG. 5 is an illustrative block diagram of a teleoperation surgery system 100 to perform minimally invasive surgical procedures using one or more mechanical arms 158 in accordance with some embodiments. Aspects of system 100 includes telerobotic and autonomously operating features. These mechanical arms often support an instrument. For instance, a mechanical surgical arm (e.g., the center mechanical surgical arm 158C) may be used to support an endoscope with a stereo or three-dimensional surgical image capture device 101C, such as an endoscope associated a Q3D image sensor array. The mechanical surgical arm 158C may include a sterile adapter, or a clamp, clip, screw, slot/groove, or other fastener mechanism to mechanically secure an endoscope that includes the image capture device 101C to the mechanical arm. Conversely, the endoscope with image capture device 101C may include physical contours and/or structures complementary to those of the mechanical surgical arm 158C so as to securely interfit with them.

A user or operator O (generally a surgeon) performs a minimally invasive surgical procedure on patient P by manipulating control input devices 160 at a master control console 150. The operator can view video frames of images of a surgical site inside a patient's body through a stereo display device 164, which includes the viewer 312 described above with reference to FIG. 4, A computer 151 of the console 150 directs movement of teleoperationally controlled endoscopic surgical instruments 101A-101C via control lines 159, effecting movement of the instruments using a patient-side system 152 (also referred to as a patient-side cart).

The patient-side system 152 includes one or more mechanical arms 158. Typically, the patient-side system 152 includes at least three mechanical surgical arms 158A-158C (generally referred to as mechanical surgical arms 158) supported by corresponding positioning set-up arms 156. The central mechanical surgical arm 158C may support an endoscopic camera 101C suitable for capture of Q3D information for images within a field of view of the camera. The mechanical surgical arms 158A and 158B to the left and right of center may support instruments 101A and 101B, respectively, which may manipulate tissue.

Figure 6:
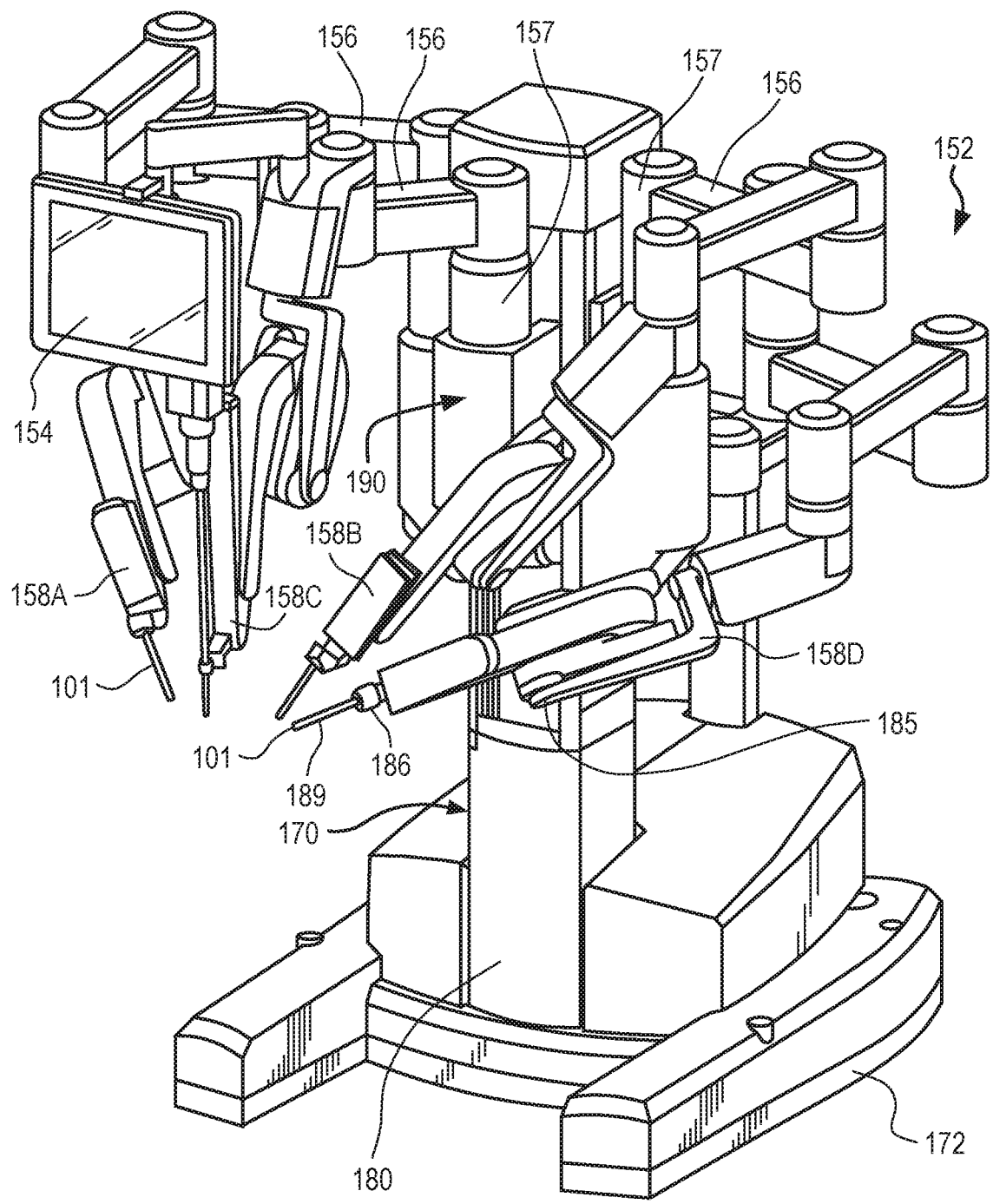
FIG. 6 is an illustrative perspective view of a patient-side system of the system of FIG. 5 in accordance with some embodiments.

FIG. 6 is an illustrative perspective view of the patient-side system 152 in accordance with some embodiments. The patient-side system 152 comprises a cart column 170 supported by a base 172. One or more mechanical insertion surgical arms/links 158 are respectively attached to one or more set-up arms 156 that are a part of the positioning portion of the patient-side system 152. Situated approximately at a central location on base 172, the cart column 170 includes a protective cover 180 that protects components of a counterbalance subsystem and a braking subsystem from contaminants.

Excluding a monitor arm 154, each mechanical surgical arm 158 is used to control instruments 101A-101C. Moreover, each mechanical surgical arm 158 is coupled to a set-up arm 156 that is in turn coupled to a carriage housing 190 in one embodiment of the invention. The one or more mechanical surgical arms 158 are each supported by their respective set-up arm 156, as is illustrated in FIG. 6.

The mechanical surgical arms 158A-158D may each include one or more displacement transducers, orientational sensors, and/or positional sensors 185 to generate raw uncorrected kinematics information to assist in initial acquisition by a tracking system and tracking of instruments. The instruments may also include a displacement transducer, a positional sensor, and/or orientation sensor 186 in some embodiments of the invention. Moreover, one or more instruments may include a marker 189 to assist in acquisition and tracking of the instruments.

Additional information about a teleoperation medical system is provided in U.S. Patent Application Pub. No. US 2012/0020547, (filed Sep. 30, 2011).

Endoscopic Imager System

Figure 7A:
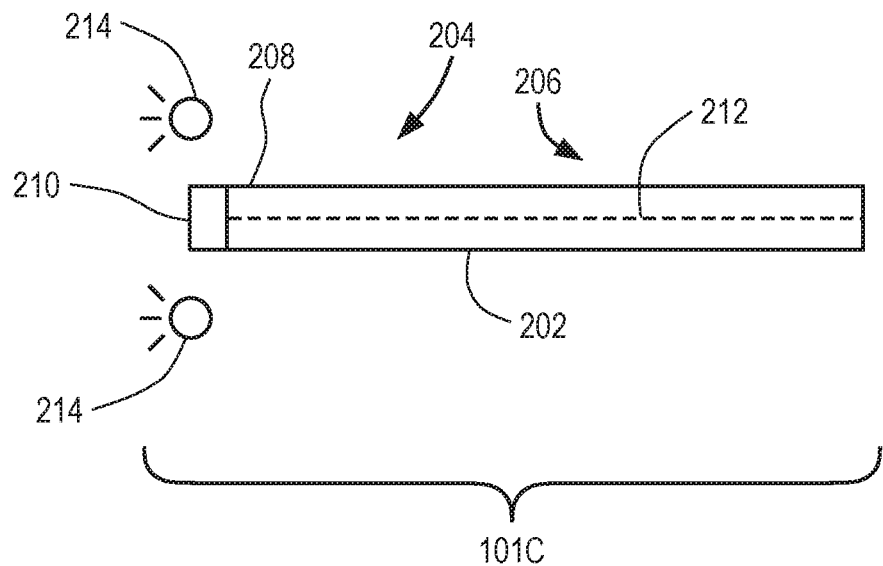
FIG. 7A is an illustrative drawing of a first image capture system in accordance with some embodiments.

FIG. 7A is an illustrative drawing of a first endoscope with a first image capture system 101C in accordance with some embodiments. The image capture system 101C includes an endoscope that includes elongated portion 202, which includes a first end portion 204 and a second end portion 206 and a tip portion 208 of the first end portion 204. The first end portion 204 is dimensioned to be inserted into a human body cavity. A sensor array 210, which includes multiple image sensors (not shown), is coupled at the tip portion 208 of the first end portion 204. In accordance with some embodiments, each sensor in the sensor array 210 includes an array of pixels. The elongated portion 202 has a length sufficient to position the tip portion 208 close enough to a target object within the body cavity so that the object can be imaged by the imager sensor array 210. In accordance with some embodiments, the second end portion 206 may include physical contours and/or structures (not shown), as generally described above, so as to securely interfit with a mechanical arm (not shown). The elongated portion 202 also includes one or more electronic signal paths 212 to electronically communicate information with the imager sensor array 210. A light source 214 is disposed to illuminate the object to be imaged. In accordance with some embodiments, the light source 214 can be unstructured light, white light, color filtered light, or light at some selected wavelength, for example. In accordance with some embodiments the light source 214 is located at tip 208, and in other embodiments it is optionally located separately from endoscope 101C.

Figure 7B:
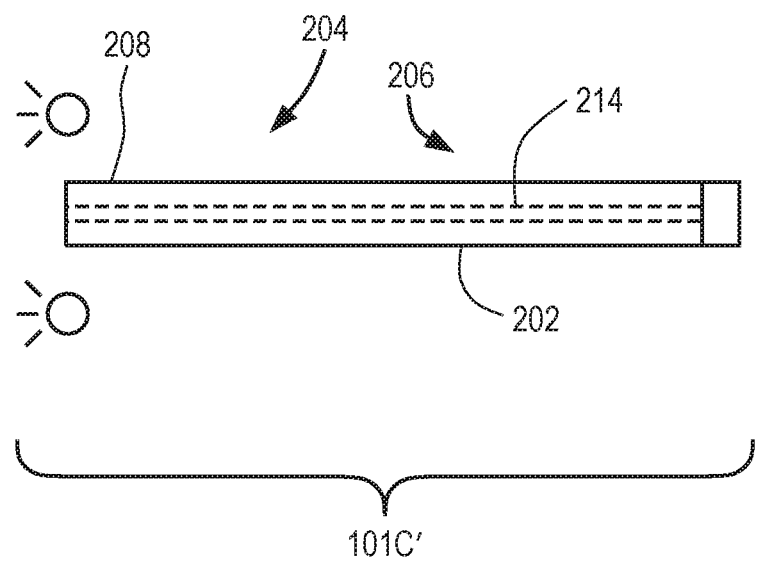
FIG. 7B is an illustrative drawing of a second image capture system in accordance with some embodiments.

FIG. 7B is an illustrative drawing of a second endoscope with a second image capture system 101C2, in accordance with some embodiments. Aspects of the second image capture system 101C2 that are essentially the same as those of the first endoscope with the first image capture system 101C are indicated by identical reference numerals and are not described again. An input to a light pipe input, such as a rod lens, is disposed at the tip portion 208 of the first end portion 204. A light pipe body extends within the elongate portion 202 so as to transmit an image received as the light pipe input to the imager sensor array 210, which is physically displaced from the tip portion 208. In some embodiments, the imager sensor array 210 is displaced far enough from the tip portion 208 so that the imager sensor array 210 is located outside the body cavity during observation of objects within the cavity.

Figure 8:
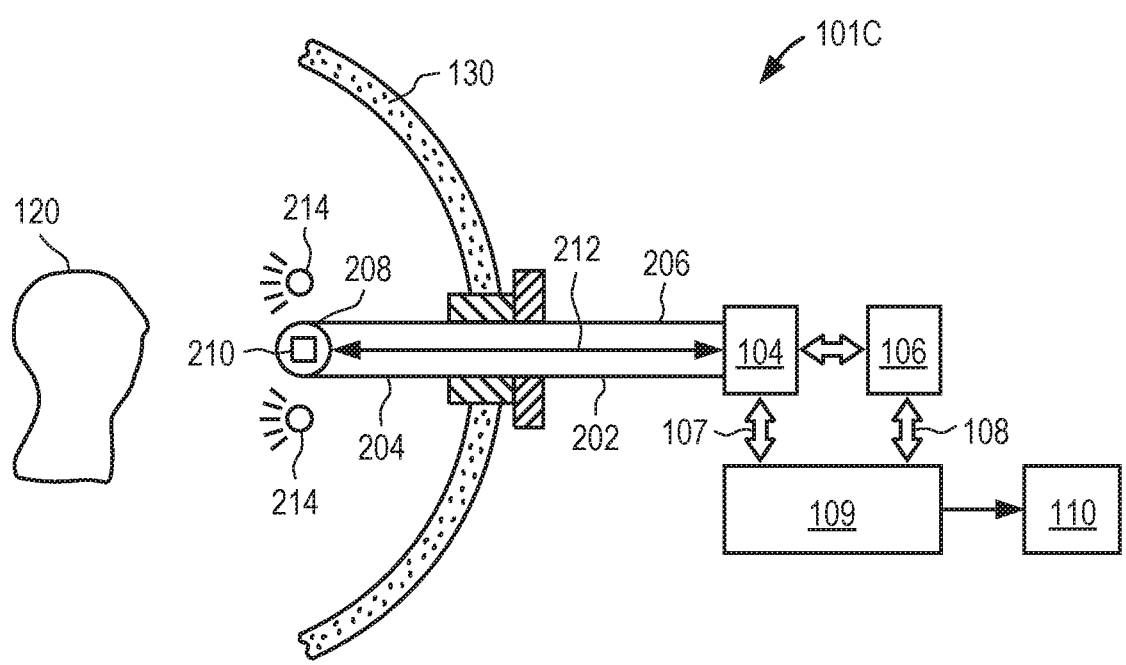
FIG. 8 is illustrative block diagram showing control blocks associated with the first image capture system of FIG. 7A and showing the system in operation, in accordance with some embodiments.

FIG. 8 is illustrative block diagram showing control blocks associated with the first endoscope 101C with the first image capture system 101C of FIG. 7A and showing the system in operation, in accordance with some embodiments. Images captured by the imager sensor array 210 are sent over a data bus 212 to a video processor 104, which communicates via bus 105 with a controller 106. The video processor 104 may comprise a camera control unit (CCU) and a video signal detector (VSD) board. The CCU programs or controls various settings of the imaging sensor 210, such as brightness, color scheme, white balance, etc. The VSD processes the video signal received from the imaging sensor. Alternatively, the CCU and VSD are integrated into one functional block.

In accordance with some embodiments a processor system that includes one or more than one processor is configured to perform processor functions. In some embodiments the processor system includes multiple processors configured to operate together to perform the processor functions described herein. Thus, reference herein to at least one processor configured to perform one or more functions includes a processor system in which the functions may be performed by one processor alone or by multiple processors working together.

In one implementation, the controller 106, which includes a processor and a storage device (not shown) computes the physical quantitative 3D coordinates of the points in a scene adjacent the tip 208 of the elongate portion 202 and drives both the video processor 104 and a 3D display driver 109 to compose 3D scenes, which then can be displayed on a 3D display 110. In accordance with some embodiments, Q3D information about a surgical scene is generated, such as numerical indicia of dimensions of surface contours of objects in a scene or distances from objects within the surgical scene, for example. As explained more fully below, the numerical Q3D depth information can be used to annotate a stereoscopic image of a surgical scene with distance information or surface contour information.

Data buses 107 and 108 exchange information and control signals among the video processor 104, the controller 106, and the display driver 109. In some embodiments, these elements can be integrated with the image sensor array 210 inside the body of the endoscope. Alternatively, they can be distributed internally and/or externally to the endoscope. The endoscope is shown positioned, via a cannula 140, to penetrate body tissue 130 in order to provide visualize access to a surgical scene that includes a target 120. Alternatively, the endoscope and one or more instruments may also pass through a single opening—a single incision or natural orifice—to reach a surgical site. The target 120 can be an anatomic target, another surgical instrument, or any other aspect of the surgical scene inside a patient's body.

Figure 25:
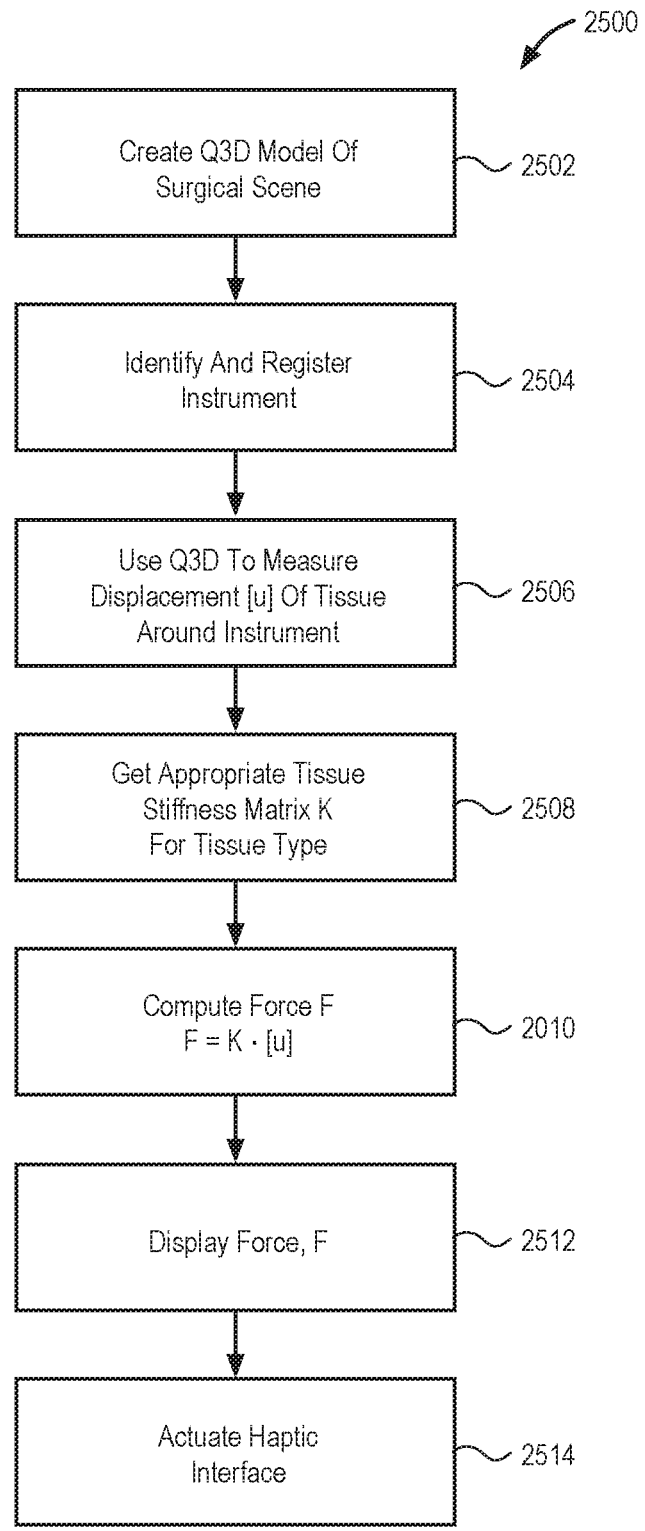
FIG. 25 is an illustrative flow diagram representing a process to use Q3D information to determine haptic feedback in accordance with some embodiments.

An input system 112 receives the 3D visual representation and provide it to processor 106. The input system 112 may include a storage device coupled to an electronic communication bus (not shown) that receives a 3D model such as a CRT or MRI from a system (not shown) that generates the 3D model. Processor 106, for example, can be used to compute the alignment intended between the Q3D model and the 3D visual representation. More particularly, without limitation, input system 112 may include a processor configured to establish an Ethernet communication connection between system 152 and an imaging system (not shown), such as a MRI, CT or ultrasound imaging system. Other imaging systems may be used. Other types of communication connections may be used, such as Bluetooth, WiFi, optical, etc. Alternatively, system 152 and the imaging system may be integrated in one larger system. The result of the alignment process may be saved in the storage device associated with processor 106, provided for further manipulation to external devices or system or displayed as shown in FIG. 25.

Example of Q3D Information Added to an Image of a Scene

Referring once again to FIG. 4 is an illustrative drawing showing a perspective view of a viewer 312 of the master control console 150 of FIG. 5 in accordance with some embodiments. In accordance with some embodiments, to provide a three-dimensional perspective, the viewer 312 includes stereo images for each eye. As shown, a left image 400L and a right image 400R of the surgical site include any instruments 400 and a target 410 respectively in a left viewfinder 401L and a right viewfinder 401R. The images 400L and 400R in the viewfinders may be provided by a left display device 402L and a right display device 402R, respectively. The display devices 402L,402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L, 402R; such as color CRTs or color LCDs. To support backward compatibility with existing devices, stereoscopic display devices 402L and 402R may be used with a Q3D system. Alternatively, the Q3D imaging system can be connected to 3D monitors, 3D TVs, or to autostereoscopic displays, such as a display that does not require use of 3D effect eye glasses.

A viewing system having two viewing elements 401R, 401L can provide a good 3D viewing perspective. The Q3D imaging system supplements this viewing perspective with physical dimension information for physical structures in the surgical scene. The stereo viewer 312 used in conjunction with a Q3D endoscopy system, can display Q3D information overlayed onto the stereo image of the surgical scene. For example, as shown in FIG. 4, the numerical Q3D distance value "d_Instr_Trgt" between instrument 400 and target 410 can be displayed within stereo viewer 312.

An explanation of a video stereo viewing system that can be used to overlay physical location and dimension information onto a 3D perspective of a surgical scene is provided in U.S. Patent Application Pub. No. U.S. 2012/0020547, (filed Sep. 30, 2011), paragraphs [0043]-[0053] and corresponding drawings, which is expressly incorporated herein by reference.

Processing Quantitative Three-Dimensional Physical Information

Figure 9:
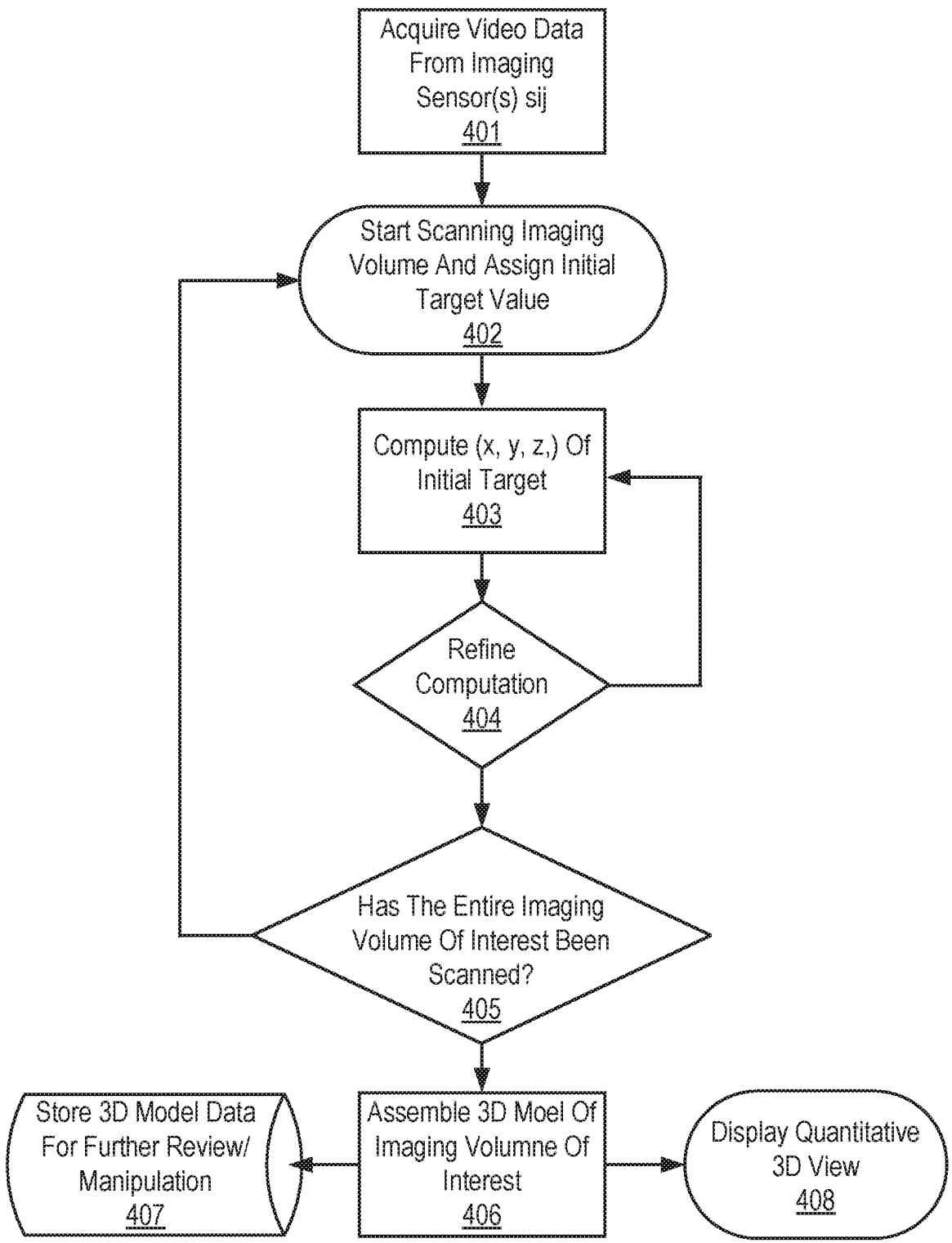
FIG. 9 is an illustrative flow diagram representing a process to determine a quantitative three dimensional location of a physical target in accordance with some embodiments.

FIG. 9 is an illustrative flow diagram representing a process to determine a quantitative three-dimensional location of a physical target in accordance with some embodiments. The process is described with reference to the endoscope with image capture system 101C of the embodiment of FIG. 8. Module 401 configures the controller 106 to acquire video data from imaging sensors $S_{ij}$. It will be appreciated that although the image sensor array 210 "images" an entire field of view, different sensors and different pixels within different sensors in image sensor array 210 may be illuminated by image projections from different object points within the field of view. The video data, for example, may include color and light intensity data. Each pixel of each sensor may provide one or more signals indicative of the color and intensity of an image projected onto it. Module 402 configures the controller to systematically select targets from a selected region of interest in a physical world view. Module 403 configures the controller to commence the computation of the target 3D coordinates (x, y, z) with an initial $(x_0, y_0, z_0)$ set. The algorithm then checks the coordinates for consistency, by using image diversity data from all sensors $S_{ij}$ that receive a projected image of the target. The coordinate computation is refined at decision module 404 until an acceptable accuracy is reached. Decision module 404 also configures the controller to determine whether the currently computed physical location is sufficiently accurate. In response to a determination that the currently computed location is not accurate enough, control flows back to module 403 to try a different possible physical location. In response to a determination that the currently computed location is sufficiently accurate, module 405 configures the controller to determine whether the entire region of interest has been scanned. In response to a determination that the entire region of interest has not been scanned, control flows back to module 402 and a different target is selected. In response to a determination that the entire region of interest has been scanned, control flows to module 406, which configures the controller to assemble a three-dimensional model of the imaging volume of interest. Assembly of a 3D image of a target based upon three-dimensional information indicating the physical position of structures of the target is known to persons of ordinary skill in the art and need not be described herein. Module 407 configures the controller to store the 3D model developed using the physical position information determined for multiple targets for further review and manipulation. For example, the 3D model could be used at a later time for surgical applications, such as sizing an implant for the particular dimensions of a patient's organ. In yet a different example, when a new surgical instrument 101 is installed on the robotic system 152, it may be necessary to call back the 3D model and display it on display 110 in order to reference the new instrument to the previous surgical scene. Module 407 may also store the result of the alignment between the 3D visual representation and the Q3D model. Module 408 configures the controller to use the physical position information determined for multiple targets to display a quantitative 3D view. An example of a Q3D view is the distance value "d_Instr_Trgt" shown in FIG. 4.

It is noted that a stereoscopic display creates the illusion of viewing in three dimensions. However, an actual 3D display presents a 3D image, such as a holographic image or an image projected onto a curved surface. Typically, a 3D display allows the view to move to change viewing perspective.

Figure 10:
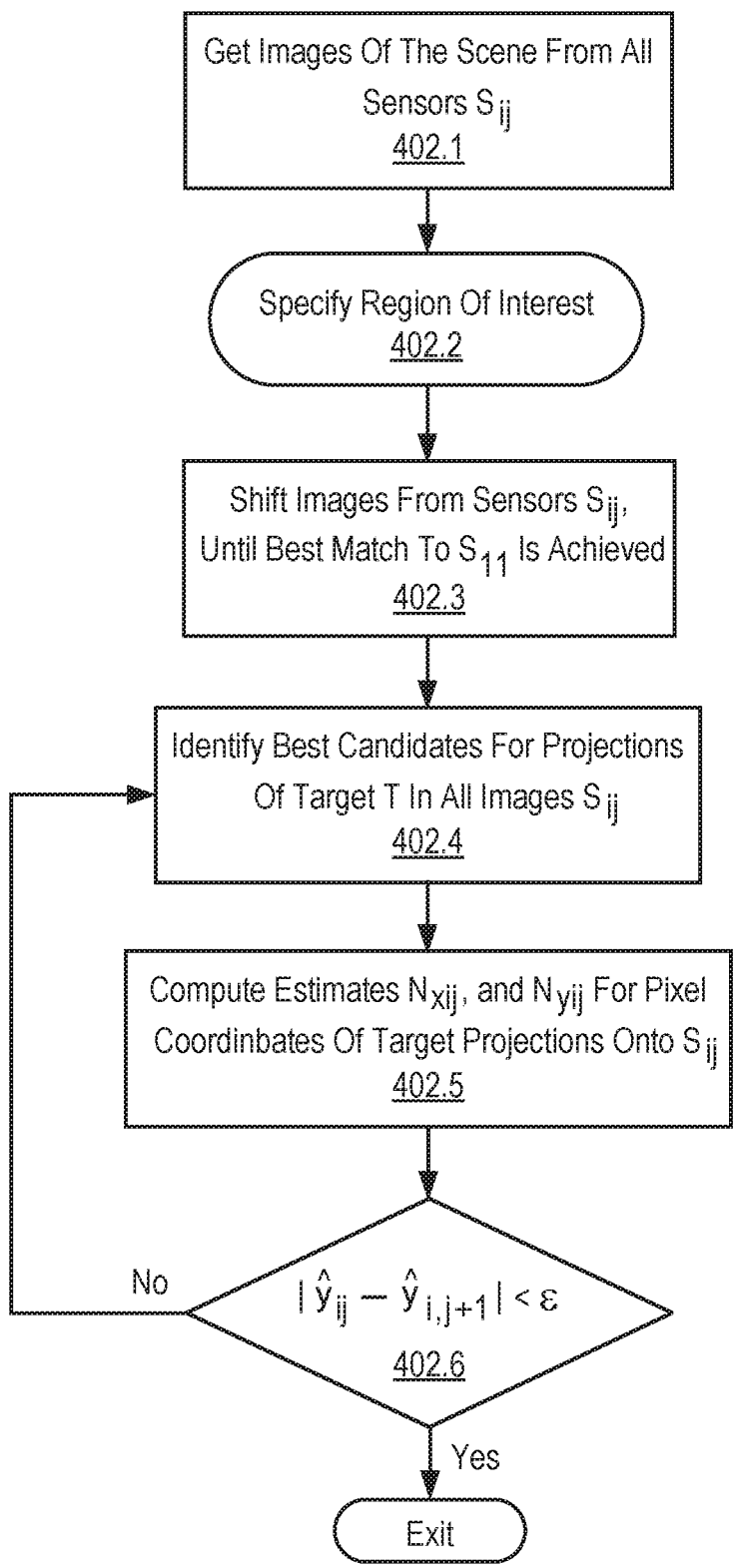
FIG. 10 is an illustrative flow diagram showing certain details of a process generally corresponding to module FIG. 9 to systematically select targets in accordance with some embodiments.

FIG. 10 is an illustrative flow diagram showing certain details of a process generally corresponding to module 402 of FIG. 9 in accordance with some embodiments. Module 402.1 configures the controller to capture images of a physical world scene from all sensors in the sensor array 210. Module 402.2 configures the controller to specify a region of interest from within the captured scene. Module 402.3 configures the controller to search for a best match as between scene images within the region of interest so as to identify pixel locations in different sensors that are illuminated by projections of the same target. As explained later, the best matching may be achieved, without limitation, by shifting the individual images from sensors $S_{ij}$ until maximizing two-dimensional cross-correlation function between the shifted image and a reference image. The reference image, for example, may be the scene image received from sensor $S_{11}$. Module 402.4 configures the controller to identify candidate pixels illuminated by projections from the same target. Module 402.5 configures the controller to compute two or more pixel coordinates $(N_x, N_y)$ coordinates for the selected target to determine whether the candidate pixels are illuminated by a projection from the same target. Decision module 402.6 determines whether the computed 2D pixel coordinate values indicate that the candidate pixels are illuminated by a projection from the same target. The image diversity caused by viewing the same scene with multiple sensors $S_{ij}$ plays a role in correctly identifying $(N_x, N_y)$ associated with a specific target in the various individual images $S_{ij}$. For example, in accordance with some embodiments, assuming a simplified scenario where only three sensors are used, $S_{11}$, $S_{12}$ and $S_{13}$, if the triplet of 2D pixel coordinates $[(Nx_{11}, Ny_{11}), (Nx_{12}, Ny_{12}), (Nx_{13}, Ny_{13})]$ are not corresponding to projections of the same target onto $[S_{11}, S_{12}$ and $S_{13}]$ then the quantities $\hat{y}_{12}$ and $\hat{y}_{13}$ (which are estimates of the projection shift in the y direction) will yield different values. According the equations presented later, $\hat{y}_{12}$ and $\hat{y}_{13}$ should be equal if pixel coordinates $(Nx_{11}, Ny_{11})$, $(Nx_{12}, Ny_{12})$, $(Nx_{13}, Ny_{13})$ come from projections of the same target.

$$\hat{y}_{12} = \frac{Ny_{11}}{Ny_{11} - Ny_{12}} \quad (402.5\text{-}1)$$

$$\hat{y}_{13} = 2 \cdot \frac{Ny_{11}}{Ny_{11} - Ny_{13}} \quad (402.5\text{-}2)$$

If $\hat{y}_{12}$ and $\hat{y}_{13}$ are not approximately equal then control flows back to module 402.4 and to refine the best candidates for target projections onto sensor planes $S_{ij}$. As mentioned, the above is just a simplified implementation of the algorithm. In general, as shown in FIG. 10 module 402.6, the norm of the difference between $\hat{y}_{i,j}$ and $\hat{y}_{i,j+1}$ should be less than an acceptable tolerance ε in order for module 402 to complete its iterations. A similar restriction should be met for the corresponding estimates for the x axis, $\hat{x}_{i,j}$ and $\hat{x}_{i,j+1}$. In response to a determination that the computed 2D pixel coordinate values $(N_x, N_y)$ do indicate that the candidate pixels are illuminated by a projection from the same target, then control flows to module 403.

It will be appreciated that each pixel directly captures color and intensity information from a world scene. Moreover, in accordance with the above process, each pixel is associated with the (x, y, z) coordinates of the physical object in the world view that is projected onto the pixel. Thus, color information, illumination intensity information and physical location information, i.e. the location of the physical object that projected the color and illumination, can be associated with a pixel in a non-transitory computer readable storage device. The following Table 1 illustrates this association.

TABLE 1

| Pixel Identifier | Color Value | Intensity Value | Location (x, y, z) |
| --- | --- | --- | --- |

Examples of Determining Q3D Information

Example of Projection Matching

Figure 11:
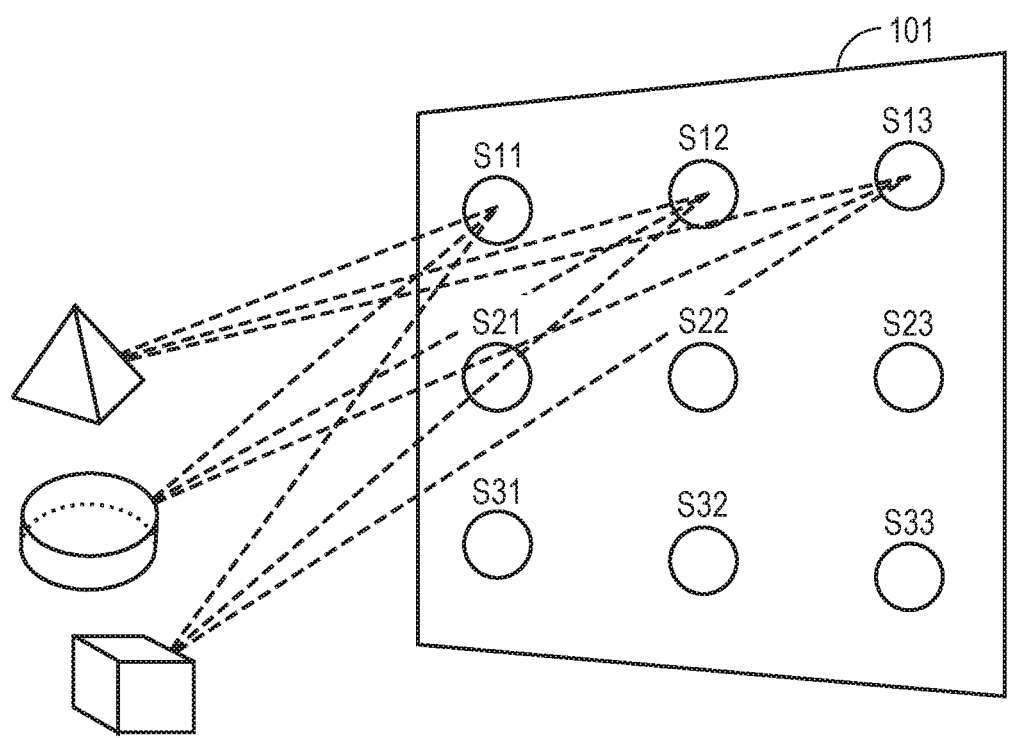
FIG. 11 is an illustrative drawing of an example sensor imager array that includes multiple sensors and that is disposed to have a field of view that encompasses an illustrative three dimensional physical world scene that includes three illustrative objects in accordance with some embodiments.

FIG. 11 is an illustrative drawing of an example sensor array 210 that includes an array of sensors $S_{11}$-$S_{33}$ that is disposed to have a field of view that encompasses an illustrative three-dimensional physical world scene that includes three illustrative objects in accordance with some embodiments. Each sensor $S_{ij}$ in the array includes a two-dimensional arrangement of pixels having at least two pixels in each dimension. Each sensor includes a lens stack that creates a separate optical channel that resolves an image onto a corresponding arrangement of pixels disposed in a focal plane of the lens stack. Each pixel acts as a light sensor, and each focal plane with its multiple pixels acts as an image sensor. Each sensor $S_{11}$-$S_{33}$ with its focal plane occupies a region of the sensor array different from regions of the sensor array occupied by other sensors and focal planes. Suitable known image sensor arrays are disclosed in U.S. Pat. No. 8,514,491 (filed Nov. 22, 2010) and in U.S. Patent Application Pub. No. US 2013/0070060 (filed Sep. 19, 2012), which are described above.

In accordance with some embodiments, the sensors are characterized by a $N_x$ and $N_y$, their total number of pixels in the x and y directions, and by field of view angles, $\theta_x$ and $\theta_y$. In some embodiments, the sensor characteristics for the x and y axes are expected to be the same. However, in alternative embodiments, the sensors have asymmetric x and y axis characteristics. Similarly, in some embodiments, all sensors will have the same total number of pixels and the same field of view angle. The sensors are distributed across the sensor array 210 in a well-controlled manner. For example, the sensors may be at $\delta$ distance apart on the two-dimensional grid shown. The sensor placement pitch $\delta$ may be symmetric or asymmetric across such grid.

In the embodiment shown in FIG. 11, the sensors are arranged in a rectangular grid in which sensors $S_{11}$-$S_{13}$ occupy a top row, sensors $S_{21}$-$S_{23}$ occupy a middle row, and sensors $S_{31}$-$S_{33}$ occupy a bottom row. Each sensor includes N rows of pixels and N columns of pixels. Light rays, indicated by dashed lines, produced by a light source are reflected from each of a triangular-shaped first object, a spherical-shaped second object, and a rectangular-shaped third object, to each sensor of the imager array. For illustration purposes, only rays to sensors $S_{11}$, $S_{12}$ and $S_{13}$ in the top row are shown. The light source may be non-structured white light or ambient light, for example. Alternatively, the light source may provide light at a selected wavelength, such as in the visible or infrared spectrums, or the light may be filtered or split to provide a selected wavelength (e.g., color) or range of wavelengths (e.g., range of colors), for example. It will be appreciated that light rays are similarly reflected from each of the objects to sensors $S_{21}$-$S_{33}$. However, in order to simplify the explanation, these other light rays are not shown.

Figure 12:
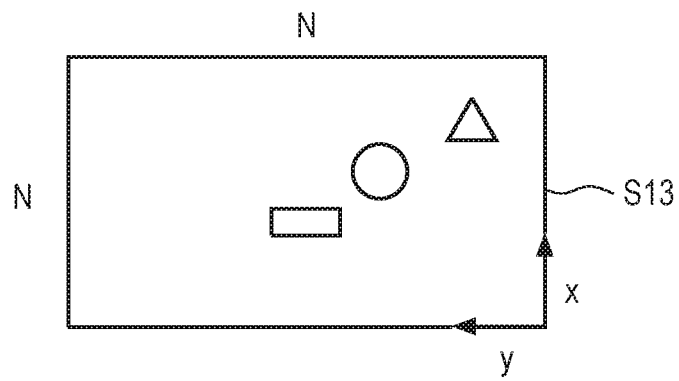
FIG. 12 is an illustrative drawing representing projections of the multiple physical objects of FIG. 11 onto multiple sensors in accordance with some embodiments.
Figure 12:
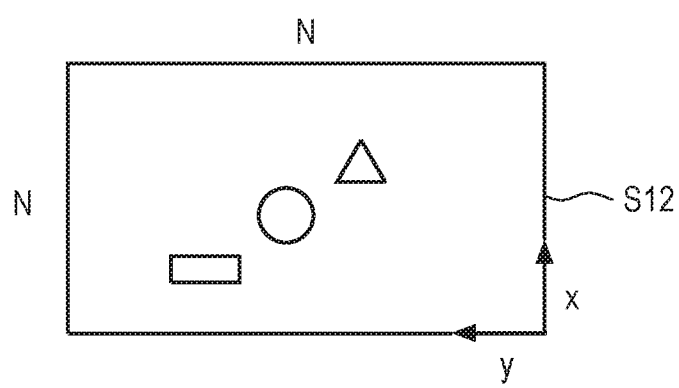
Figure 12:
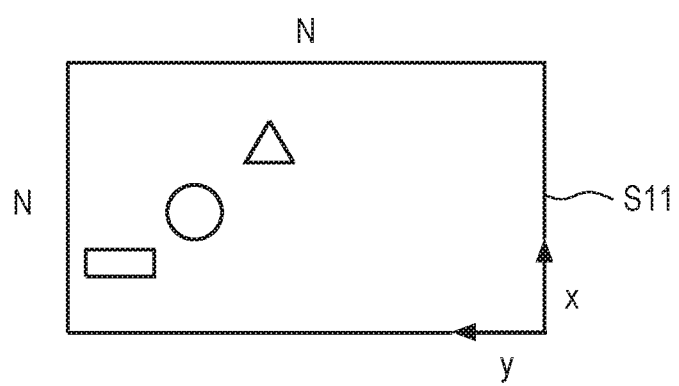

In accordance with modules 401 and 402.1, sensors of the sensor array 210 separately capture images from a world view. FIG. 12 is an illustrative drawing representing projections of the three objects of FIG. 11 onto the sensors $S_{ij}$ (only $S_{11}$, $S_{12}$, and $S_{13}$ are shown) in accordance with some embodiments. A person of ordinary skill in the art will appreciate that the reflected light rays incident upon the sensors project images of the objects that are in the field of view. More specifically, the rays of light reflected from the objects in the field of view that are incident upon multiple different image sensors of the imager array produce multiple perspective projections of the objects from three dimensions to two dimensions, i.e. a different projection in each sensor that receives the reflected rays. In particular, the relative location of projections of the objects is shifted from left to right when progressing from $S_{11}$ to $S_{12}$ to $S_{13}$. Image sensor pixels that are illuminated by incident light rays produce electrical signals in response to the incident light. Accordingly, for each image sensor, a pattern of electrical signals is produced by its pixels in response to the reflected rays that indicates the shape and location of the image projection within that image sensor.

Figure 13:
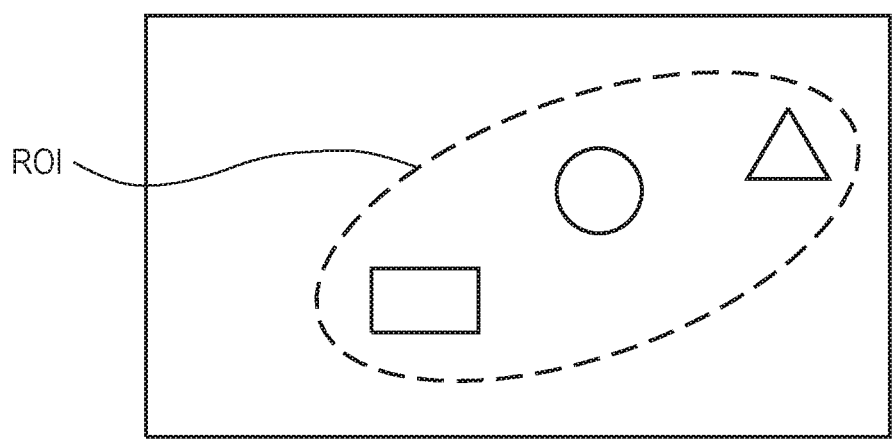
FIG. 13 is an illustrative drawing indicating selection of a region of interest from within a real-world scene in accordance with some embodiments.

In accordance with module 402.2, a region of interest is selected from the world scene. FIG. 13 is an illustrative drawing indicating selection of a region of interest from within the scene. In this example, the triangular-shaped first object, spherical-shaped second object, and rectangular-shaped third object all are in the selected region of interest. This step can be achieved by accepting input from an operator, or it can be automatically performed using a computer configured by software in a prescribed manner, or by combination of operator inputs and automatic software-controlled selection. For example, in some embodiments, the world scene may show an internal cavity of the human anatomy, and the objects may be internal body organs, or surgical instruments, or portions thereof. A surgeon may receive real time visual imagery from within the internal cavity and may see tissue regions of the human anatomy and a portion of the surgical instruments projecting within the body cavity. The surgeon may specify those objects within the field of view for which location information is to be determined through well-known techniques, such as a telestration video marker. Alternatively or in addition to such operator request, an automated process such as an edge detection algorithm can be used to specify a region of interest (ROI).

Figure 14:
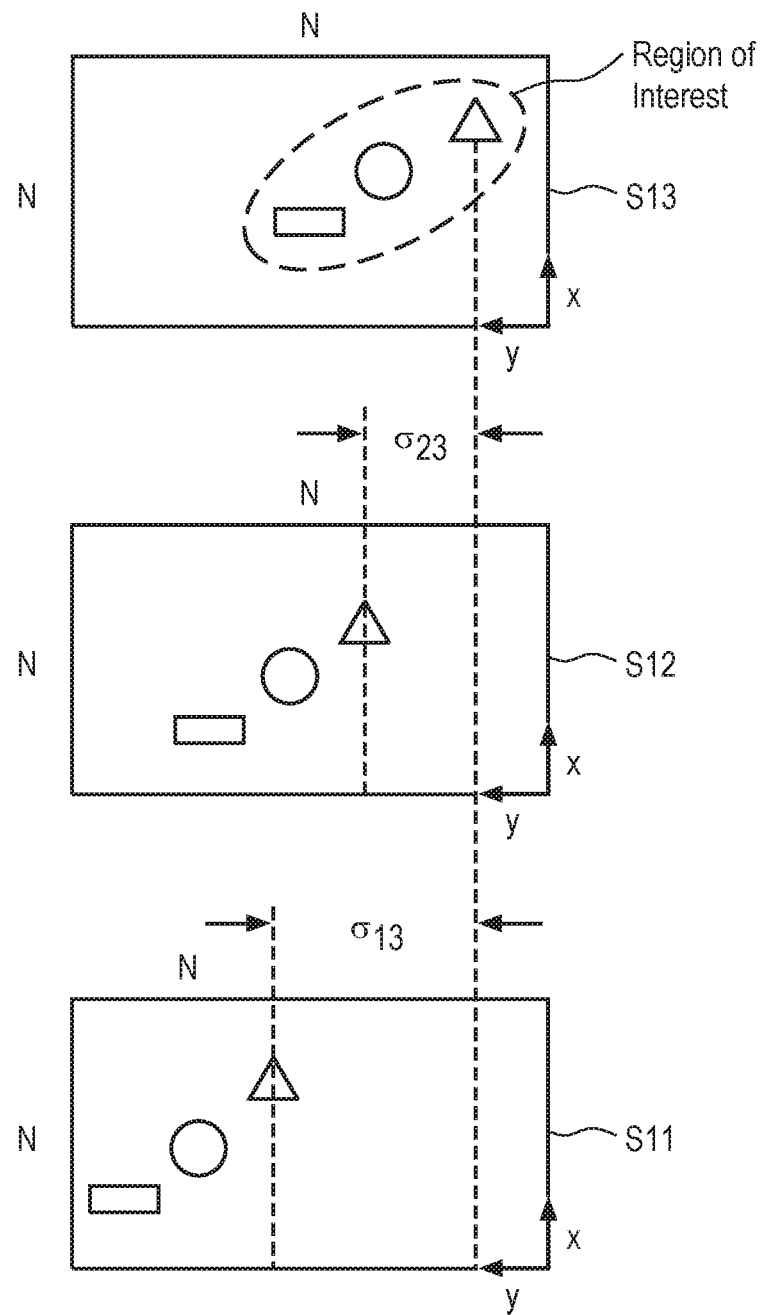
FIG. 14 is an illustrative drawing showing detail as to relative geometric offset of the projected images in sensors multiple sensors in accordance with some embodiments.

In accordance with module 402.3, a best match is determined between scene images within the region of interest so as to identify pixel locations in different sensors that are illuminated by projections of the same target. FIG. 14 is an illustrative drawing showing additional detail about relative geometric offset of the projected images in sensors $S_{11}$, $S_{12}$, and $S_{13}$ in accordance with some embodiments. In accordance with some embodiments, an image from sensor $S_{13}$ is considered to be reference image, and the projections of the objects in the selected ROI are offset to the right by an amount $\sigma_{23}$ pixels in sensor $S_{12}$ relative to their location in sensor $S_{13}$. Similarly, the projections of the objects in the selected ROI are offset to the right by an amount $\sigma_{13}$ pixels in sensor $S_{11}$ relative to their location in sensor $S_{13}$. It will be appreciated that since the FOV viewing axes of sensors $S_{12}$, $S_{11}$ each is offset to the right of the FOV viewing axis of sensor $S_{13}$ (such viewing axes being perpendicular to plane of the sensors), the projected images from ROI are offset to the left in the sensors $S_{13}$ and $S_{11}$ relative to sensor $S_{11}$.

Figure 15:
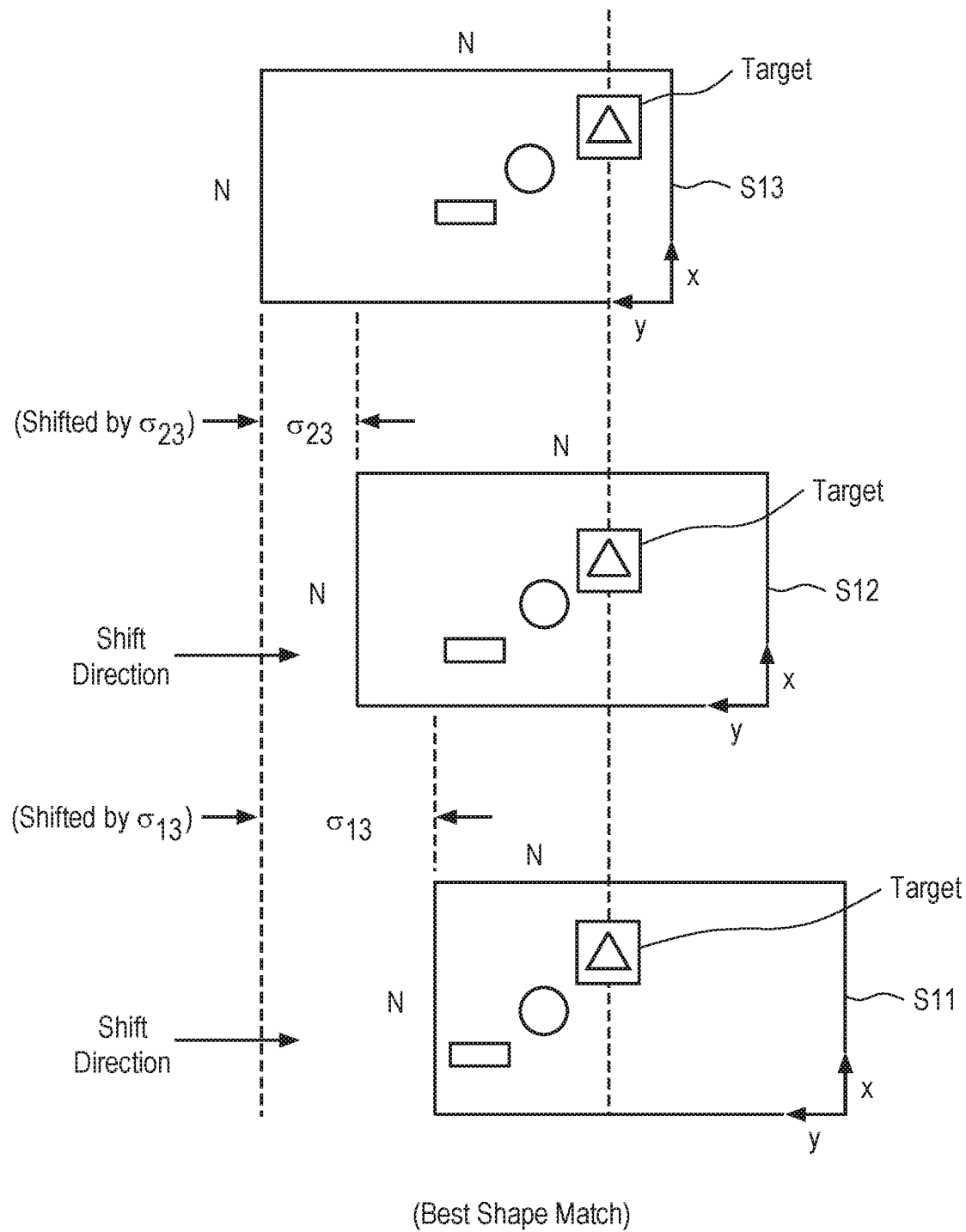
FIG. 15 is an illustrative drawing showing the projected images in certain example sensors within the region of interest (ROI) shifted to the right to align with the projected images in a designated reference sensor within the ROI in accordance with some embodiments.

FIG. 15 is an illustrative drawing showing the projected images in sensors $S_{11}$ and $S_{12}$ within the ROI shifted to the right to align with the projected images in sensor $S_{13}$ within the ROI in accordance with some embodiments. In the current example, sensor $S_{13}$ is designated to act as a reference sensor. It will be appreciated that other sensors can be chosen for use in determining alignment and geometric dimensions. Projections of the objects within the selected ROI are identified in the designated sensor, e.g., sensor $S_{13}$, and projections in the other sensors, e.g., in sensors $S_{11}$ and $S_{12}$, are shifted until they align with the projection in the designated sensor. In this manner, the corresponding projections of objects within the selected ROI can be identified within the other sensors, together with their offsets relative to the location of the projections in the designated sensor.

In particular, for example, the projections of the three example objects are shifted to the right by an amount $\sigma_{23}$ pixels in sensor $S_{12}$, and the projections of the three example objects are shifted to the right by an amount $\sigma_{13}$ pixels in sensor $S_{13}$. In this illustrative example, in order to simplify the explanation, it is assumed that the projections are offset in the y direction only and not in the x direction, although the same principles apply for x direction projection offsets as between sensors. Moreover, although this example shows a linear offsets, a person of ordinary skill in the art can apply other transformations such as rotation, for example, to align projections that have relative offsets in different sensors.

In accordance with some embodiments for example, two-dimensional (2D) cross-correlation techniques or principal component analysis (PCA), can be used to align the projections within the ROI in $S_{13}$ with the projections within the ROI in $S_{12}$ and to align the projections within the ROI in $S_{13}$ with the projections within the ROI in $S_{11}$. In general, the intent is to best match or align the images from sensors $S_{ij}$ with respect to the image from the sensor designated as reference. More specifically, the projected images within the ROI in $S_{12}$ are shifted and cross-correlated with the projected images within the ROI in $S_{13}$ until a highest correlation coefficient is achieved. Likewise, the projected images within the ROI in $S_{11}$ are shifted and cross-correlated with the projected images within the ROI in $S_{13}$ until a highest correlation coefficient is achieved. Thus, alignment of the projections of the ROI is used to identify the locations of the projections of the ROI in sensors $S_{11}$ and $S_{12}$ by determining the offset between the projection of the ROI in $S_{13}$ and the projection of the ROI in $S_{12}$ and by determining the offset between the projection of the ROI in $S_{13}$ and the projection of the ROI in $S_{11}$.

Example of Candidate Pixel Selection and Refinement

In accordance with module 402.4, candidate pixels are identified within different sensors, which according to the best match process, are illuminated by projections from the same target. Once the projections of objects within the ROI have been identified in each of the sensors $S_{11}$, $S_{12}$, and $S_{13}$, the physical (x, y, z) projections of individual target points within the ROI can be determined relative to the imager array. In accordance with some embodiments, for each of a multiplicity of target points within the ROI, one or more pixels within each of multiple sensors is identified that is illuminated by a projection from the target point. For each such target point, a physical (x, y, z) target point location is determined based at least in part upon the geometric relationships among pixels disposed in different sensors that are determined to be illuminated by projections from the target point.

It will be appreciated that a sequence of target points can be chosen automatically by systematically traversing the ROI (e.g., right to left with a certain step size and up to down with a step size), and a physical (x, y, z) target point location can be determined for each selected target point. Since $S_{11}$ and $S_{12}$ are best matched to $S_{13}$, the traversing is performed inside the shifted regions of interest. Selecting a target involves identifying a pixel in each of sensors $S_{11}$, $S_{12}$, and $S_{13}$ that is illuminated by a projection of the target. Thus, candidate pixels in each of $S_{11}$, $S_{12}$, and $S_{13}$ are identified as being the ones illuminated by a projection of the selected target point.

In other words, in order to select a target point T, a pixel is selected in each of the sensors $S_{11}$, $S_{12}$, and $S_{13}$ that is illuminated by a projection of the target point T. It will be appreciated that the (x, y, z) physical location of the target T is unknown at the moment of its selection. Moreover, it will be appreciated that inaccuracy of the above-described alignment process can result in inaccuracy in the determination of which pixels in each sensor are illuminated by the projection of a selected target T. Thus, as explained with reference to FIGS. 17, 18, and 19, a further determination is made as to the accuracy of the determination as to the pixels in each of $S_{11}$, $S_{12}$, and $S_{13}$ that are illuminated by the projection of a currently selected target T.

Figure 16:
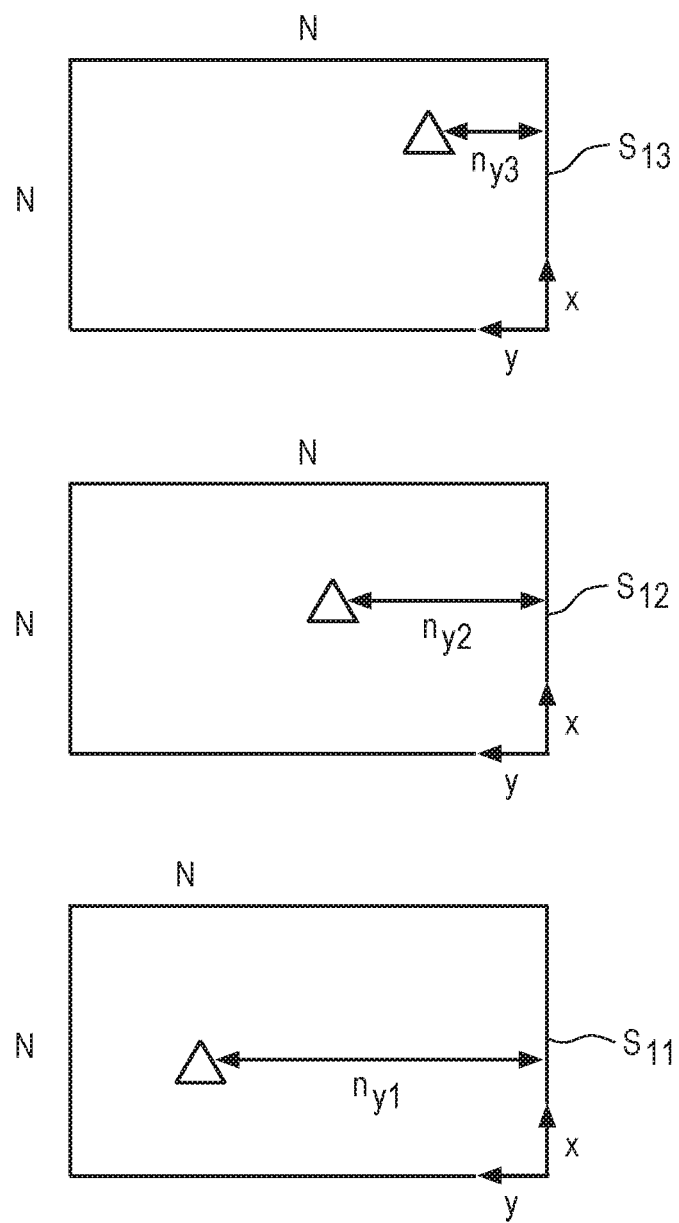
FIG. 16 is an illustrative drawing showing projections of a selected target point onto multiple sensors in accordance with some embodiments.

Continuing with the above example, assume that the triangular-shaped first object is the currently selected target point. FIG. 16 is an illustrative drawing showing projections of the selected triangle shaped target point onto sensors $S_{11}$, $S_{12}$, and $S_{13}$ in accordance with some embodiments. From these projections, the 2D pixel coordinates for target T are determined, $[(Nx_{11}, Ny_{11}), (Nx_{12}, Ny_{12}), (Nx_{13}, Ny_{13})]$. For simplification, FIG. 16 shows only the y-axis pixel coordinates. Using these 2D pixel coordinates, expressions (402.5-1) and (402.5-2) are applied and $\hat{y}_{12}$ and $\hat{y}_{13}$ computed as part of module 402.5. As part of module 402.6, the norm $|\hat{y}_{12} - \hat{y}_{13}|$ is computed and compared to the acceptable tolerance $\varepsilon$. Similarly, the x-axis pixel coordinates and location estimates are computed and compared against acceptable tolerances. If the condition of module 402.6 is met, then the process proceeds to module 403. Else, it returns to module 402.4 to further refine target candidates.

Figure 17:
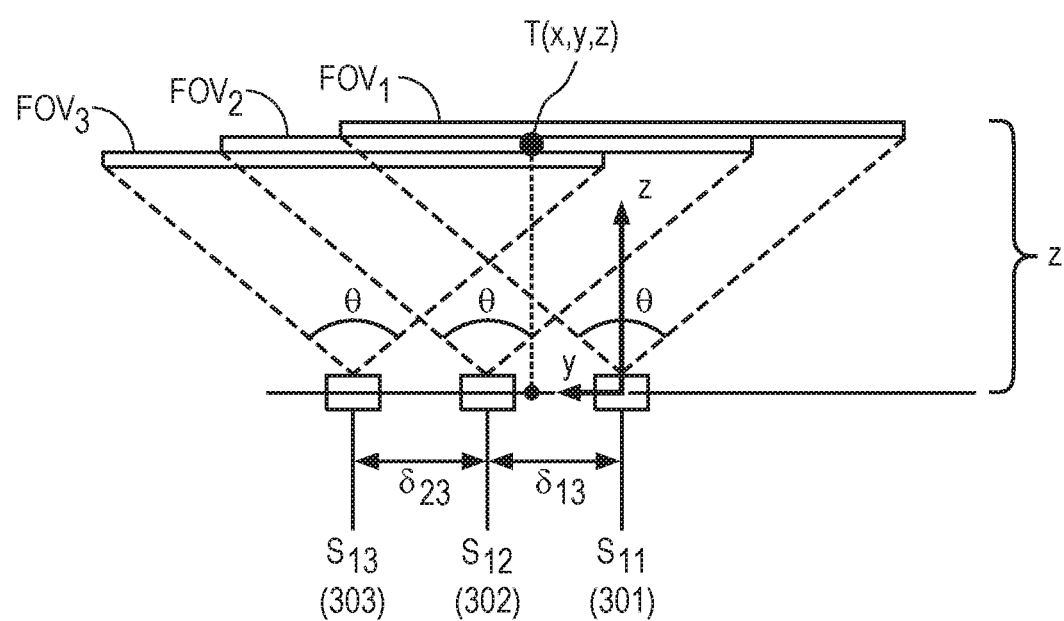
FIG. 17 is an illustrative drawing showing a portion of an imager array that includes the multiple sensors of FIG. 16 and the selected target point T disposed at location in physical space in accordance with some embodiments.

Referring to FIG. 17, there is shown a portion of an imager array that includes sensors $S_{11}$, $S_{12}$, and $S_{13}$ and the selected triangular-shaped first object target point T disposed at location (x, y, z) in physical space. Sensors within an imager array have a known spacing between them, $\delta_{ij}$. The physical position spacing between $S_{11}$ and $S_{12}$ is $\delta_{12}$, and the physical position spacing between $S_{12}$ and $S_{13}$ is $\delta_{23}$. In some embodiments the spacing between all sensors $S_{ij}$ is identical, equal to $\delta$, a constructional specification. Sensors $S_{ij}$ also have a known field of view angle $\theta$.

As explained above, in some embodiments, each sensor is constructed as a 2D imaging element with pixels arranged in a rectangular pattern of rows and columns. Alternatively, pixels can be arranged in a circular pattern, zigzagged pattern, scattered pattern, or an irregular pattern including sub-pixel offsets, for example. The angle and the pixel characteristics of these elements may be identical or, alternatively, may be different from sensor to sensor. However, these characteristics are assumed to be known. In order to simplify the explanation, it is assumed that the sensors are identical, although they may, however, be different.

For simplicity, let us assume that all sensors $S_{ij}$ have N×N pixels. At a distance z from sensor $S_{11}$, the N-pixel width of the sensor expands out to a y-dimension field of view of $S_{11}$ indicated by $FOV_1$. Likewise, at a distance z from sensor $S_{12}$, the y-dimension field of view of sensor $S_{12}$ is indicated by $FOV_2$. Also, at a distance z from sensor $S_{13}$, the y-dimension field of view of sensor $S_{13}$ is indicated by length $FOV_3$. The lengths $FOV_1$, $FOV_2$, and $FOV_3$ overlap each other, signifying that sensors $S_{11}$, $S_{12}$, and $S_{13}$ achieve a 3-way sampling diversity of target T physically located at some (unknown) distance z. Of course, if the sensors are identically built, as assumed in this example, length $FOV_1$, $FOV_2$, and $FOV_3$ will be identical as well. It will be appreciated that the three lengths $FOV_1$, $FOV_2$, and $FOV_3$ all have the same magnitude and are coplanar in that they are at the same (unknown) z-distance from the imager array, although for the purpose of illustration they are portrayed as if they were stacked adjacent to each other.

Figure 18:
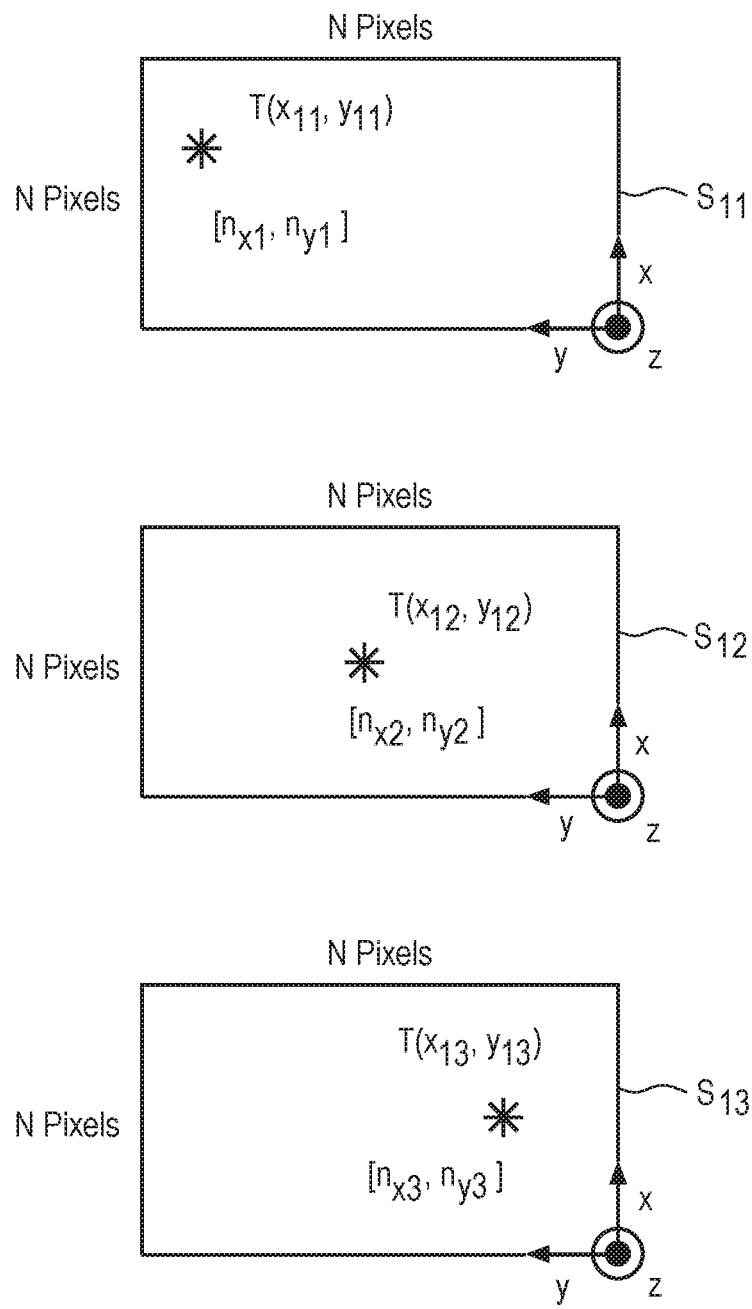
FIG. 18 is an illustrative elevation view of the projection of the currently selected target point T onto the multiple image sensors of FIG. 16 in accordance with some embodiments.

Referring to FIG. 18, there is shown an illustrative elevation view of the projection of the currently selected target point T onto the image sensors $S_{11}$, $S_{12}$, and $S_{13}$. For the sake of simplicity, it is assumed that the sensors include geometrically rectangular pixel arrays of size N×N pixels. It is also assumed that the x coordinates of the target T projections are all equal. In other words, it is assumed that for the projections of target T onto $S_{11}$, $S_{12}$, and $S_{13}$, $n_{x1}=n_{x2}=n_{x3}$. To simplify the explanation, it is also assumed that the geometric field of view angle θ is the same horizontally as it is vertically, $\theta_x=\theta_y$. A person of skill in the art would know how to modify the process presented below so that to compute the x, y, and z physical coordinates of target T if any of the above assumptions would change.

Figure 19:
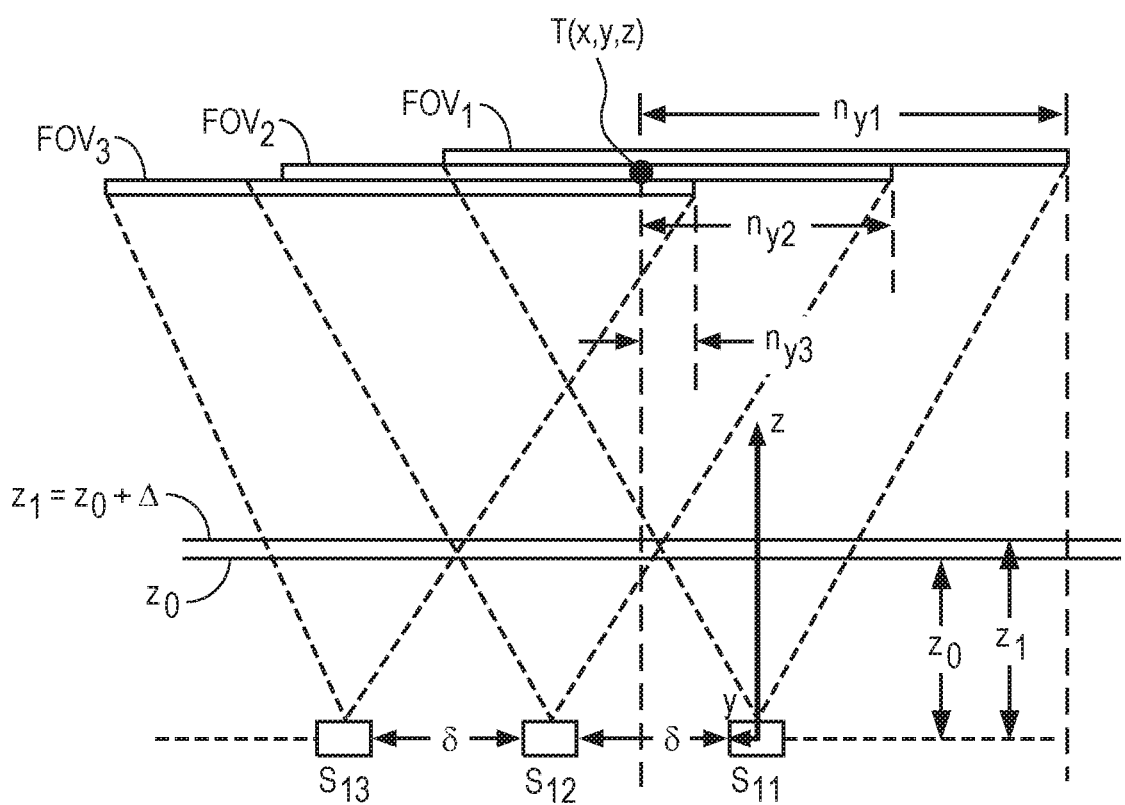
FIG. 19 is an illustrative drawing showing the disposition of a currently selected target relative to the multiple sensors as described above with reference to FIG. 17 and also showing y-direction pixel offsets for the candidate pixel in each of the sensors in accordance with some embodiments.

An image of the target T is projected to a physical point within sensor $S_{11}$ at geometric coordinates $(n_{x1}, n_{y1})$, in the plane of the image sensor $S_{11}$. More specifically, the projection of target point T onto sensor $S_{11}$ is located $n_{y1}$ pixels along the y axis, and $n_{x1}$ pixel along the x axis, taken from the origin. An image of the target T is projected to a physical point within sensor $S_{12}$ at geometric coordinates $(n_{x2}, n_{y2})$ in the plane of the image sensor $S_{12}$. An image of the target T is projected to a physical point within sensor $S_{13}$ at geometric coordinates $(n_{x3}, n_{y3})$ in the plane of the image sensor $S_{13}$. It will be appreciated that pixel locations $(n_{xi}, n_{yi})$ within each sensor are determined relative to origin (0, 0) reference coordinates provided for the sensor. As shown in FIG. 17 or FIG. 19, a global system of coordinates (x, y, z) is defined and used to reference the target. For example, the origin of such system of coordinates may be placed, without limitations, at the geometrical center of sensor $S_{11}$.

Referring to both FIG. 16 and FIG. 18, it can be seen that the y pixel distance of the projection of the target is different in each sensor. The projection of a currently selected target T is disposed $n_{y1}$ pixels to the left of the origin in $S_{11}$. The projection of the selected target T is disposed $n_{y2}$ pixels to the left of the origin in $S_{12}$. The projection of the selected target T is disposed $n_{y3}$ pixels to the left of the origin in $S_{13}$. As mentioned above, to simplify the explanation, it is assumed that the projection of the target falls at the same x pixel distance from the origin in all three sensors.

Referring to FIG. 19, there is shown the disposition of the currently selected target T relative to sensors $S_{11}$, $S_{12}$ and $S_{13}$ as described above with reference to FIG. 17 and also showing y-direction pixel offsets for the candidate pixel in each of the sensors. It will be understood that the drawings of FIG. 19 present physical structures and an analytical framework for determining the (x, y, z) physical coordinates of the selected target point T. At an (unknown) distance z from the imager array plane, the y-direction field of view for each sensor extends over a length marked as $FOV_1$. This length, $FOV_i$, corresponds to the maximum pixel width of the sensor, which is N pixels, in some embodiments. Given that the working assumption was that the sensor has a field of view that is symmetric in the x and y directions, the length would also be $FOV_i$ vertically, along the x axis.

Recall that the candidate pixel selections are made based at least in part upon a correlation process that can have a level of uncertainty than can result in inaccuracy in determination of the physical location of the selected target. Thus, a further check of the accuracy of the target projection candidate selections, in accordance with some embodiments, is made as follows.

Example of Determining Target's Physical (x, y) Location and Checking Accuracy of Target Projection Candidate Selection In accordance with module 402.5, two or more two-dimensional $(N_x, N_y)$ coordinate values are computed for the selected target to determine whether the candidate pixels actually are illuminated by a projection from the same target. Based on the assumptions discussed above and placing the origin of the 3D system of coordinates at the center of sensor $S_{11}$, the imager array and currently selected target T in the example in FIG. 19 have the following relationships:

$$z = \frac{N \cdot \delta}{2 \cdot (n_{y1} - n_{y2}) \cdot \tan\left(\frac{\theta}{2}\right)} \quad (1)$$

$$y = \frac{2n_{y1} - N}{2(n_{y1} - n_{y2})} \cdot \delta \quad (2)$$

$$x = \left(\frac{2n_{x1}}{N} - 1\right) \cdot z \cdot \tan\left(\frac{\theta}{2}\right) \quad (3)$$

Where:

N is the pixel dimension of the imaging sensors;

$n_{x1}$ is the position of a target point T expressed in number of pixels from the origin of the $S_{11}$ plane in the x direction;

$n_{y1}$ is the position of the target point T expressed in number of pixels from the origin of the $S_{11}$ plane in the y direction;

$n_{y2}$ is the position of the target point T expressed in number of pixels from the origin of the $S_{12}$ plane in the y direction; and $n_{y2}$ is the position of the target point T expressed in number of pixels from the origin of the $S_{12}$ plane in the y direction;

θ is the angle of the field of view

Moreover, if performing the same math using sensors $S_{11}$ and $S_{13}$ and given that the separation between $S_{11}$ and $S_{13}$ is 2δ, we obtain:

$$z = \frac{2 \cdot N \cdot \delta}{2 \cdot (n_{y1} - n_{y3}) \cdot \tan\left(\frac{\theta}{2}\right)} \quad (4)$$

$$y = \frac{2n_{y1} - N}{2(n_{y1} - n_{y3})} \cdot 2\delta \quad (5)$$

$$x = \left(\frac{2n_{x3}}{N} - 1\right) \cdot z \cdot \tan\left(\frac{\theta}{2}\right) + 2\delta \quad (6)$$

Where:

$n_{x3}$ is the position of a target point T expressed in number of pixels from the origin of the $S_{13}$ plane in the x direction; and $n_{y3}$ is the position of the target point T expressed in number of pixels from the origin of the $S_{13}$ plane in the y direction.

Thus, determination of the physical x coordinate of the selected target T can be determined based upon expressions (3) or (6). A determination of the physical y coordinate of the selected target T can be determined based upon expressions (2) or (5). A determination of the physical z coordinate of the selected target T can be determined based upon equations (1) or (4).

More generally, in accordance with module 402.6, a determination is made as to whether the computed 2D coordinate values indicate that the candidate pixels are illuminated by a projection from the same target. It will be appreciated that a more reliable determination of the physical (x, y, z) coordinates of the target T can be obtained through the use of two formulations for each coordinate. For example, the y coordinate for the target T can be determined using both formulations (2) and (5). If the resulting y coordinate values computed using the two formulations differ by more than some acceptable tolerance value, $\varepsilon_y$, then a determination can be made that the matching process failed to resolve the offset between projections in the different sensors with sufficient accuracy, and as result that the candidate pixels do not correspond in that they do not receive projections from the same target T. In the event of a failure of the y computations to match, another iteration of the matching process may be performed in an effort to make an improved selection of candidate pixels within the sensors that each corresponds to a selected target T. It will be appreciated that the computed y values are unlikely to be equal since the different perspective projections onto different sensors can differ due to parallax effects, for example. Therefore, an acceptable tolerance value is prescribed according to the intended application. For surgical imaging applications, an $\varepsilon$ of 0.1-0.3 mm typically offers an acceptable Q3D accuracy. A person of skill in the art may define different acceptable tolerance levels without departing from the spirit of this invention.

Given the assumed sensor symmetry around the x and y axes, persons skilled in the art will appreciate that the same kind of determination can be made for the x coordinates of the target T using formulations similar to those in (2) and (5), but using $n_{xi}$ instead of $n_{yi}$. Formulations (3) and (6) cannot be used part of 402.5 and 402.6 because they require knowledge of the z coordinate. However, the essence of modules 402.5 and 402.6 is to determine the correct target projections on the planes of sensors $S_{11}$, $S_{12}$ and $S_{13}$. For this purpose formulations (2) and (5), adjusted for x and y axes, are sufficient. The complete set of coordinates (x, y, z) is computed part of modules 403 and 404, as described below.

Example of Determining Target's Physical z Location

As illustrated in FIG. 19, in accordance with modules 403 and 404, an initial estimate for the z coordinate, $z_0$, is used to initiate the computation process, This initial value is defined automatically, according to the medical application. The medical application defines the intended world view to be visualized. The initial value $z_0$ starts at the edge of the field of view closest to the endoscope. Referring to FIG. 8, for a Q3D application involving surgical endoscopy, $z_0$ can be 1-5 mm off the distal end 208 of the Q3D endoscope 202, for example. Such initial estimate generally is sufficient for this application as it is unlikely to have any tissues or surgical instruments reside in such close proximity to the Q3D endoscope. Next, value $z_0$ is plugged into formulations (3) and (6). Given that the x coordinate of the target is unique, if $z_0$ were the true and correct z coordinate of the target then formulations (3) and (6) would yield identical values, or approximately equal, within an acceptable level of tolerance, $\varepsilon_x$.

$$|x_{(3)} - x_{(6)}| < \varepsilon_x \quad (7)$$

If (3) and (6) are outside an acceptable tolerance $\varepsilon_x$, then the iteration continues and a new estimate for z is tried, $z_1$.

In accordance with some embodiments, the new estimate is defined automatically. For example, $z_1 = z_0 + \Delta$, where $\Delta$ is the size of the iteration step. In general, at $k^{th}$ iteration $z_k = z_{k-1} + \Delta$. The iterative process stops when condition (7) is met. A smaller $\Delta$ yields increased accuracy in determining the correct target coordinates, but it would also require more computational time to complete the process, hence an increased latency. An increased latency may result in delays between surgical instrument movement and its visualization by the operating surgeon. In other words, the surgeon may perceive the system as lagging behind commands. For a surgical viewing space of 20-30 cm of depth, a $\Delta$ of 0.1-0.3 mm may be sufficient. Of course, a person skilled in the art would know to balance the size of $\Delta$ against the computational required to complete the iterative process.

The above explanation has been simplified for presentation reasons and, therefore, it included only three sensors, $S_{11}$, $S_{12}$, and $S_{13}$. In general, more sensors can be used to increase the accuracy of Q3D coordinate computations but also to reduce the overall number of iterations. For example, if more than three sensors are used, preferably an array of 3×3 sensors, then methods such as the steepest gradient may be employed to trend the direction of estimation errors made by modules 402.5 and 403. The iterative step size and direction can then be adjusted to match the progression towards the local extreme of the 3D error gradient surface.

Guiding Endoscopic Surgery with Q3D Information

Figure 20:
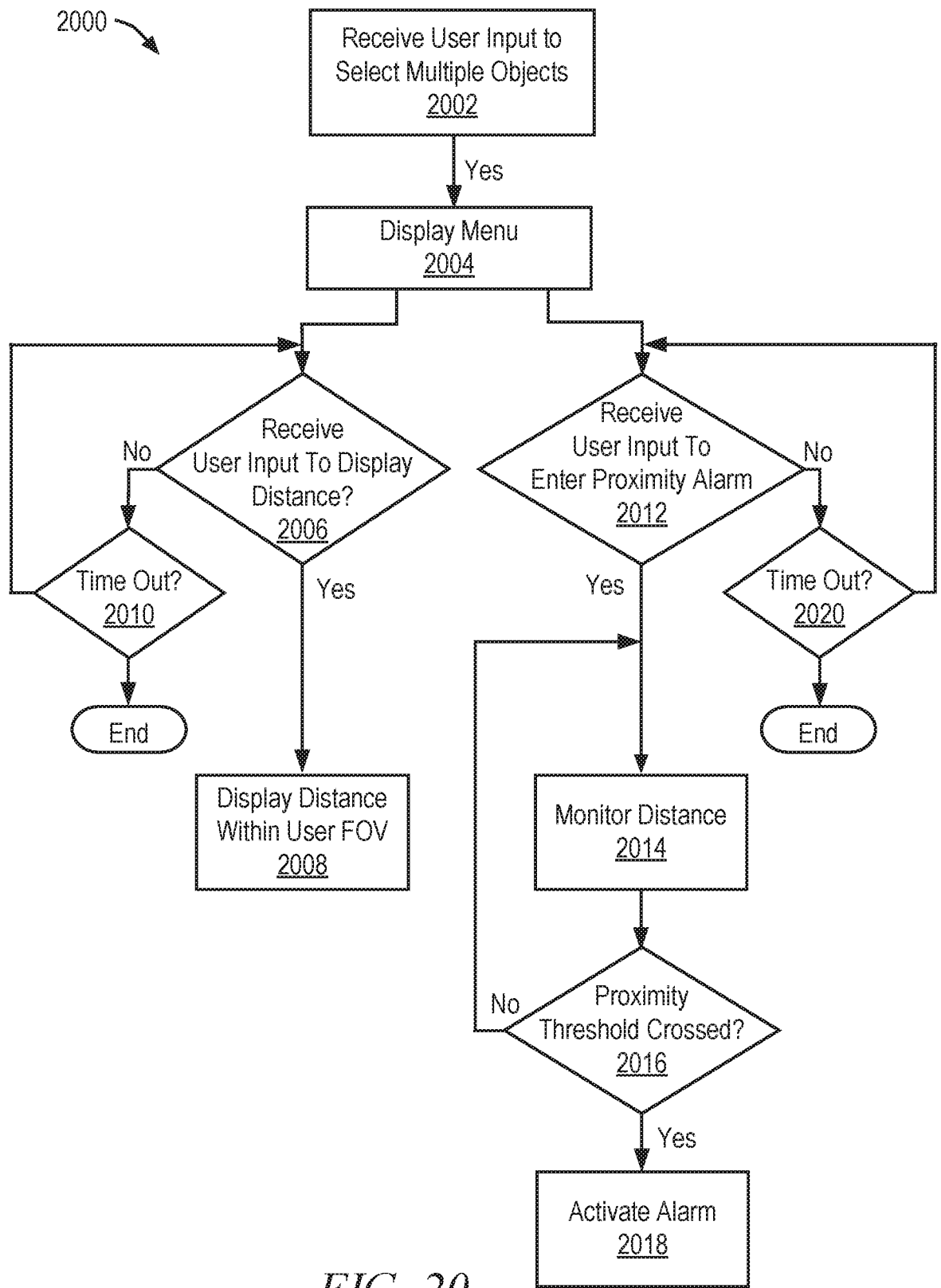
FIG. 20 is an illustrative flow diagram representing a first process to use Q3D information during a surgical procedure in accordance with some embodiments.

FIG. 20 is an illustrative flow diagram representing a first process 2000 to use Q3D information during a surgical procedure in accordance with some embodiments. Computer program code configures the computer 151 to perform the process 2000. Module 2002 configures the computer to receive user input to select at least two objects within a surgeon's field of view when looking into the viewer 312. Module 2004 configures the computer to display a menu on a computer console in response to receipt of a user selection. Decision module 2006 configures the computer to determine whether user input to the menu is received to display a distance. In response to a determination that user input is received to display a distance, module 2008 configures the computer to display a numerical distance within the video image in the surgeon's field of view. Decision module 2010 configures the computer to wait for a prescribed time interval for receipt of user input to select distance display and to end operation of decision module 2006 in response to no receipt of user input within a "time out" interval.

Decision module 2012 configures the computer to determine whether user input to the menu is received to enter a proximity alarm limit. In response to a determination that user input is received to enter a proximity threshold, module 2014 configures the computer to use Q3D information to monitor proximity between two or more objects within the surgeon's field of view. Decision module 2016 determines Whether the proximity threshold has been crossed. In response to a determination that the proximity threshold has been crossed, module 2018 configures the computer to activate an alarm. The alarm may include a sound, a visual queue such as a blinking light, locking of instrument movement to avoid collision, or other haptic feedback. In response to a determination that the proximity threshold has not been crossed, control flows back to monitoring module 2014. Decision module 2020 configures the computer to wait for the prescribed time interval for receipt of user input to enter the proximity threshold and to end operation of decision module 2012 in response to no receipt of user input within the "time out" interval.

Figure 21:
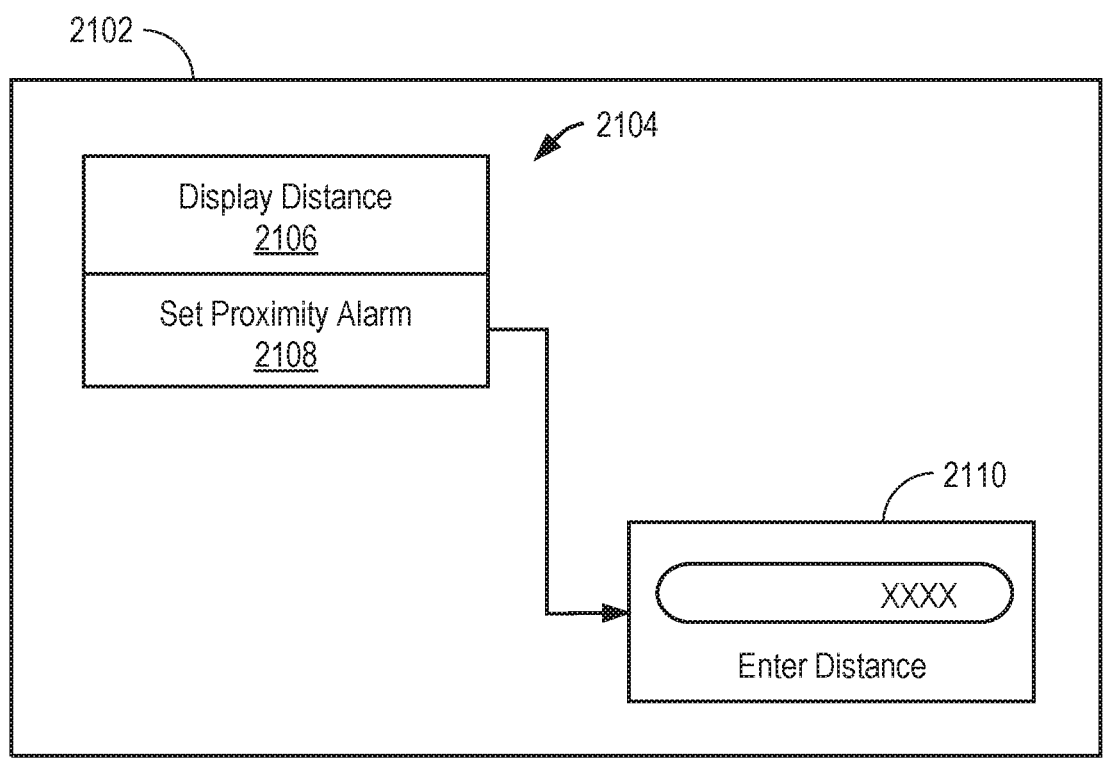
FIG. 21 is an illustrative drawing showing menu selections displayed on a display screen in accordance with the process of FIG. 20 in accordance with some embodiments.

FIG. 21 is an illustrative drawing showing menu selections displayed on a display screen 2102 in accordance with the process of FIG. 20 in accordance with some embodiments. The display screen 2102 includes a viewing monitor associated with the computer 151. Alternatively, the display screen 2102 may include a region of the viewing elements 401R, 401L of the viewer 312. In response to user input, module 2004 causes the display of a menu 2104 that includes a first menu item "Display Distance" 2106 and a second menu item "Set Proximity Alarm" 2108. In response to user input to select the "Display Distance" menu item 2106, module 2008 causes a display of Q3D distance between two or more objects. Referring again to FIG. 4, there is shown a display of a Q3D distance "d_Instr_Trgt" between an instrument 400 and target displayed using module 2008. In response to user input to select the "Set Proximity Alarm" menu item 2108, an "Enter Distance" UI input 2110 is displayed that includes a field in which a user can enter a proximity distance threshold value, e.g., one cm. In an alternative embodiment (not shown), a default proximity threshold may be set in advance for all instruments, and a user may change the proximity threshold using the menu of FIG. 21, for example. In the alternative embodiment, a user can choose to elect the default threshold value rather than enter a threshold value. In some embodiments, a user can select both to display the distance and set a proximity alert.

Figure 22A:
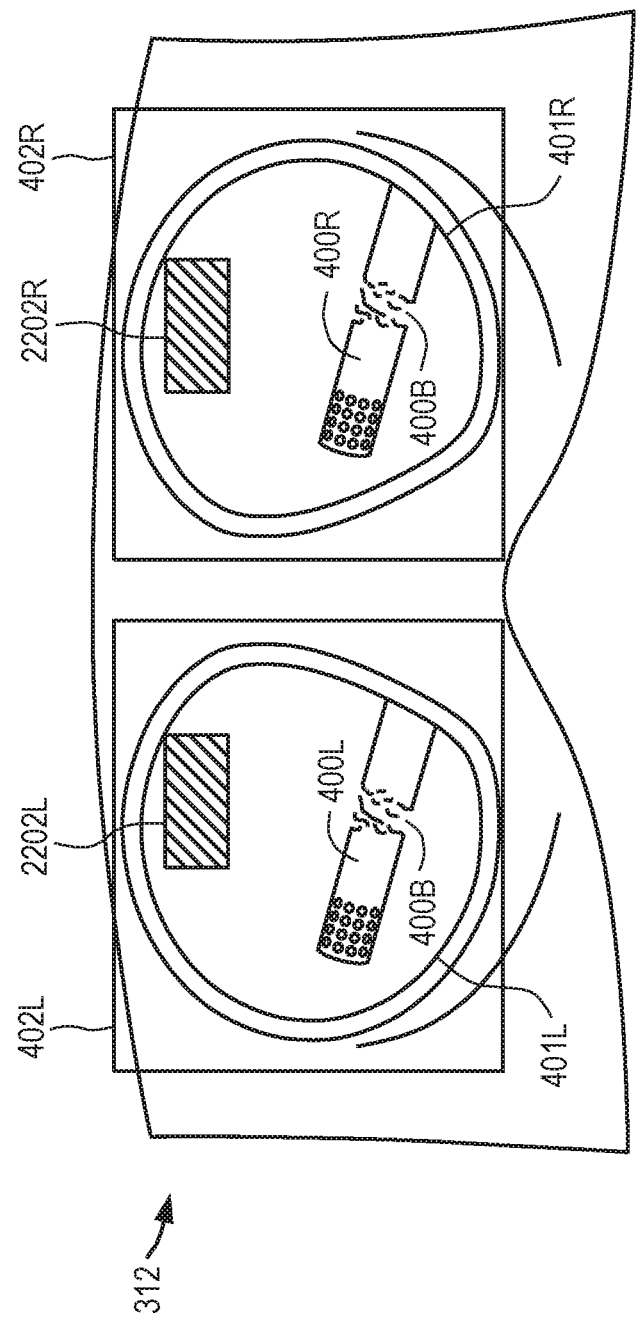
FIGS. 22A-22B are illustrative drawings representing certain details of receiving user input in accordance with the process of FIG. 20 in accordance with some embodiments.
Figure 22B:
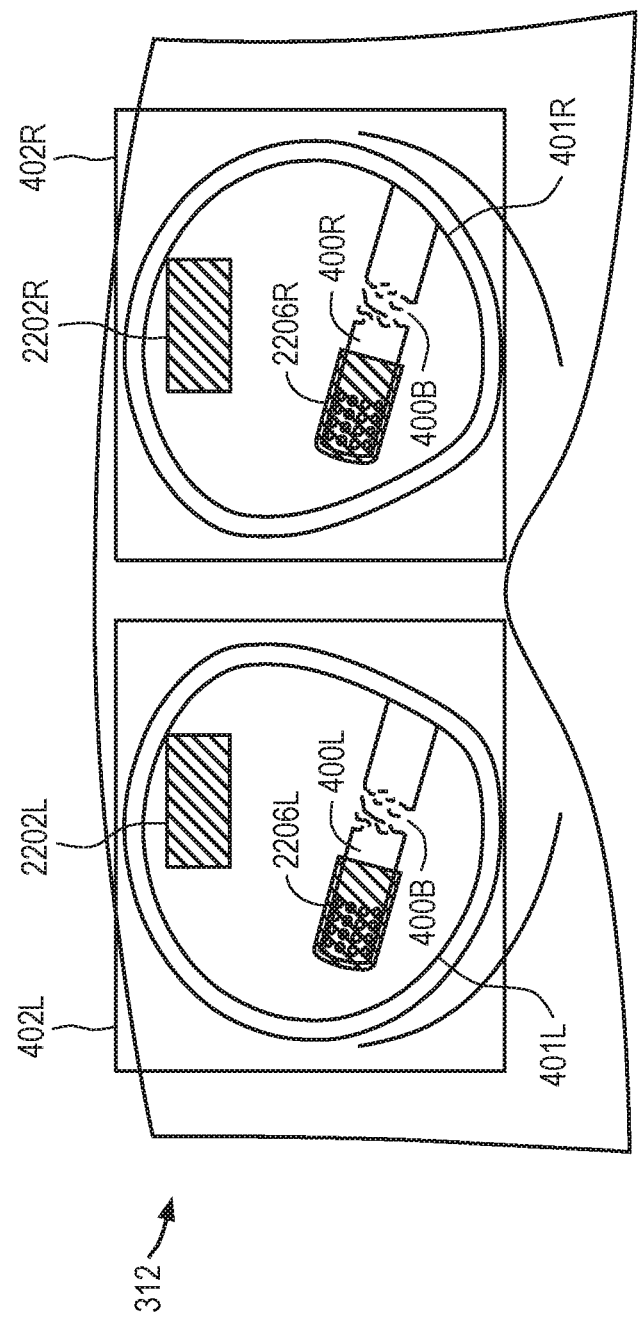

FIGS. 22A-22B are illustrative drawings representing certain details of receiving user input in accordance with the process of FIG. 20 in accordance with some embodiments. FIG. 22A shows example first highlighting areas 2202L, 2202R of a target 410L, 410R, such as body tissue, which can be created using video marker tool, such as telestration, or using the surgeon console manipulating control input devices 160 of FIG. 4. FIG. 22B shows example second highlighting areas 2206L, 2206R of an instrument tip 400L, 400R, which can be created using the video marker tool. In operation in accordance with some embodiments, a user creates the first highlighting areas 2202L, 2202R. Next, the user creates second highlighting areas 2206L, 2206R of the instrument tip 400L, 400R using video marker tool. It will be understood that the order in which items are highlighted is unimportant. The user then actuates a selector (not shown) (e.g., press the ENTER key) to enter the selection. Module 2002 interprets the received user input as selection of the target image 410L, 410R and the instrument image 400L, 400R.

Figure 23:
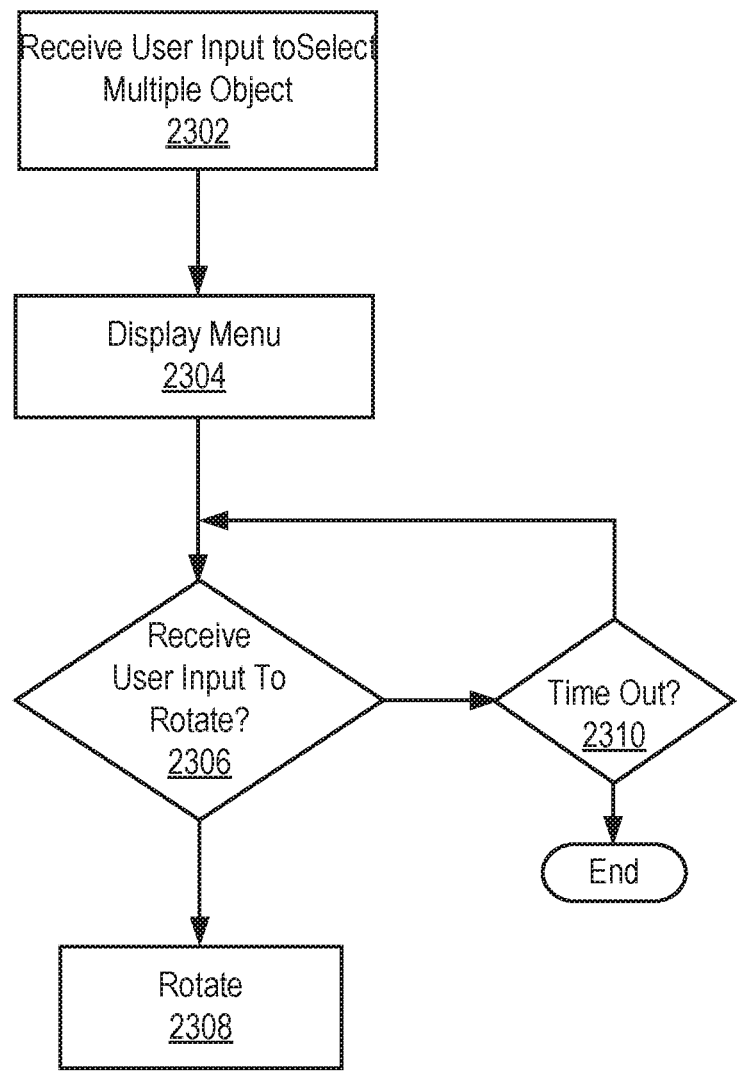
FIG. 23 is an illustrative flow diagram representing a second process to use Q3D information during a surgical procedure in accordance with some embodiments.

FIG. 23 is an illustrative flow diagram representing a second process 2300 to use Q3D information during a surgical procedure in accordance with some embodiments. Computer program code configures the computer 151 to perform the process 2300. Module 2302 configures the computer to receive user input to select an object within a surgeon's field of view when looking in to the viewer 312. For example, referring again to FIG. 22A, user input is shown received to create the second highlighting areas 2206L, 2206R of the instrument tip 400L, 400R using the video marker tool. User input (not shown) is received to actuate a selector (not shown) (e.g., press the ENTER key) to enter the selection of the image of the instrument tip 400L, 400R.

Returning once again to FIG. 23, in response to receipt of a user selection, module 2304 configures the computer to display a menu on a computer console. Decision module 2306 configures the computer to determine whether user input to the menu is received to rotate an image of a selected object. In response to a determination that user input is received to rotate an image, module 2308 configures the computer to display rotate the image to show a different three-dimensional perspective of the object. Decision module 2310 configures the computer to wait for a prescribed time interval for receipt of user input to rotate an image and to end operation of decision module 2306 in response to no receipt of user input within a "time out" interval.

Figure 24:
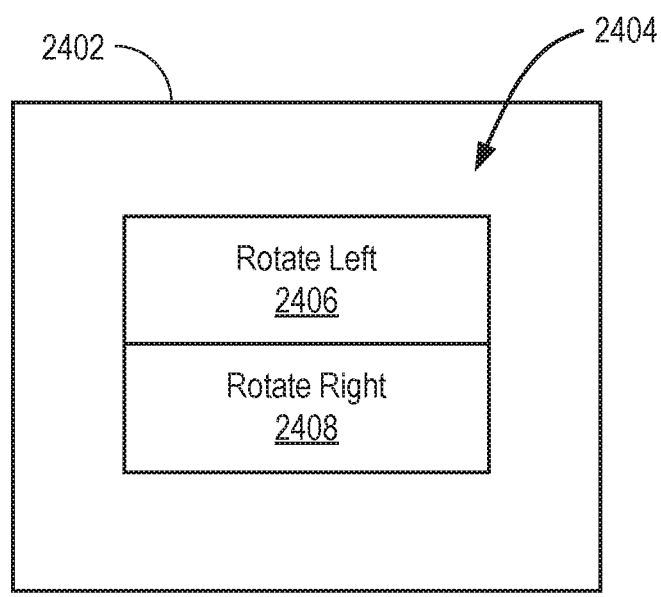
FIG. 24 is an illustrative drawing showing menu selections displayed on a display screen in accordance with the process of FIG. 23 in accordance with some embodiments.

FIG. 24 is an illustrative drawing showing menu selections displayed on a display screen 2402 in accordance with the process of FIG. 23 in accordance with some embodiments. The display screen 2402 includes a viewing monitor associated with the computer 151. Alternatively, the display screen 2402 may include a region of the viewing elements 401R, 401L of the viewer 312. In response to received user input, module 2304 causes the display of a menu 2404 that includes a third menu item "Rotate Left" 2406 and a fourth menu item "Rotate Right" 2408. In response to user input to select one or the other of the third or fourth menu items 2406, 2408, module 2308 uses the causes a rotation of the 3D model created and stored pursuant to module 407 of FIG. 9. It will be appreciated that the amount of rotation may be limited to a few degrees, less than 30 degrees for example, since the sensor imager array 210 has a limited overall field of view.

Haptic Feedback Provided by a Q3D Endoscopy System

Haptics generally describes touch feedback, which may include kinesthetic (force) and cutaneous (tactile) feedback, as well as vibration and movement. In manual minimally invasive surgery (MIS), surgeons feel the interaction of the instrument with the patient via a long shaft, which eliminates tactile cues and masks force cues. In teleoperation surgery systems, natural haptic feedback is largely eliminated because the surgeon no longer manipulates the instrument directly. An objective of haptic technology in teleoperated minimally invasive surgical systems is to provide "transparency", in which the surgeon does not feel as if he is operating a remote mechanism, but rather that his own hands are contacting the patient. Another way to describe this idea is as haptic telepresence. Typically, this requires artificial haptic sensors on the patient-side device to acquire haptic information, and haptic displays on the surgeon side to convey the sensed information to the surgeon. Kinesthetic or force feedback systems typically measure or estimate the forces applied to the patient by the surgical instrument, and provide resolved forces to the hand via a force feedback device. Tactile feedback can be used to provide information such as local tissue deformation and pressure distribution across a tissue surface. Tactile feedback can be used, for example, to simulate palpation in Which a surgeon uses fingertips to detect local mechanical properties of tissue such as compliance, viscosity, and surface texture, which are indications of the health of the tissue. See, Okamura A. M., "Haptic Feedback in Robot-Assisted Minimally Invasive Surgery," Current Opinion in Urology, 2009, Vol. 19 (1), pp. 102-107.

Deformation of a tissue structure having known stiffness can be determined as a function of force imparted to it, and conversely, force imparted to a tissue structure having a known stiffness can be determined as a function of tissue structure deformation. The shape of a human body tissue structure deforms during surgery in response to motion induced by a surgeon. Soft tissue deformation can be approximated in terms of linear elasticity, and a contact force resulting in tissue deformation can be approximated based upon resulting tissue deformation. In general, a tissue structure may be delimited into a set of finite elements of similar size. Decomposition of a tissue volume into tetrahedral elements can be a preferable approach due to shape irregularity of anatomical models. Thus, a configuration of a target tissue structure can be modeled by decomposing it into a set of polygonal (e.g., tetrahedral) elements.

In general, tissue deformation is related to force according to the following formulation:

$$[K]u = f \quad (8)$$

where [K] is the stiffness matrix and is symmetric, positive, definite, and sparse; u is a displacement field; and f is the external forces. The size of this matrix is 3N×3N where N is the number of mesh vertices. If at least some level of tissue isotropy is assumed, then matrix K can be expressed as an N×N matrix.

More particularly, external forces applied to a surface of a deformable object based upon deformation of the object can be determined based upon the following formulation in which the force required to obtain a displacement u* of the deformable object can be determined in accordance with the following formulation:

$$\begin{bmatrix} K & \overline{K} \\ \overline{K}^T & 0 \end{bmatrix} \begin{bmatrix} u \\ \lambda \end{bmatrix} = \begin{bmatrix} f \\ u^* \end{bmatrix} \quad (9)$$

where [K] is a matrix composed of vectors $e_i$ with a 1 in the $i^{th}$ position and zeros elsewhere. The system results from the Lagrange multipliers method which is used for the imposition of specified values for the solution variables. Variational formulation and Lagrange multipliers can be used to minimize: $\frac{1}{2}u^T Ku - u^T f$. The values $\lambda_i$ of [λ] obtained after solving the system are equal to the opposite of the forces that need to be applied at the degree of freedom $u_i$ in order to impose the displacement $u_i = u_i^*$. See, Cotin, S. et al. "Real-time elastic deformations of soft tissues for surgery simulation", *IEEE Transactions on Visualization and Computer Graphics (Impact Factor: 1.9), 01/1999; 5:62-73. DOI: 10.1109/2945.764872*, which is incorporated herein in its entirety by this reference. Tissue stiffness values are known or readily can be determined. For example, McKnight A. L., et al. "MR elastography of breast cancer: preliminary results," *Am. J. Roentgenology*, 2002;178:1411-1417, Uffmann K., et al. "In vivo elasticity measurements of extremity skeletal muscle with MR elastography," *NMR in Biomedicine*, 2004;17:181-190 and Tay B. K., et al. "In vivo mechanical behavior of intra-abdominal organs," *IEEE Transactions on Biomedical Engineering*, 2006;53:2129-2138, which are expressly incorporated herein by this reference, provide reports of tissue stiffness for various tissue structures. Their data and others can be used to determine matrix [K], as suitable for force computations according to Eq. (8).

FIG. 25 is an illustrative flow diagram representing a process 2500 to use Q3D information to determine haptic feedback in accordance with some embodiments. The process 2500 can employ one or more of system 152 and Q3D endoscopic system 101C. The system 152 of FIG. 5 or 6, in conjunction with Q3D endoscopic system 101C of FIG. 8, computes the force vector, f, exerted by the instrument onto tissues according to formulations (8) or (9). The stiffness matrix [K] may comprise known values of tissue stiffness. Once computed, the force exerted by the instrument onto tissue may be displayed or used to drive a haptic interface device.

Referring to FIG. 25, module 2502 captures Q3D information of a surgical scene and that is used to produce a Q3D model of the scene. The example scene includes a tissue structure and a surgical instrument. Module 2504 identifies and registers a surgical instrument within the scene. Module 2506 uses Q3D information to determine displacement u of tissue about the instrument as the instrument is urged with some force against a surface of a tissue structure within the scene. Module 2508 obtains appropriate tissue stiffness matrix information [K] for a tissue type of the tissue structure within the scene. Module 2510 uses the determined tissue displacement information u and the tissue stiffness matrix information to determine a force f. Module 2512 overlays a visual display within a surgeon's field of view within the surgical scene of the determined force f. Module 2514 actuates a haptic interface to provide to a surgeon haptic feedback that is indicative of the determined displacement u and the determined force f.

Figure 26:
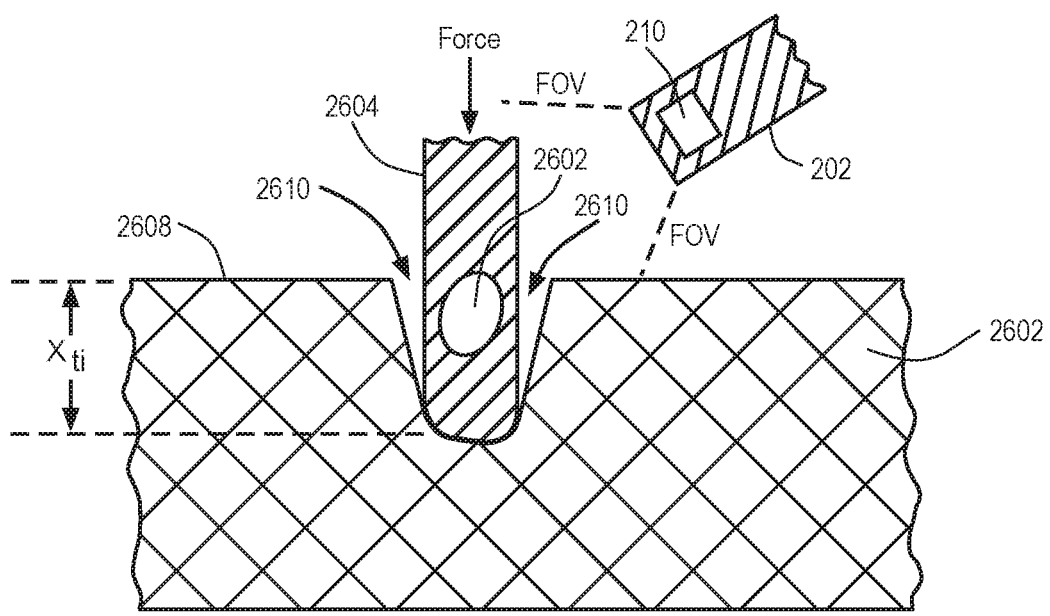
FIG. 26 is an illustrative drawing showing a tissue structure contacted by an end a surgical instrument and a Q3D endoscope in accordance with some embodiments.

FIG. 26 is an illustrative drawing showing a tissue structure 2602 contacted by an end effector portion of a surgical instrument 2604 and an endoscope 2606 having an image sensor 210 array disposed to have a field of view (FOV) to capture Q3D image information for the contact between the tissue structure 2602 and the instrument 2604 in accordance with some embodiments. It will be understood that the endoscope also is used to capture stereoscopic visual images viewable by a surgeon during a surgery. During a teleoperation surgical procedure, a surgeon views a surgical scene through the stereoscopic display device 164 while manipulating control input devices 160 shown in FIG. 5 to maneuver an end effector portion of an instrument into contact with a surface of a target tissue structure. The surgeon controls motion of the instrument so as to impart a force to a location on the tissue surface that causes deformation of the tissue surface contour at the location.

The Q3D information is used to quantify the level of haptic feedback to be provided to the surgeon so that the feedback is indicative of the deformation of and/or of the force applied to the tissue surface 2608 by the instrument 2604. More particularly, dimensions of displacement 2610 tissue surface 2608 determined using the Q3D information is used to generate haptic feedback. Assuming that the tissue structure, or at least a subregion of interest, has a substantially uniform stiffness, a larger displacement deformation is indicative of the surgical instrument applying a larger force. According to Eq. (8), for a known stiffness matrix K, using the displacement u measured by the Q3D endoscopic system 101C of FIG. 8, the force vector f applied to tissue by the instrument 2604 of FIG. 26 can be computed or approximated. Similarly, from force vector f, the resistance presented by tissue can be computed or approximated. Such information may be useful for tissue palpation applications. Therefore, in accordance with some embodiments, haptic feedback indicative of a larger deformation and/or a larger force, or tissue softness, can be provided to the surgeon. Conversely, a smaller displacement deformation can be indicative of the surgical instrument applying a smaller force, or of tissue presenting increased stiffness, and in accordance with some embodiments, haptic feedback indicative of a smaller deformation and/or a smaller force, or higher tissue stiffness, can be provided to the surgeon.

A tissue structure 2602 may not have uniform stiffness. Localized subsurface structures embedded within the tissue structure, such as a tumor or blood vessel that have a stiffness that is different from the stiffness of the tissue structure, can alter the local stiffness of a tissue structure. A localized subsurface structure shall be referred to herein as an "anomaly". The presence of an anomaly may influence the local displacement deformation of a tissue structure in response to a force applied by an instrument to a tissue surface location that overlays the anomaly. In other words, the displacement deformation of a tissue surface location that overlays a subsurface anomaly in response to an amount of force will be different from the displacement deformation at a different tissue surface location that does not overlay a subsurface anomaly in response to the same amount of force. Thus, as a result of such variations of tissue structure stiffness, application of substantially the same force to different locations of a tissue structure can result in different deformations at those different locations. The different deformations can be indicative of the presence of a subsurface anomaly.

In order to resolve for the variability of the tissue stiffness matrix K, the surgeon may have to tap the instrument against a neighboring tissue structure known to be free of anomalies. This is an achievable goal, because it is customary to identify the location of anomalies by using pre-procedure imaging. Such images can direct the surgeon towards an anomaly-free neighboring region. When instrument 2604 is tapped against the region comprising the anomaly, the Q3D endoscopic system 101C provides quantitative information about a smaller-than-expect amount of displacement u. Consequently, a relative map of tissue stiffness can be obtained. Alternatively, if instrument 2604 of FIG. 26 is equipped with a force sensor (not shown), a tissue stiffness map can be computed or approximated based on Eq. (8). The force sensor provides the force vector f, and the Q3D endoscopic system 101C provides the displacement u. If f and u are measured at sufficiently many points within the region of interest, the elements of stiffness matrix K can be computed or approximated. For example, assuming tissue isotropy and symmetry, matrix K has up to $N*(N+1)/2$ distinct elements. Therefore, displacement u and force vector f should be measured at up to $N*(N+1)/2$ locations in order to fully characterize matrix K. In accordance with some embodiments, haptic feedback indicative of the different tissue structure displacements at different tissue surface locations is provided to the surgeon.

Haptic User Interfaces

As used herein, the term "haptic user interface" refers to a user interface that provides haptic information to a user. There are many different kinds of haptic interfaces. For example, as described herein, a shape display, also referred to as a tangible user interface, can act as a haptic interface that provides haptic information indicative of a shape or contour of an object. A haptic user interface may provide haptic information through mechanical stimulation through selective extension and retraction of pins or though variable intensity of vibration, for example. A haptic user interface may provide haptic information through variable intensity electrical stimulation, for example.

Figure 27A:
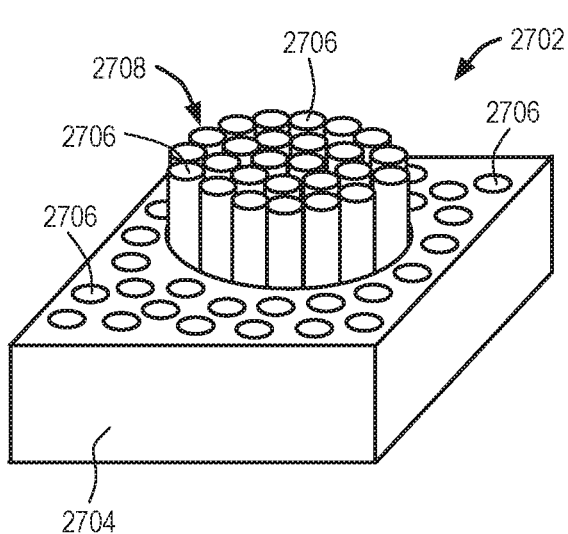
FIGS. 27A-27C are illustrative drawings representing a first embodiment of a tangible user interface (TUI) that acts as a shape display suitable to provide haptic feedback in accordance with some embodiments.
Figure 27B:
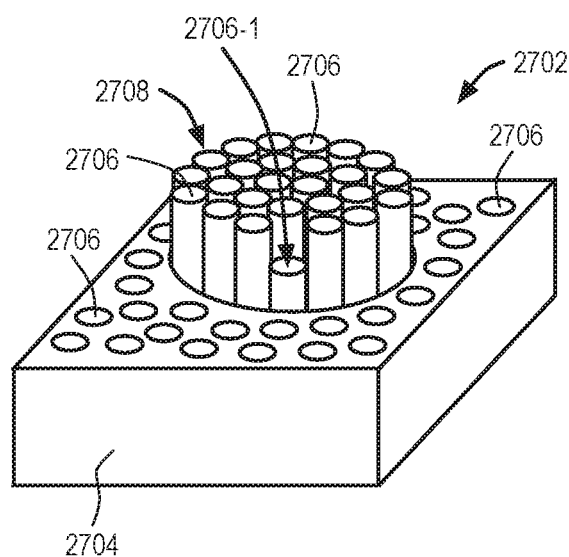
Figure 27C:
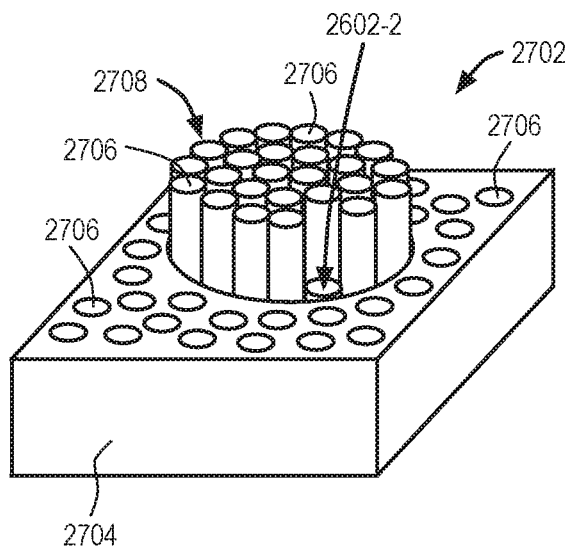

FIGS. 27A-27C are illustrative drawings representing a first embodiment of a haptic user interface in the form of a tangible user interface (TUI) 2702 that acts as a shape display suitable to provide haptic feedback in accordance with some embodiments. The TUI 2702 includes a housing structure 2704 that houses a plurality of pins 2706 that can be selectively displaced outwardly from the housing. FIG. 27A shows the first embodiment of the TUI with a multiplicity of pins displaced outwardly to create a three-dimensional model 2708 of a tissue structure visible within a surgical scene viewable through the viewer 312 of FIG. 4. The configuration of pins shown in FIG. 27A corresponds to an initial TUI state in the absence of feedback indicating deformation of a tissue structure. The three-dimensional model 2708 of the tissue structure produced by the first embodiment of the TUI 2702 in its initial state represents the tissue structure at rest in the absence of surface forces that would deform its shape. FIG. 27B shows the first embodiment TUI with a pin 2706-1 at a first (x, y) location displaced inwardly (downward, as shown), relative to the pin's initial state position, by a first amount. FIG. 27C shows the first embodiment TUI with a second pin 2706-2 displaced inwardly, relative to the second pin's initial state position, TUI by a second amount that is different from the first amount.

Figure 28A:
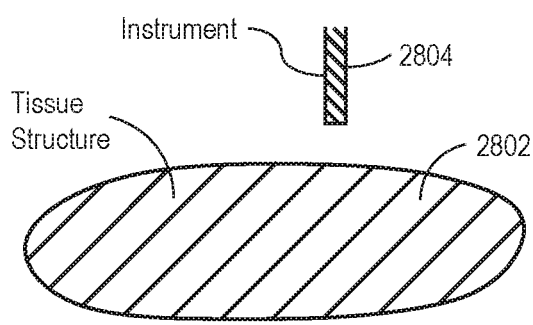
FIGS. 28A-28C are illustrative drawings representing a tissue structure having its shaped deformed by a force applied by a surgical instrument.
Figure 28B:
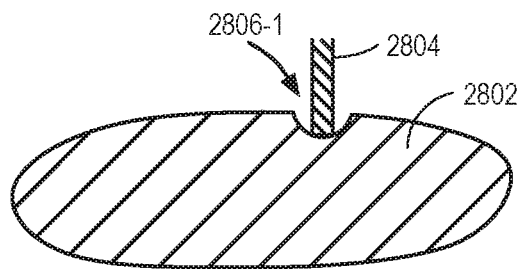
Figure 28C:
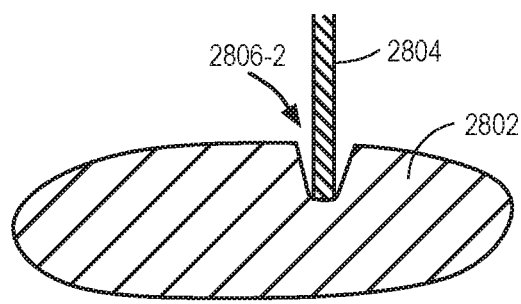

FIGS. 28A-28C are illustrative drawings representing a tissue structure 2802 having its shape deformed by a forces applied by a surgical instrument 2804. FIG. 28A shows the tissue structure 2802 in its natural at rest state with the instrument 2804 disposed so as to not contact the tissue structure. FIG. 28B shows the instrument 2804 contacting the tissue structure at a first tissue structure location with a force sufficient to cause deformation 2806-1 of the tissue structure by a first displacement amount. FIG. 28C shows the instrument contacting the tissue structure at a second tissue structure location with a force sufficient to cause deformation 2806-2 of the tissue structure by a second displacement amount. Referring again to FIGS. 27A-27C, the first embodiment of the TUI 2702 includes an array of axially aligned pins 2706 that are arranged in a Cartesian (x, y) plane. Each pin is associated with an (x, y) location in the array. The pins are moveable axially between an at rest position and variable degrees of raised displacement. When all pins 2706 are at rest, i.e., no axial displacement, their heads (tops) define a flat, planar (x, y) surface within the housing 2704. Each pin 2706 is associated with its own actuator (not shown) such that each pin can be axially raised, lowered, or raised and lowered independently by controllable variable displacement amounts. In accordance with some embodiments, in an initial state, a multiplicity of pins are arranged to create a three-dimensional model of a tissue structure 2708. Variations in pin displacement relative to the initial state three-dimensional model provide haptic feedback that indicates corresponding changes in shape of the modeled tissue structure. The three-dimensional model produced using the first embodiment TUT is geometrically sized so that a surgeon can interact with the model in a manner similar to the manner in which a surgeon would palpate an actual tissue structure during a medical procedure. The shape of the TUI tissue model 2708 is changed in response to deformation of the surface of the tissue structure 2802 of FIGS. 28A-28C caused through contact with an instrument 2804 that is under teleoperative control of the surgeon to thereby provide a surgeon with haptic feedback indicative of the deformation of the tissue structure viewed though the viewer 312 in the course of a surgical procedure. Follmer S. et al., "inFORM: Dynamic Physical Affordances and Constraints through Shape and Object", *Actuation, UIST* '13, October 8-11, St. Andrews, UK, disclose a 2.5 D shape display that uses a shape display to provide haptic feedback, and such a TUI apparatus can be modified to function as described herein. For example, the TUI 2702 can be driven by the Q3D endoscopic system 101C according to the stiffness matrix K which was computed or approximated as explained above. As a consequence, the surgeon would be provided with, at least, relative information about tissue stiffness and allowed to perform indirect or virtual tissue palpation.

As another example, a surgeon manipulates a surgical instrument so as to provide a substantially constant force to various locations on a tissue structure. The constant force applications can be regulated, such as by using a sensor and visible gauge, or by setting a. teleoperated manipulator to apply a force until a threshold force level is sensed. Alternatively, the applications can be done by using the surgeon's perceived feel. The Q3D endoscope captures the location of the force application and a measure of tissue deformations at the various tissue locations in response to the substantially constant force applications. The relationship of equation (8) can be used to determine different tissue stiffnesses at the different locations in response to the substantially constant force applications, and then the locations and stiffnesses are mapped to a haptic TUI. The haptic interface provides surgeon feedback indicative of the different tissue stiffnesses at the different locations so as to produce a virtual palpation output to the surgeon. The surgeon can then trace a finger or hand along a path over the TUI and sense the changing stiffness along the path to palpate the simulated tissue structure, in a manner similar to a surgeon's action over real tissue.

In accordance with some embodiments, the tissue stiffness matrix K, or stiffness map, can be mapped to (x, y) locations of individual TUI pins 2706. In other words, physical locations the (x, y) location of a given pin 2706 is mapped to a location on the surface of the tissue structure 2802. Assume for the purposes of this example that the TUI pin 2706-1 at the first (x, y) location in FIG. 27 is mapped to the first tissue structure location 2806-1 in FIG. 28B and that the TUI pin 2706-2 at the second (x, y) location in FIG. 27C is mapped to the second tissue structure location 2806-2 in FIG. 28C.

Assuming the TUI 2702 has W×L pins, the Q3D model of the tissue surface tissue structure 2802 can be meshed onto a W×L grid. Each node of the mesh would then correspond to a TUI pin. Given that the Q3D model provides the actual width ($W_{tissue}$) and length ($L_{tissue}$) of the tissue surface of interest, the corresponding (x, y) coordinate of a pin with TUI location counts $N_W$ and $N_L$ can be computed as ($N_W$/W*$W_{tissue}$, $N_L$/L*$L_{tissue}$). Conversely, for a known Q3D model point of coordinates (x, y) the TUI location counts of the corresponding TUI pin can be computed as $N_X$=x*W/$W_{tissue}$ and $N_Y$=y*L/$L_{tissue}$. The mapping is stored in a non-transitory, computer-readable storage device (not shown). A multiplicity of pins 2706 of the TUI 2702 are raised outwardly (upward, as shown) so as to produce the three-dimensional model 2708 the tissue surface contour of the tissue structure 2802, or at least a region of interest of the tissue structure.

The surgical instrument is registered with the mapped tissue surface locations. In other words, the kinematic location of the instrument 2804 relative to mapped locations of the tissue surface of the tissue structure 2802 is registered and updated throughout the surgical procedure. The registration, for example, may be achieved by identifying the target instrument in the FOV of the Q3D endoscope using identification algorithms similar to those described in FIGS. 9 and 10. Thus, due to the registration of the instrument 2804 and the mapping between the tissue locations and TUI locations, each contact between the instrument 2804 and a surface location of the tissue structure 2804 can be mapped to one or more TUI pin locations. Moreover, the image sensor array 210 captures Q3D information for each contact between the instrument and the tissue surface, that can be used to determine deformation displacement of the tissue surface due to the contact. The Q3D information, in turn, is used to determine an amount of change in outward displacement of one or more pins 2706, mapped to the contacted tissue surface location, in response to the contact by the instrument.

For example, FIG. 27A shows an example posture of the first embodiment TUI 2702 at rest, when as shown in FIG. 28A, a surgeon has moved the instrument adjacent to the tissue structure but has not used the instrument to actually contact the tissue structure. FIG. 27B and FIG. 28B illustrate haptic feedback in the surgeon's manipulation of the instrument to cause a deformation the first tissue location 2806-1 shown in FIG. 28B results in the pin 2706-1 at the first (x, y) location to move inwardly relative to its initial state position. The amount of inward displacement of the pin 2706-1 at the first (x, y) location is determined based upon the first displacement amount, as measured using the Q3D endoscopic system 101C, by which the first tissue location 2806-1 in FIG. 28B is displaced by the instrument. Similarly, FIG. 27C and FIG. 28C illustrate haptic feedback in the surgeon's manipulation of the instrument 2804 to cause a deformation the second tissue location 2806-2 shown in FIG. 27C results in the TUI pin 2706-2 at the second (x, y) location to move inwardly relative to its initial state position. The change in outward displacement of the pin 2706-2 at the second (x, y) location is determined based upon the second displacement amount by which the second tissue location 2806-2 in FIG. 28C is displaced by the instrument.

Alternatively, the tissue deformation sensed as Q3D information can be registered with kinematic information that identifies the pose of the instrument tip (e.g., kinematic information that identifies the pose of a kinematic arm that holds the instrument). The combined tissue deformation information and instrument tip position and orientation information is then mapped to the TUI to create a haptic interface that allows the surgeon to palpate the simulated tissue structure.

Figure 29A:
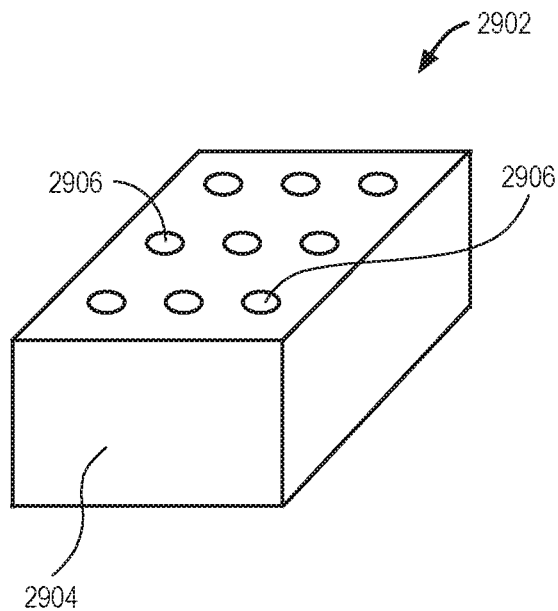
FIGS. 29A-29C are illustrative drawings representing an alternative embodiment tangible user interface (TUI) that acts as a shape display suitable to provide haptic feedback in accordance with some embodiments.
Figure 29B:
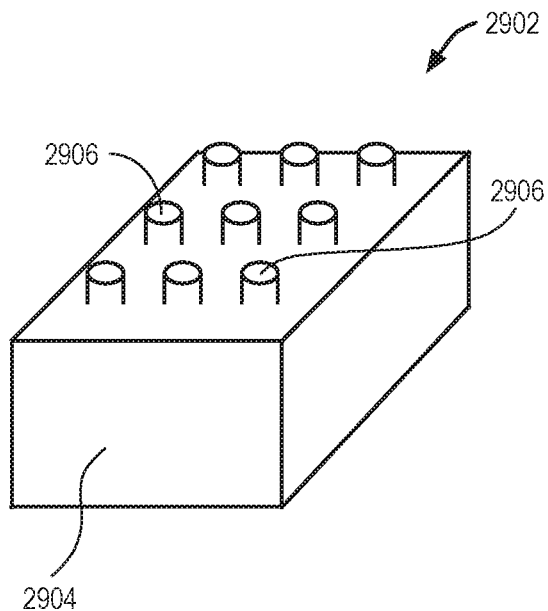
Figure 29C:
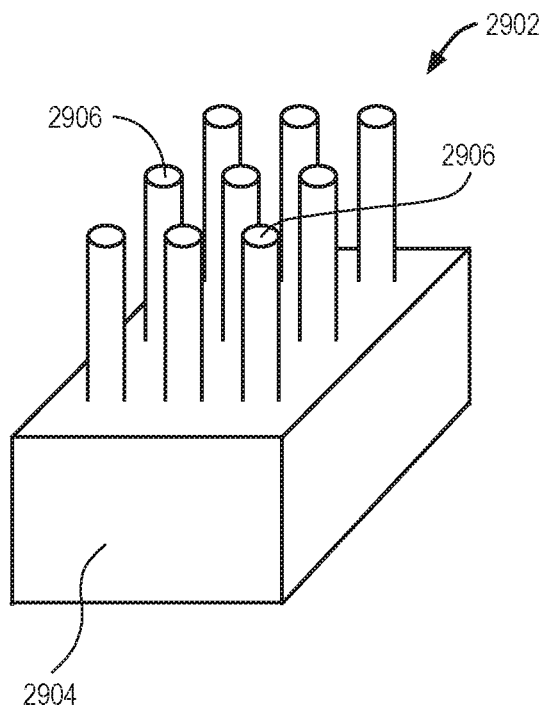

FIGS. 29A-29C are illustrative drawings representing an alternative embodiment haptic user interface in the form of a tangible user interface (TUI) 2902 that acts as a shape display suitable to provide haptic feedback in accordance with some embodiments. The alternative TUI embodiment 2902 includes a housing 2904 structure that houses a plurality of axially aligned pins 2906 that can be outwardly (upward, as shown) displaced by variable amounts in response to displacement of a tissue surface. FIG. 29A shows the alternative TUI 2902 at rest with no pins 2906 raised. FIG. 29B shows the alternative TUI 2902 with pins 2906 raised by a first amount. FIG. 29C shows the alternative TUI 2902 with pins 2906 raised by a second amount, larger than the first amount. In general, the pin configuration of the alternative embodiment TUI 2902 of FIGS. 29A-29C is analogous to that of the TUI 2702 of FIGS. 27A-27C. However, the alternative embodiment TUI 2906 is smaller and is geometrically sized for mounting on a surgeon's fingertip. Examples of such an alternative TUI 2906 are known. Killebrew J. H., et al., "A Dense Array Stimulator to Generate Arbitrary Spatio-Temporal Tactile Stimuli," Journal of Neuroscience Methods, 2007, Vol. 161 (1), pp. 62-74, disclose a 400-probe stimulator to generate arbitrary spatio-temporal stimuli "on the fly" to the skin. Each probe includes an individual motor to control its axial displacement. Moy G., et al., "A Compliant Tactile Display for Teletaction," Proceedings of ICRA in Robotics and Automation, 2000, *IEEE*, Vol. 4, discloses a one-piece, pneumatically actuated tactile display molded from silicone rubber. Howe, Robert D., et al., "Remote Palpation Technology", *IEEE Engineering in Medicine and Biology*, May/June, 1995, disclose a tactile shape display that uses shape metal alloy wires as actuators due to their high power to volume and high power to weight and force to weight ratios.

Similar to the TUI 2702 of FIGS. 27A-27C, the shape of a TUI surface represented by heads of the pins 2906 of the alternative embodiment TUI 2902 of FIGS. 29A-29C is changed in response to deformation of the tissue structure surface caused through contact with an instrument that is, for example, under teleoperative control of the surgeon. However, unlike the TUI 2702 of FIGS. 27A-27C, the alternative embodiment TUI 2902 of FIGS. 29A-29C pin locations of the alternative embodiment TUI are not mapped to tissue surface locations. Rather, haptic feedback produced by outward displacement of pins 2906 of the alternative embodiment TUI 2902 is mapped to a location of the tissue surface that is contemporaneously visible through the stereo display device 164 and that is currently contacted by the surgical instrument under the surgeon's control. For example, the center point of TUI 2702 is mapped to correspond to the instrument tip, so that as the instrument tip moves, the changing haptic sensation occurs centered on TUI 2906. The surgeon places a finger on TUI 2702 in order to perceive the change. The amount of haptic feedback provided by such alternative TUI 2902 correlates to the computed or approximated tissue displacement provided by the Q3D endoscopic system 101C or to the force vector f, as computed or estimated using Eq. (8).

In alternative instance, one instance the pins are initially displaced axially outward by a predetermined distance, and the pins are driven to attempt to remain at this distance. A default stiffness is set, so that the finger when pressed against the tops of the pins displaces the pins slightly downward while the pins are driven to return to their default level. Thus, the pins feel "squishy". As the instrument traverses tissue and encounters one or more changes in stiffness, the change in stiffness is transferred to the TUI so that tissue with increased stiffness is felt at the TUI as less "squishy" (pins displaced axially toward the finger), and tissue with decreased stiffness is felt as more "squishy" (pins displaced axially away from the finger). In this way the instrument tip functions as a remote palpation instrument, with the palpation sensation transferred to the TUI. Likewise, in an alternative embodiment the pins are initially set at an axial displacement flush with the TUI surface (see e.g., FIG. 29A, and tissue with decreased stiffness is felt at the TUI as stiffer (pins displaced axially toward the finger).

Figure 30:
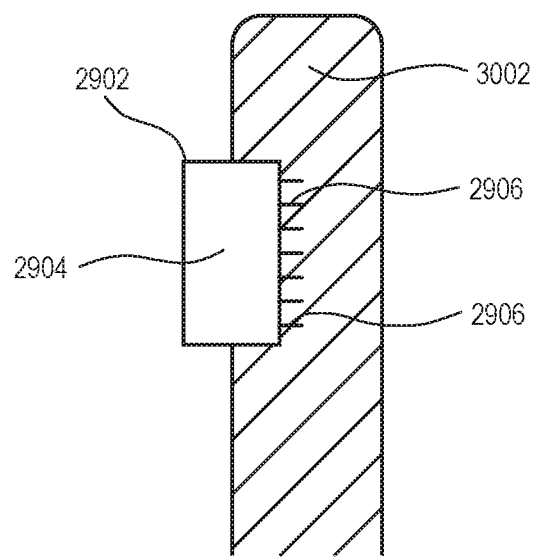
FIG. 30 is an illustrative drawing showing the alternative embodiment TUI mounted on the finger of a surgeon in accordance with some embodiments.

FIG. 30 is an illustrative drawing showing an alternative embodiment TUI 2902 mounted on the finger 3002 of a surgeon in accordance with some embodiments. When mounted, the alternative embodiment TUI 2902 is oriented so that when pins 2906 are outwardly displaced in response to a tissue displacement of the tissue surface, the pins 2906 press against the surgeon's fingertip 3002. In accordance with some embodiments, different pin displacement amounts are indicative of different tissue displacements of a currently contacted portion of a tissue surface, or of different amounts of force applied by the instrument to the currently contacted portion of a tissue surface.

Referring now to both FIGS. 28A-28C and FIGS. 29A-29C, FIG. 29A shows an example posture of the alternative embodiment TUI 2902 at rest, when as shown in FIG. 28A, a surgeon has moved the instrument 2804 adjacent to the tissue structure 2802 but has not used the instrument to actually contact the tissue structure. FIG. 29B shows an interface surface shape produced using the pins 2906 of the alternative embodiment TUI 2902 in which a plurality of pins 2906 are raised by a displacement amount that is determined based upon the first tissue displacement amount, so as to provide a first stimulus level to a user contacting the pins, by which the first tissue location 2806-1 in FIG. 28B is displaced by the instrument 2804. FIG. 29C shows an interface surface shape produced using the pins 2906 of by the alternative embodiment TUI 2902 in which a plurality of pins 2906 are raised by a displacement amount that is determined based upon the second tissue displacement amount, so as to provide a second stimulus level to a user contacting the pins, by which the second tissue location 2806-2 in FIG. 28C is displaced by the instrument 2804. It can be seen that the tissue displacement amounts at the first and second tissue locations 2806-1, 2806-2, are different, and accordingly, TUI pin displacement amounts in response to the first and second tissue displacements also are different.

Those of skill in the art would know to substitute the use of pins with other forms of haptic stimulation. For example, instead of stimulating a surgeon's finger 3002 using mechanically actuated pins abutting against hand or finger grips, for example, sub-threshold electricotactile stimulation may be provided. Such systems would use safe levels of electrical currents, just slightly above the human perception level, modulated by the magnitude of tissue displacement u, or tissue force f, as provided by the Q3D endoscopic system 101C. Such other forms of haptic stimulation are known. For example, Kaczmarek et al., "Maximal Dynamic Range Electrotactile Stimulation Waveforms", *IEEE Transactions on Biomedical Engineering*, Vol. 39, No. 7, July 1992, have presented techniques and waveforms for suitable electrotactile stimulation which is incorporated herein in its entirety by this reference. In alternative embodiments, the operating surgeon may be provided with haptic feedback that vibrates or provides manipulating resistance to the control input device 160 of FIG. 5. The amount of vibration or manipulating resistance would be modulated according to the magnitude of tissue displacement u, or tissue force f, as provided by the Q3D endoscopic system 101C of FIG. 8. Suitable implementations are known, such as described in U.S. Pat. No. 6,594,552 B2 (filed Apr. 6, 2000) and U.S. Pat. No. 8,561,473 B2 (filed Mar. 30, 2009) show the use of a control input device with tactile feedback and are incorporated herein in their entirety by this reference.

Transformation of Q3D Information to Haptic Feedback

Figure 31:
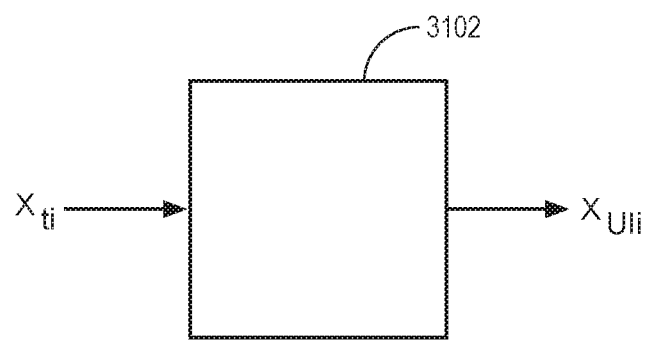
FIG. 31 is an illustrative computational block configured to determine haptic feedback as a function of tissue surface deformation in accordance with some embodiments.

FIG. 31 is an illustrative computational block 3102 configured to determine haptic feedback as a function of tissue surface deformation in accordance with some embodiments. In accordance with some embodiments, haptic feedback is provided through variable pin axial displacement. Alternatively, for example, electrical stimulation or vibration stimulation may be used to provide haptic feedback. The computer 151 of FIG. 5 can be configured to implement the computational block. Q3D information collected using the image sensor array 210 includes information that includes an indication of a measure of vertical deformation distance $X_{ti}$ at a certain time for an individual tissue surface location. The computational block receives information indicative of the deformation distance $X_{ti}$ as input, and the block 3102 produces as output one or more pin displacement amounts $X_{UTi}$ as a function of the deformation distance $X_{ti}$. Although Q3D endoscopes using an image sensor array are discussed herein, other types of Q3D endoscopes may be used without departing from the spirit of this invention. For example, Q3D endoscopes that use time-of-flight sensors can be used with equal performance. U.S. Pat. No. 8,262,559 B2 (filed Apr. 9, 2009), incorporated in its entirety by reference, describes at least one example of such alternative Q3D endoscopes.

Figure 32:
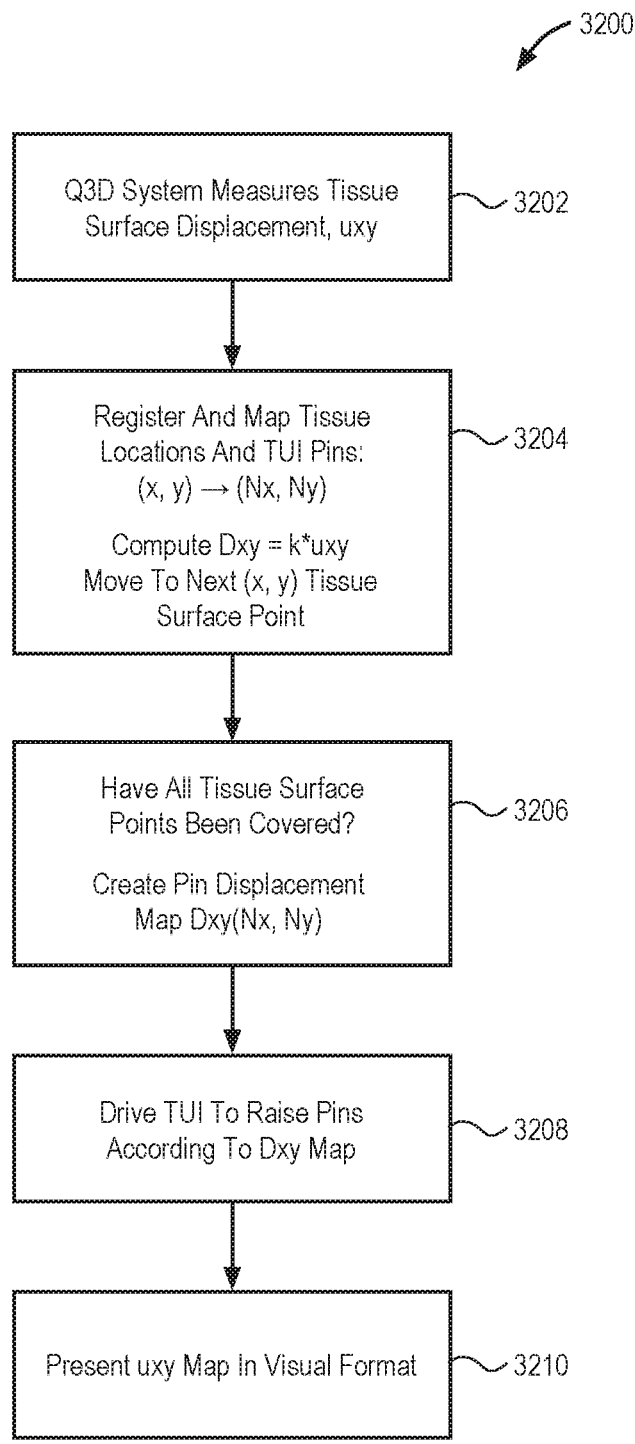
FIG. 32 is an illustrative flow diagram representing a process performed using the computational block of FIG. 31 in accordance with some embodiments.

FIG. 32 is an illustrative flow diagram representing a process 3200 performed using the computational block of FIG. 31 in accordance with some embodiments. At module 3202, the Q3D endoscopic system computes the 3D coordinates of the displacement u of tissue surface 2608 of FIG. 26, for example, which is deformed by instrument 2604. The 3D coordinate computations are carried according to elements and modules described in FIGS. 8-19. At module 3204, the 3D coordinates of tissue displacement u are mapped to pin location counts and pin displacements. For example, assuming that the tissue surface point (x, y) has a measured displacement $u_{xy}$, the pin with location counts $N_X$ and $N_Y$, computed as described, is driven to displace its height by $D_{xy}$. The relationship between D and u may be proportional, based on estimated range of tissue displacement and on TUI construction details. For example, if the tissue is estimated to deflect in a range of up to 20 mm, the relationship between D and u may be 1:1. The TUI pin would then change is height by 1 mm for each 1 mm of tissue displacement. If the surgical procedure is performed on structures of increased stiffness, a smaller tissue displacement range is used. In such cases, a range of up to 5 mm may be optimal. In order to provide the surgeon with sufficient haptic feedback resolution, the pin displacement D may be computed as 4*u. In other words, for each 0.25 mm of tissue displacement the TUI pin changes is height by 1 mm. Those of skill in the art know how to substitute the use of TUI haptic feedback system with other forms of haptic feedback interfaces. For example, if sub-threshold electric stimulation is used as a form of haptic feedback then the magnitude of the stimulating current is modulated according to the proportional relationship discussed above. Alternatively, if vibrations of control input devices 160 are used as haptic feedback, the acceleration of the vibration or the vibration intensity may be modulated according to the proportional relationship described above. In general, module 3204 of the flow diagram maps displacement $u_{xy}$ to the magnitude of feedback provided the haptic interface used by system 152 of FIG. 5 or 6. At module 3206, the process is iterated to cover all points of the tissue surface of interest in contacted by the instrument 2604 of FIG. 26. At module 3208, the haptic interface is driven to provide feedback according to the computed map. Optional module 3210 may also provide the tissue displacement information in a visual format on any of the displays associated with system 152.

Force Feedback Interface

Referring again to FIG. 26, it can be seen that visual indicia is 2602 overlaid onto the surgical instrument in a surgical scene to provide visual feedback to the user indicative of the amount of force applied by the instrument to the target tissue structure in accordance with some embodiments. Reiley C. E. et al., "Effects of visual feedback on robot-assisted surgical task performance", *The Journal of Thoracic and Cardiovascular Surgery*, January 2008, teach the use of visual markers to provide tactile feedback while tying surgical knots during teleoperation surgery. The visual indicia include a color-coded marker overlaid onto an image of the instrument in a surgical scene. Coloring of the marker changes with amount of force sensed by the force sensors. The marker is colored yellow in response to an ideal amount of applied force. The marker is colored green in response to less than an ideal amount of force applied. The marker is colored red in response to more than an ideal amount of force applied. In operation, a user can use the marker color as a guide to repositioning the instrument as needed to achieve the ideal amount of force. In response to viewing a green marker, the user may reposition the instrument to increase the amount of force. In response to viewing the red marker the user may reposition the marker to reduce the amount of force. Such force feedback interface may be incorporated within system 152 which computes or approximates the amount of force by processing displacement information provided by the Q3D endoscopic system 101C of FIG. 8, as explained above. Alternatively, other types of force feedback interfaces may be used. For example, the amount force applied by the instrument may be displayed in the form of bar graphs or as digital display on the side of viewer 312 of FIGS. 22A and 22B.

Overall Process to Use Q3D Information to Provide Haptic Feedback

Figure 33:
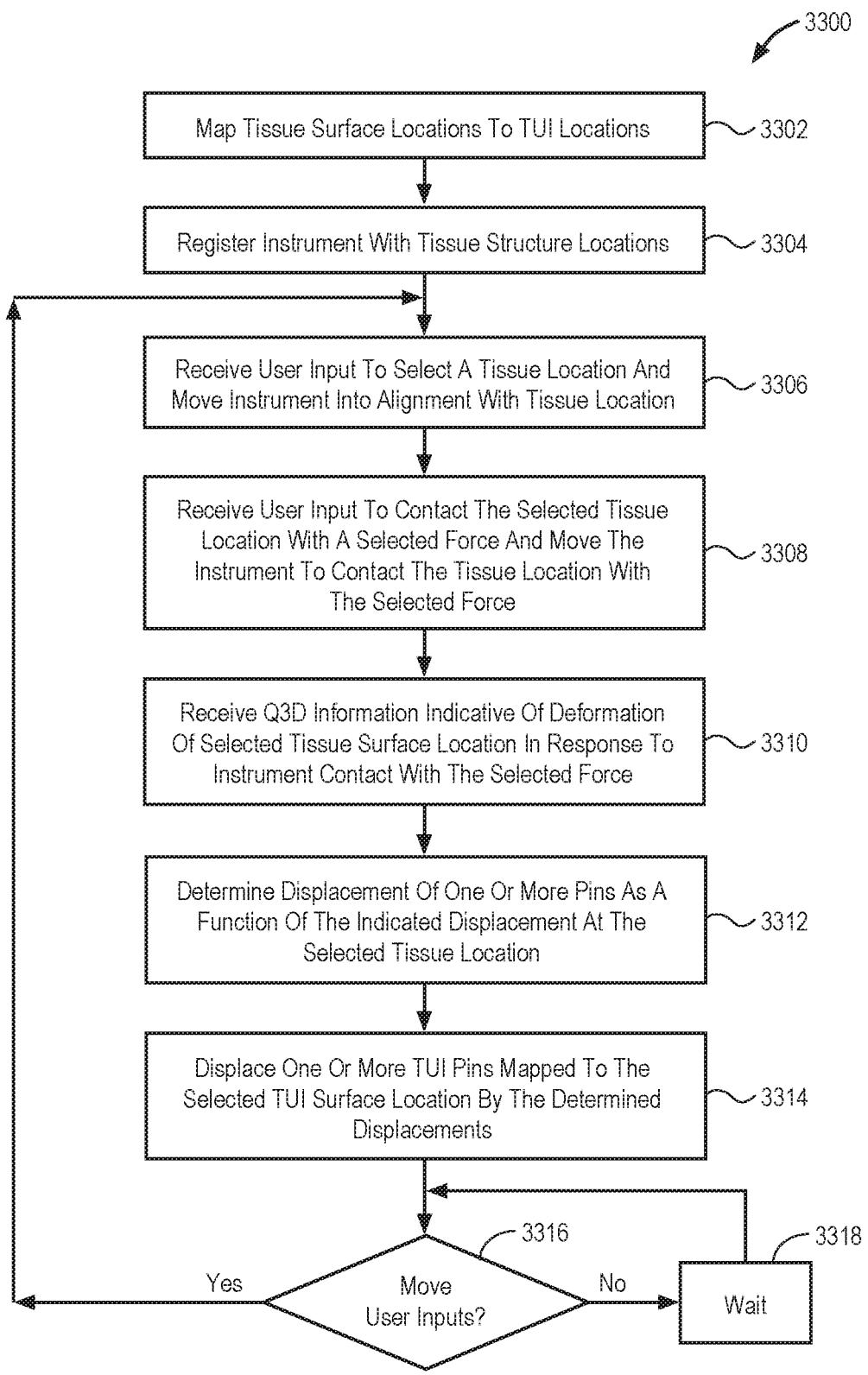
FIG. 33 is an illustrative flow diagram of a first haptic feedback process for use with the TUI of FIGS. 27A-27C in accordance with some embodiments.

FIG. 33 is an illustrative flow diagram of a first haptic feedback process for use with the TUI 2702 of FIGS. 27A-27C in accordance with some embodiments. Module 3302 maps tissue surface locations to TUI locations and stores the mapping in a non-transitory, computer-readable storage device. Module 3304 registers the surgical instrument with the tissue locations. The registration, for example, may be achieved by identifying the target instrument in the FOV of the Q3D endoscope using identification algorithms similar to those described in FIGS. 9 and 10. Module 3306 receives user input to select a tissue surface location and moves the instrument to alignment with the selected tissue surface location. Module 3308 receives user input to impart a selected force and to move the instrument to the contact the selected tissue location and to impart the selected force. Module 3310 receives Q3D information indicative of deformation distance of the selected tissue surface in response to the imparted force. Module 3312 determines an amount of displacement for one or more pins mapped to the selected tissue surface location as a function of the indicated tissue deformation distance at the selected tissue location. Module 3314 effects displacement of the one or more pins mapped to the selected tissue location by the determined amount. Decision module 3316 determines whether new user input is received to change the select a different tissue surface location. If no such user input is received, then module 3318 causes a wait by some prescribed amount after which control again returns to decision module 3316. In response to receipt of user input to select a new tissue surface location, control flows to module 3306. Those of skill in the art know how to substitute the use of TUI haptic feedback system with other forms of haptic feedback interfaces. For example, if sub-threshold electric stimulation is used as a form of haptic feedback then the magnitude of the stimulating current is modulated according to the steps discussed above. Alternatively, if vibrations of control input devices 160 are used as haptic feedback, the acceleration of the vibration or the vibration intensity may be modulated according to the steps described above. Moreover, if visual interfaces are used to provide haptic feedback the visual element providing the feedback (e.g., visual indicia, bar graphs, digital displays, etc.) is modified according to the steps discussed above.

Figure 34:
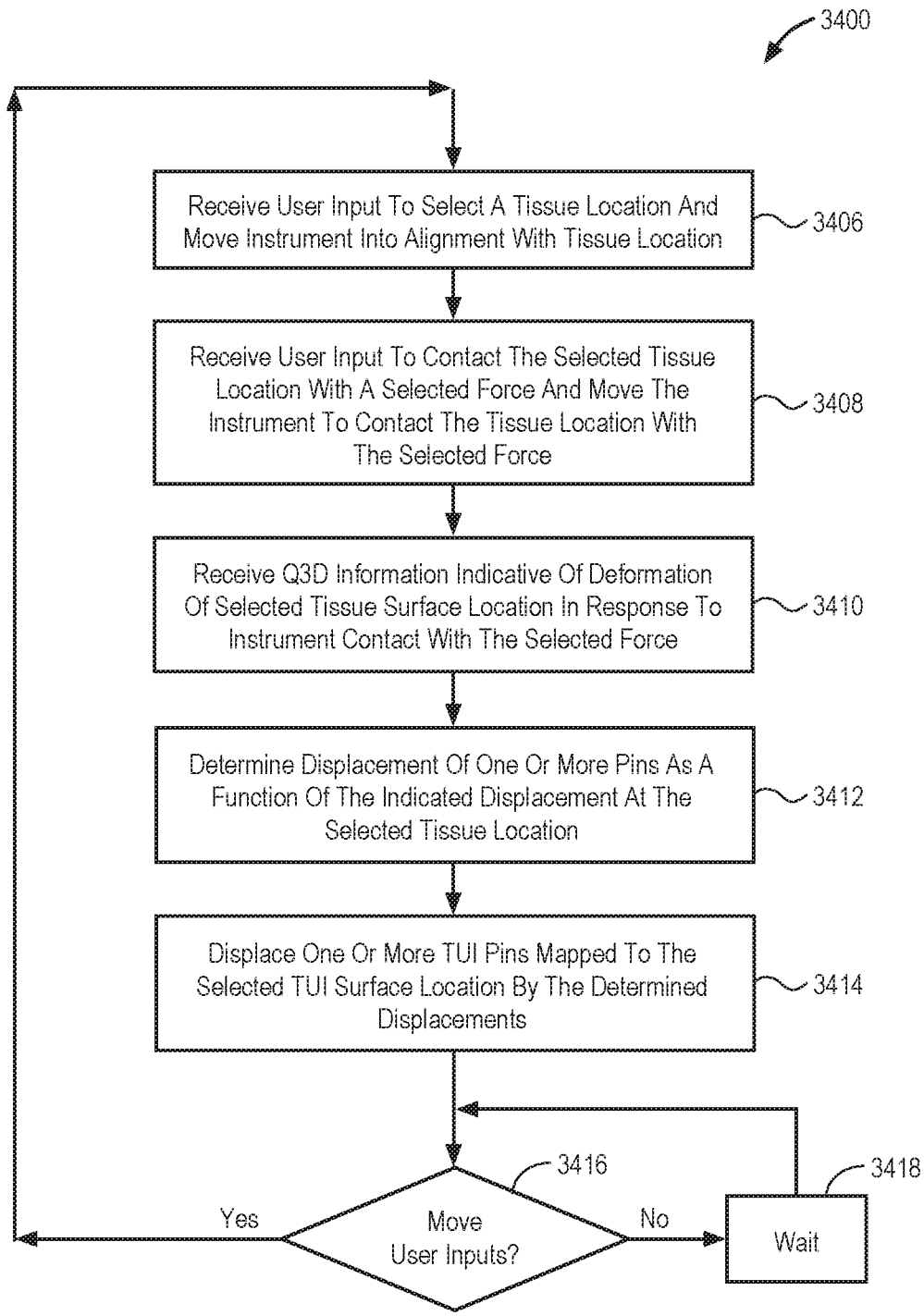
FIG. 34 is an illustrative flow diagram of a second haptic feedback process for use with the alternative embodiment TUI of FIGS. 29A-29C in accordance with some embodiments.

FIG. 34 is an illustrative flow diagram of a second haptic feedback process for use with the alternative embodiment TUI 2902 of FIGS. 29A-29C in accordance with some embodiments. It will be appreciated that first and second haptic processes are similar. Module 3406 receives user input to select a tissue surface location and moves the instrument to alignment with the selected tissue surface location. Module 3408 receives user input to impart a selected force and to move the instrument to the contact the selected tissue location and to impart the selected force. Module 3410 receives Q3D information indicative of deformation distance of the selected tissue surface in response to the imparted force. Module 3412 determines an amount of displacement one or more pins as a function of the indicated tissue deformation distance at the selected tissue location.

Module 3414 effects displacement of the one or more pins mapped to the selected tissue location by the determined amount. Decision module 3416 determines whether new user input is received to change the select a different tissue surface location. If no such user input is received then module 3418 causes a wait by some prescribed amount after which control again returns to decision module 3416. In response to receipt of user input to select a new tissue surface location, control flows to module 3406.

Figure 35:
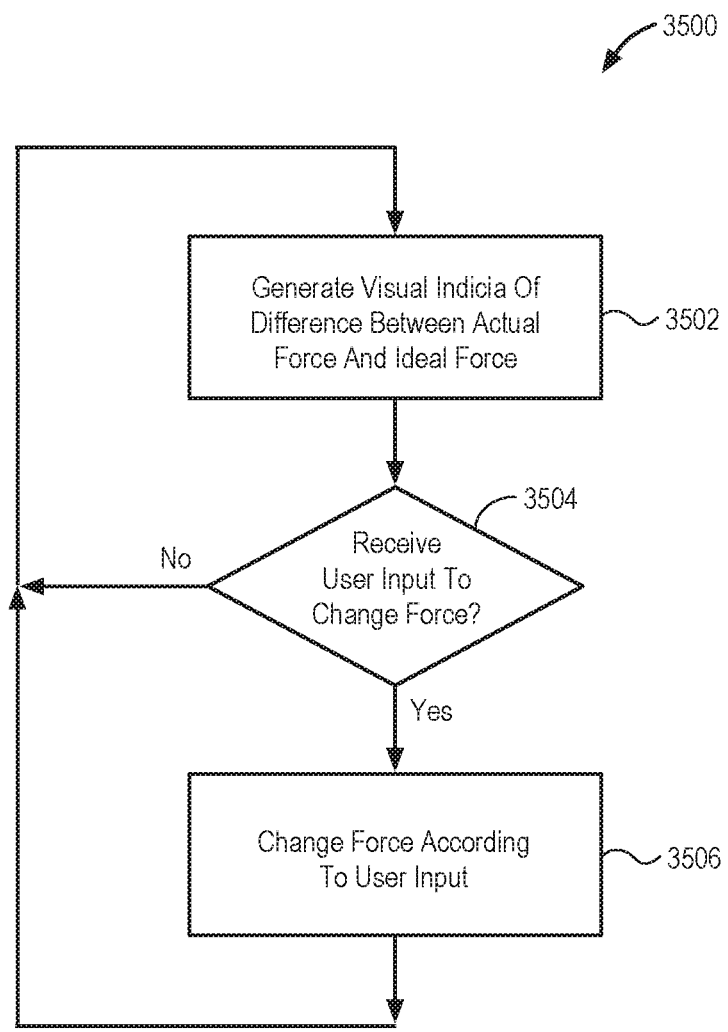
FIG. 35 is an illustrative flow diagram of a third process to control force imparted to a selected tissue surface location in accordance with some embodiments.

FIG. 35 is an illustrative flow diagram of a third process 3500 to control force imparted to a selected tissue surface location in accordance with some embodiments. As explained with reference to FIG. 26, a visual cue 2602 may be provided in a surgical scene to provide an indication of whether to change force imparted to a tissue surface location. The third process may run in parallel with the first or second processes. Module 3502 receives an indication of force sensed using a sensor associated with a tip portion of the instrument and produces within a surgical screen display visual indicia of the magnitude of the sensed force. Decision module 3504 determines whether user input is received to change the amount of force imparted by the instrument. In response to a determination that user input is received to change the amount of force, module 3506 changes the imparted force pursuant to the user input. In response to a determination that no user input is received to change the amount of force, control returns to module 3502.

Q3D-based Haptic Feedback for Virtual Tissue Palpation

FIGS. 36A-36E are illustrative drawings showing a sequence of cross-section views of a surface of a tissue structure 3602 showing deformation of a tissue surface 3608 produced in response to a force applied by an instrument 3604 in accordance with some embodiments. More particularly, these drawings illustrate the implementation of Q3D-based haptic feedback for virtual tissue palpation. In the illustrative sequence, the instrument 3604 contacts and applies a force having a vertical downward component upon a surface 3608 tissue structure 3602. The drawings show deflection of the tissue surface 3608 at multiple discreet locations in response to the force. A Q3D endoscope 202 is shown disposed to capture image information representing the tissue deformation at each of multiple different tissue surface locations. An anomaly 3612 is shown embedded within the tissue structure 3602 beneath the tissue surface 3608. The tissue structure 3602 has a characteristic stiffness, $K_t$. The anomaly 3612 tissue structure has a different characteristic stiffness, $K_a$. Since the anomaly tissue structure 3612 is beneath the surface of the target tissue structure, it is not visible in the image captured using the Q3D endoscope 202. As explained above, stiffness matrices Kt and Ka may be known a priori. In such case, system 152 would be configured to substitute matrix Kt for matrix Ka when instrument 3604 of FIG. 36A travels over the region comprising the anomaly. As presented above, either the user or the system is capable of identifying the transition zone from Kt to Ka based on pre-operative images which show the position of the anomaly relative to the tissue surface. Alternatively, a mechanism to determine or approximate the relative difference in stiffness between the region with the anomaly 3612 and regions free of anomalies may be incorporated in system 152, also as discussed above. In all such cases, system 152 provides the operator with direct, indirect or relative amount of haptic feedback about force exerted by the instrument or about the stiffness presented by tissues.

Figure 36A:
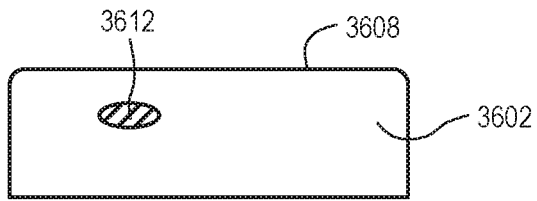
FIGS. 36A-36E are illustrative drawings showing a sequence of cross-section views of a surface of a tissue structure showing deformation of a tissue surface produced in response to a force applied by an instrument in accordance with some embodiments.
Figure 36B:
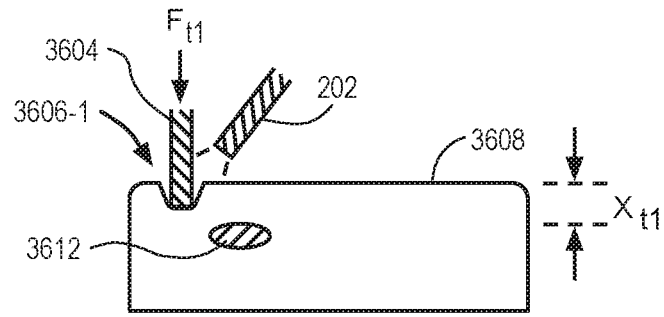
Figure 36C:
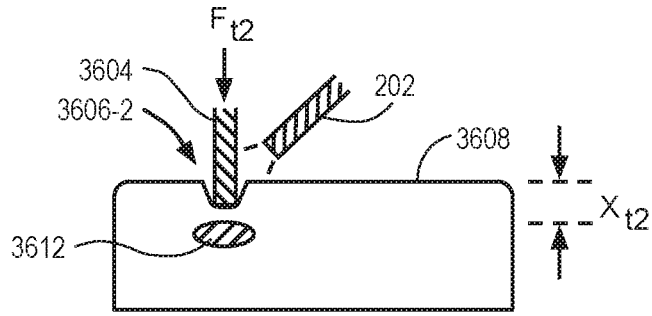
Figure 36D:
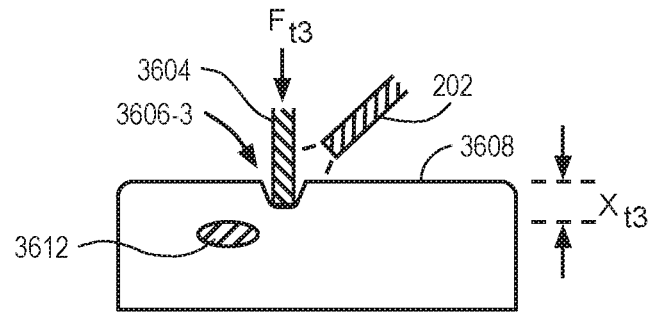
Figure 36E:
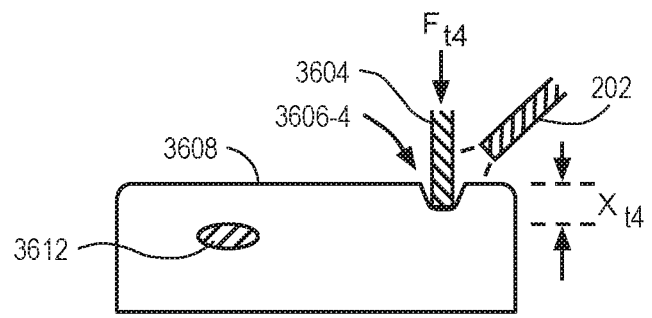
Figure 37A:
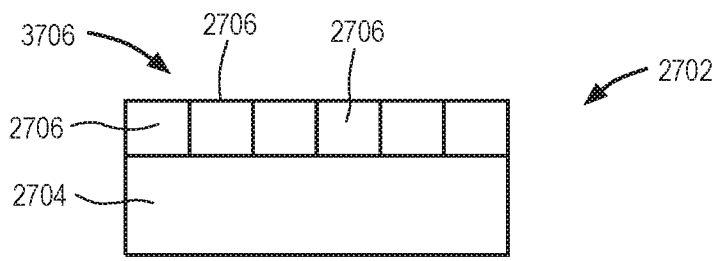
FIGS. 37A-37E are illustrative drawings showing a sequence of cross-section views of the TUI of FIGS. 27A-27C configured to show example "instantaneous" deformations of the TUI pin top surface interface that correspond to example tissue structure deformations shown the sequence of cross-section views of FIGS. 36A-36E in accordance with some embodiments.

FIGS. 37A-37E are illustrative drawings showing a sequence of cross-section views of the TUI 2702 of FIGS. 27A-27C configured to show example "instantaneous" deformations of the TUI pin top surface interface that correspond to example tissue structure deformations shown the sequence of cross-section views of FIGS. 36A-36E in accordance with some embodiments. Referring to FIG. 37A, the TUI 2702 includes a surface structure 3706 with contours that correspond to and mirror deformations formed in the tissue structure surface 3608 in accordance with some embodiments. More particularly, the TUI 2702 includes a shape-changing haptic feedback surface structure 3706 comprising a plurality of pins 2706 that cooperate to change physical shape of the haptic feedback surface 3706 in response to the amount of force exerted by the instrument 3604, to the stiffness presented by tissue structure 3602 or to the amount of tissue deflection measured by the Q3D endoscope. In accordance with some embodiments, the TUI shape changing surface 3706 includes a plurality of vertical pins 2706 that collectively define the TUI surface. Individual pins 2706 are selectively raised and lowered to change the shape of the TUI surface structure. Vertical (axial) positions of the tops of the pins that make up the TUI surface are changed in response to changes in the tissue structures surface contour so that the TUI surface contour continuously matches the tissue structure contour. The TUI surface deformations in FIGS. 37A-37E are referred to as "instantaneous" to connote the notion that they exist substantially contemporaneously with the existence of corresponding tissue structure deformations (i.e., the user experiences no perceivable delay). A given TUI deformation comes into being in response to the occurrence of tissue structure deformation at a corresponding location and disappears in response to a return of tissue structure shape at the corresponding location to its natural shape. Alternatively, the TUI deformation may respond to the amount of force exerted by the instrument or to the amount of stiffness presented by tissue during virtual palpation. Such alternative embodiments of TUIs are implemented using same principles explained in FIGS. 37A-37E.

FIG. 36A shows a first cross-section view of the target tissue structure 3602 prior to contact by the instrument 3604. FIG. 37A shows a corresponding first cross-section view of the contour of the TUI surface 3706 prior to the instrument 3604 contacting the target tissue surface 3608. In order to simplify the following explanation, the outer surface contour of the example tissue structure 3602 is shown to be relatively flat. It will be understood, however, that a tissue structure 3602 may have a naturally curvaceous contour and may have naturally occurring irregularities, such as indentations and bumps.

Figure 37B:
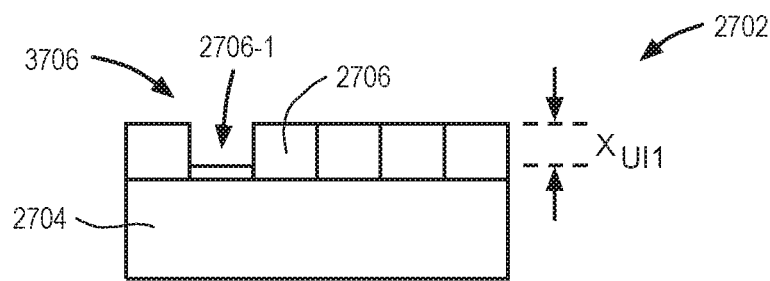

FIG. 36B shows a second cross-sectional view of the tissue structure 3602 in which an instrument 3604 is impressed against the tissue surface 3608 to the left of the sub-surface anomaly 3612 structure so as to apply a force that deforms a first region 3606-1 of the tissue structure 3602. The depth of deformation at the point of contact between the instrument 3604 and the tissue surface at the first surface region 3606-1 is a function of at least force $F_{t1}$ exerted upon the surface at that point of contact and stiffness of the target tissue surface at that point of contact. In the example second cross-sectional view, the lowest point of the deflection within the first region is a vertical distance $X_{t1}$ from adjacent undisturbed regions of the tissue surface 3608. Vertical distance $X_{t1}$ is measured by the Q3D endoscopic system 101C of FIG. 8. System 152 can then compute the corresponding instrument force $F_{t1}$, or estimate the corresponding local tissue stiffness $K_{t1}$, as described above. FIG. 37B shows a corresponding second cross-section view of a contour of the TUI surface 3706 in which a pin in a first region 3706-1 of the TUI surface 3706 is retracted by a first amount $X_{UT1}$ in response to the instrument 3604 deforming the first region 3606-1 of the tissue structure 3602 by the amount $X_{t1}$. Alternatively, the same technique, elements, or steps may be applied to modify the TUI surface in response to $F_{t1}$ or $K_{t1}$. A deformation formed at a first region of the TUI surface 3706-1 that corresponds to the first region of the target tissue surface 3606-1 has a shape that corresponds to shape of the deformation of the first region of the target tissue surface. The shape of the first region of the target surface has returned to its natural contour. The depth of deformation $X_{UT1}$ at the first region of the TUI surface is a function of at least the depth of deformation $X_{t1}$ of the target tissue surface in response to a force applied to the target tissue surface within the first region of the target tissue surface. Alternatively, the depth of deformation $X_{UT1}$ at the first region of the TUI surface may be a function of at least $F_{t1}$ or $K_{t1}$.

Figure 37C:
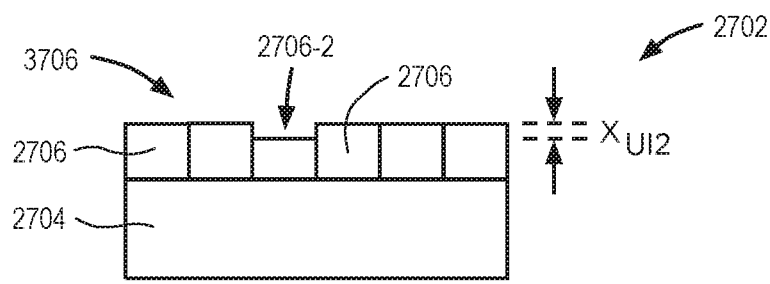

FIG. 36C shows a third cross-section view of the tissue structure 3602 in which the instrument 3604 is impressed against a second region 3602 of the tissue surface above the sub-surface anomaly structure 3612 so as to apply a force that deforms the target tissue surface. In this example, the depth of deformation at the point of contact between the instrument 3604 and the tissue structure 3602 is a function of at least force exerted upon the target surface at the point of contact and stiffness of both the target tissue surface at the point of contact and the subsurface anomaly structure beneath the point of contact. In this example, it is assumed that the anomaly 3612 has a greater stiffness than the target tissue structure 3602. In this example, it is also assumed that the subsurface anomaly structure is close enough to the target tissue surface that its stiffness influences the depth of deflection of the target tissue surface in response to a force applied by the instrument. In the example third cross-sectional view, the lowest point of the deflection within the second region 3606-2 of the target tissue surface is a vertical distance $X_{t2}$ from adjacent undisturbed regions of the target tissue surface. FIG. 37C shows a corresponding third cross-sectional view of a contour of the TUI surface 3706 in which a pin in a first region 3706-2 of the TUI surface 3706 is retracted by a first amount $X_{UT2}$ in response to the instrument deforming the second region 3606-2 of the target tissue surface by the amount $X_{t2}$. It can be seen that the first region of the target tissue surface 3606-1 has returned to its natural shape in response to removal of the instrument force from it. Also, in response to the first tissue region returning to its natural shape, the first region of the TUI surface 3706-1 reverts to its pre-force at rest shape. A deformation formed at a second region 3706-2 of the TUI surface that corresponds to the second region 3606-2 of the tissue surface has a shape that is corresponds to shape of the deformation of the second region of the tissue surface. The depth of deformation $X_{UT2}$ at the second region of the TUI surface is a function of at least the depth of deformation $X_{t2}$ of the target tissue surface in response to a force applied to the target tissue surface within the second region of the target tissue surface. Alternatively, according to principles, techniques, elements and steps presented above, the depth of deformation $X_{UT2}$ at the second region of the TUI surface may be a function of at least the corresponding force or stiffness values, $F_{t2}$ or $K_{t2}$.

In the illustrative example, due to the existence of the subsurface anomaly 3612, stiffness in the second region 3606-2 of the tissue structure 3602 is higher than stiffness in the first region 3606-1 of the target tissue structure 3602 due to the subsurface anomaly. In other words, the stiffer subsurface anomaly has a stiffening effect on the second region 3606-2 of the target tissue structure. As a result, the depth of deformation $X_{t1}$ of the target tissue surface in the first region 3606-1 is greater than the depth of deformation $X_{t2}$ of the target tissue surface 2606-2 in the second region. Moreover, the corresponding depth of deformation $X_{UT1}$ at the first region 3706-1 of the TUI feedback surface, which is a function of the depth of deformation $X_{t1}$ of the target tissue surface in the first region 3606-1, is greater than the depth of deformation $X_{UT2}$ at the second region 3706-2 of the TUI feedback surface, which is a function of the depth of deformation $X_{t2}$ of the tissue surface in the second region 3606-2. However, if instead of depth of deformation, the TUI changes its shape according to local tissue stiffness $K_{t2}$, and then the amount of deformation $X_{UT2}$ is larger than $X_{UT1}$ so as to reflect the increased tissue stiffness caused by the presence of the anomaly. Similarly, if the instrument force is mapped onto the TUI 2702, the deformation amount $X_{UT2}$ may be larger or smaller than $X_{UT1}$ according to the change in force to $F_{t2}$ from $F_{t1}$.

Figure 37D:
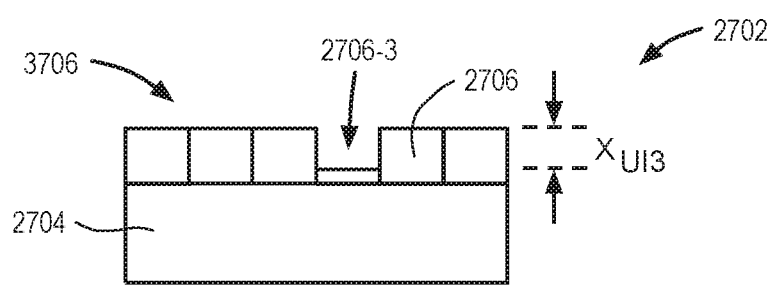

FIG. 36D shows a fourth cross-sectional view of the tissue structure 3602 in which an instrument 3604 is pressed against a third region 3606-3 of the tissue surface 3608. In the example fourth cross-sectional view, the lowest point of the deflection within the third region 3606-3 is a vertical distance $X_{t3}$ from adjacent undisturbed regions of the target tissue surface 3608. FIG. 37D shows a corresponding fourth cross-sectional view of a contour of the TUI feedback surface 3706 produced in response to the instrument deforming the third region 3606-3 of the tissue structure by the amount $X_{t3}$. A deformation formed at a third region 3706-3 of the TUI feedback surface 3706 that corresponds to the third region 3606-3 of the tissue surface 3608 has a shape that is corresponds to shape of the deformation of the third region 3606-3 of the tissue surface. Furthermore, the second region 3606-2 of the target tissue surface has returned to its natural shape in response to removal of the instrument force from it. Also, in response to the second target tissue region returning to its natural shape, the second region 3706-2 of the TUI feedback surface 3706 reverts to its pre-force at rest shape. Since the stiffness of the target tissue structure is substantially the same in both the first and third regions of the target tissue surface, the depth of deformation $X_{t1}$ is substantially the same as the depth of deformation $X_{UT3}$. Furthermore, since the depth of deformation $X_{UT1}$ is a function of the depth of deformation $X_{t1}$ and the depth of deformation $X_{UT3}$ is a function of the depth of deformation $X_{t3}$, the depth of deformation $X_{UT1}$ is substantially the same as the depth of deformation $X_{UT3}$.

Figure 37E:
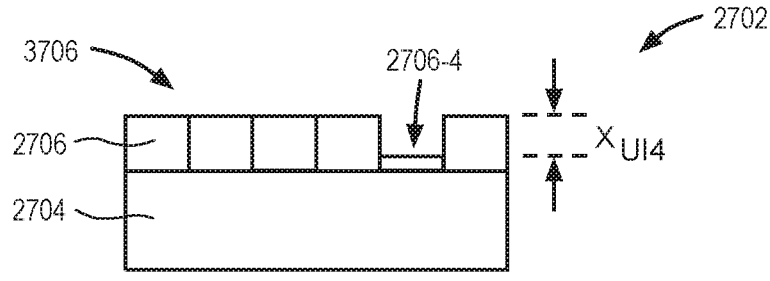
Figure 38A:
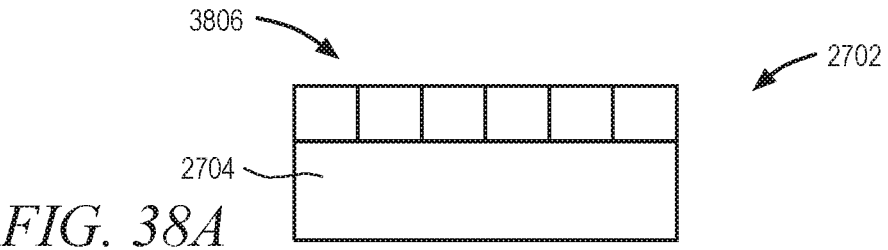
FIGS. 38A-38E are illustrative drawings showing a sequence of cross-section views of the TUI of FIGS. 27A-27C that show example "composite" deformations of the TUI feedback surface that correspond to example target tissue deformations shown the sequence of cross-section views of FIGS. 36A-36E in accordance with some embodiments.
Figure 38B:
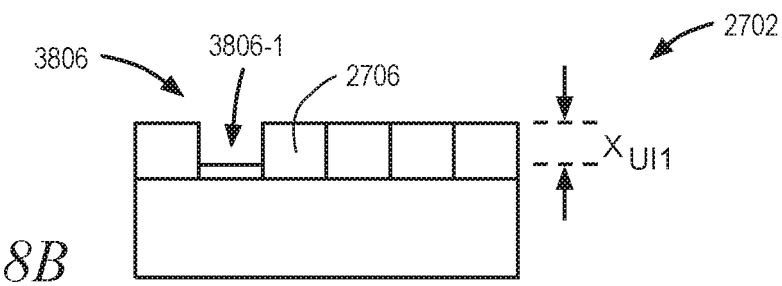
Figure 38C:
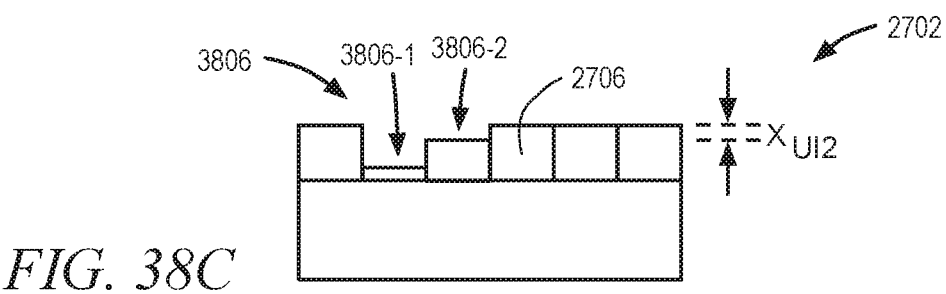
Figure 38D:
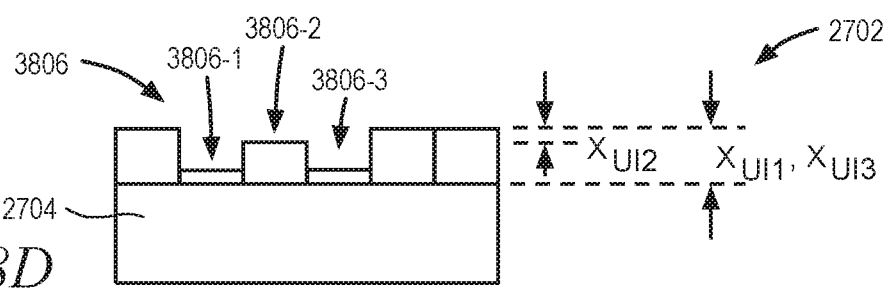
Figure 38E:
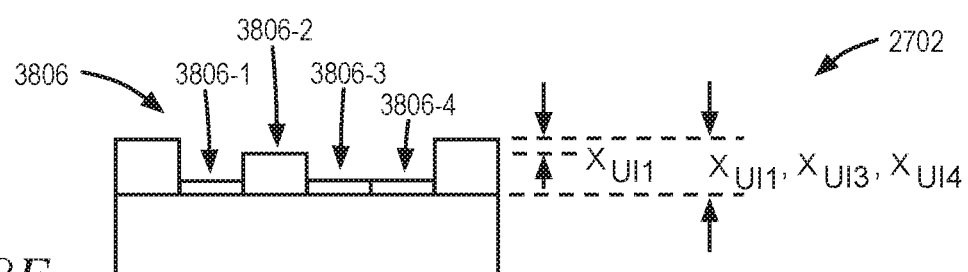

FIG. 36E shows a fourth cross-section view of the target tissue structure 3602 in which an instrument 3604 is pressed against a fourth region 3606-4 of the tissue surface 3608. In the example fourth cross-section view, the lowest point of the deflection within the fourth region 3606-4 is a vertical distance $X_{t4}$ from adjacent undisturbed regions of the target tissue surface 3608. FIG. 37E shows a corresponding fourth cross-section view of a contour of the TUI feedback surface 3706 produced in response to the instrument deforming the fourth region 3606-4 of the target tissue surface 3608 by the amount $X_{t4}$. The third region 3606-3 of the target tissue surface has returned to its natural shape in response to removal of the instrument force from it. Also, in response to the third target tissue region 3606-3 returning to its natural shape, the third region 3706-3 of the TUI feedback surface reverts to its pre-force at rest shape. A deformation formed at a fourth region 3706-4 of the TUI surface that corresponds to the fourth region 3606-4 of the tissue surface 3608 has a shape that is corresponds to the shape of the deformation of the fourth region 3606-4 of the tissue structure 3602. The depth of deformation $X_{UT4}$ at the fourth region 3706-4 of the TUI feedback surface 3706 is a function of at least the depth of deformation $X_{t4}$ of the target tissue surface in response to a force applied to the target tissue surface within the fourth region of the target tissue surface. In the example cross-sectional views of the target tissue surface, the target tissue deformations $X_{t1}$, $X_{t3}$, and $X_{t4}$ are substantially the same, and the example TUI surface deformations $X_{UT1}$, $X_{UT3}$, and $X_{UT4}$ are substantially the same.

It will be appreciated that although the instrument 3604 is shown to cause deformation at a sequence of discreet locations on the tissue surface 3608, a user may cause the instrument to move laterally across the tissue surface in a smooth motion so as to cause a deformation front to move across the target tissue surface. In that case, the discreet locations shown in FIGS. 36A-36E represent discrete locations on that deformation front. Alternatively, a user may cause the instrument to move in discrete hops from one location to the next. Alternatively, system 152 may automatically move the instruments to various locations under direct or indirect user control. Indirect user control refers to movement of instruments by via control by programmed commands in response to user initiation. Similarly, system 152 can be implemented to fully automate the movement of instruments according to algorithms defined inprogrammed commands. In the course of moving the instrument across the target tissue surface, in either a sequence of discrete motions or in a smooth motion, the user can touch the TUI feedback 3706 surface to feel its contour and get a physical sense of changes in shape and stiffness of the target tissue surface in response to the application of the instrument force to different target tissue locations. Since the amount of target tissue deformation is a function, at least in part, of target tissue stiffness as the point where the instrument force is applied, the amount of deformation of region of the TUI surface provides an indication of the stiffness of a corresponding region of the target tissue surface. In particular, for example, a user may sense the difference in deformation between $X_{UT2}$ at the second TUI location on the one hand and deformations $X_{UT1}$, $X_{UT3}$, and $X_{UT4}$ at the first, third, and fourth TUI locations on the other, Which may indicate to the user that the target tissue stiffness at the second target tissue location is different from the target tissue stiffness at the first, third, and fourth target tissue locations. As illustrated in FIGS. 36A-36E, this stiffness difference may be indicative of the presence of an unseen subsurface anomaly. Therefore, this virtual tissue palpation system and method offer haptic feedback about tissue deformation, force exerted by the instrument, or local tissue stiffness.

FIGS. 38A-38E are illustrative drawings showing a sequence of cross-sectional views of the TUI of FIGS. 27A-27C that show example "composite" deformations of the TUI feedback surface 3806 that correspond to example target tissue deformations shown the sequence of cross-section views of FIGS. 36A-36E in accordance with some embodiments. The TUI feedback surface deformations in FIGS. 38A-38E are referred to as "composite" to connote the notion that they accumulate. Each TUI surface deformation persists while others are created so that at the end of a sequence of discrete target tissue deformations or at the end of the occurrence of a deformation front, the accumulated TUI surface deformations provide a composite TUI surface deformation that includes all of the individual TUI surface deformations. Following the sequence of target surface deformations of FIGS. 36B-36E, for example, user can touch the contour of the TUI feedback surface 3806 to get a physical sense of differences in changes in shape of the target tissue surface 3608 at different discreet locations in response to the application of the instrument force to different target tissue locations. Differences in shape or depth of deformation at different locations of the TUI surface may be indicative of differences in target tissue surface stiffness of at corresponding target tissue locations, or of the force exerted by the instrument at the respective tissue location. For example, it can be seen that a first TUI surface location 3806-1, a third TUI surface location 3806-3, and a fourth. TUI surface location 3806-4 are respectively recessed by amounts $X_{UT1}$, $X_{UT3}$, and $X_{UT4}$ relative to the at rest level of the TUI surface, and that a second TUI surface location 3806-2 is recessed by a different amount $X_{UT2}$ relative to the at rest surface at rest level of the TUI. Assuming that substantially the instrument applies substantially the same force for all tissue deformations, since in the illustrative example, the amounts $X_{UT1}$, $X_{UT3}$, and $X_{UT4}$ are substantially the same, the difference between those amounts and the amount $X_{UT2}$ is due to a difference in stiffness of the target tissue surface in the second region 3606-2, which may be indicative of the hidden subsurface anomaly 3612.

Figure 39A:
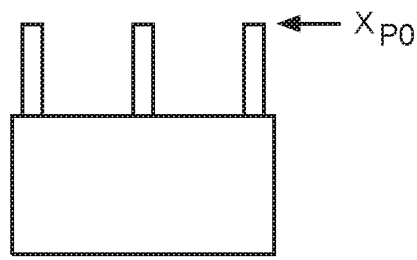
FIGS. 39A-39E are illustrative drawings showing a sequence of displacements of one or more pins within the alternative embodiment TUI of FIGS. 29A-29C in response to the example deformations of the target tissue surface shown in FIGS. 36A-36E, in accordance with some embodiments.
Figure 39B:
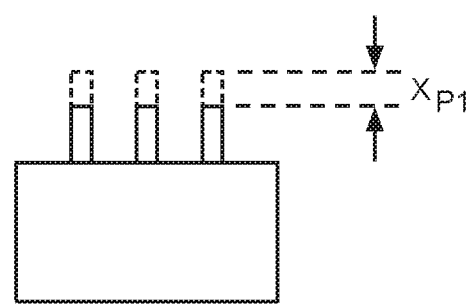
Figure 39C:
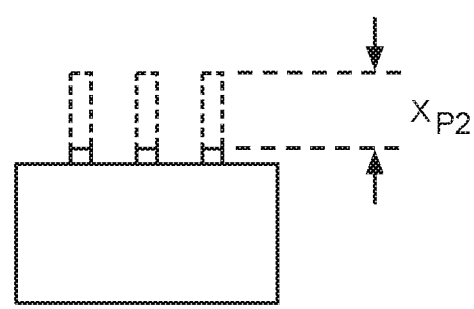
Figure 39D:
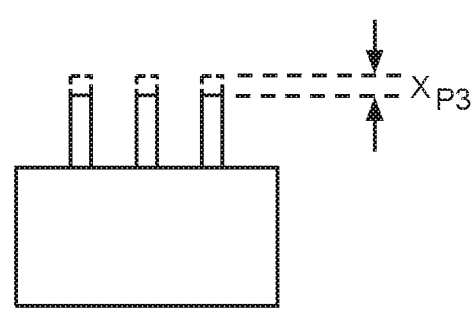
Figure 39E:
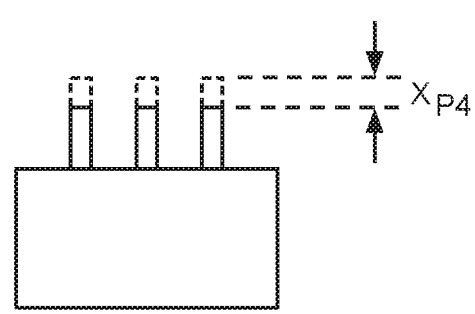

FIGS. 39A-39E are illustrative drawings showing a sequence of displacements of one or more pins 2906 within the alternative embodiment TUI 2902 of FIGS. 29A-29C in response to the example deformations of the target tissue surface shown in FIGS. 36A-36E, in accordance with some embodiments. The TUI 2902 provides a haptic interface includes an array of pins 2906, one or more of which, that can be selectively axially extended to provide an indication of stiffness of a tissue surface. In the illustrative example, the length of pin extension is proportional to stiffness: a longer pin extension corresponds to larger stiffness. Alternatively, an axial driving force may be increased to indicate to correspond to larger stiffness, as described above. As explained above, different regions of the tissue surface may have different stiffness, and the different stiffness of different regions may be indicative of the presence of hidden subsurface anomalies. The example initial pin displacement shown in FIG. 39A represents an at rest or quiescent initial pin displacement by an amount $X_{p0}$ that corresponds to the example target tissue surface prior to contact by the instrument represented in FIG. 36A. FIG. 39B represents a first pin displacement by an amount $X_{p1}$ in response to the example deformation by the amount $X_{t1}$ at the first location 3606-1 on the tissue surface represented in FIG. 36B. FIG. 39C represents a second pin displacement by an amount $X_{p2}$ in response to the example deformation by the amount $X_{t2}$ at the second location 3606-2 on the tissue surface represented in FIG. 36C. FIG. 39D represents a third pin displacement by an amount $X_{p3}$ in response to the example deformation by the amount $X_{t3}$ at the third location 3606-3 on the tissue surface represented in FIG. 39D. FIG. 36E represents a fourth pin displacement by an amount $X_{p4}$ in response to the example deformation by the amount $X_{t4}$ at the fourth location 3606-4 on the target tissue surface represented in FIG. 39E.

The first, third, and fourth pin displacements $X_{p1}$, $X_{p3}$ and $X_{p4}$ are substantially identical since the target tissue surface stiffness is the same at the first, third and fourth tissue surface locations. The second pin displacement $X_{p2}$ is greater than the other three since the tissue surface stiffness is greater at the second tissue location 3606-2. Thus, pin displacement provides an indication of target tissue surface stiffness as a user controllably moves the instrument through the sequence of contact locations on the target tissue surface represented by FIGS. 36A-36E, whether through discreet movements of the instrument from on location to the next or through a more continuous movement of the instrument. Moreover, a change in pin displacement as the instrument moves from one location to another indicates a change in target tissue structure stiffness as between the two locations. Alternatively, if instrument force f or tissue stiffness K are mapped onto the TUI, displacements $X_{p1-4}$ have values that depend on f and K and are computed according to steps discussed above. Therefore, this virtual tissue palpation system and method offer haptic feedback about tissue deformation, force exerted by the instrument or local tissue stiffness.

Those of skill in the art know how to substitute the use of TUI haptic feedback systems discussed above with other forms of haptic feedback interfaces. For example, if sub-threshold electrotactile stimulation is used as a form of haptic feedback then the magnitude of the stimulating current is modulated according to the steps discussed in above. Instead of modulating displacement $X_{UTi}$ or $X_{pi}$, the amplitude of the stimulating currents is changed accordingly. Alternatively, if vibrations of control input devices 160 are used as haptic feedback, the acceleration of the vibration, or the vibration intensity may be modulated as a function of tissue displacement $X_t$, force $F_t$ or stiffness $K_t$. Moreover, if visual interfaces are used to provide haptic feedback the visual element providing the feedback (e.g., visual indicia, bar graphs, digital displays, etc.) is modified according to the steps discussed above.

In operation, a user visually observes a surgical scene as the instrument is moved across the target tissue surface, either discretely or in a continuous movement, and is impressed downward with a small vertical force (relative to the target tissue surface) that is sufficient to deform the target tissue structure by a clinically safe amount, in a range of a fraction of a millimeter, to a few millimeters or up to a few centimeters, depending on the procedure and tissue type, for example, that is sufficiently large to trigger a reaction force that provides an indication of tissue structure stiffness but not large enough to cause tissue damage. For example, forces in the range of 5-40 g may be used during cardiac procedures. A smaller force range, 1-30 g, may be used during interventions on lungs. Procedures performed on stiffer structures, such as bones, may use higher levels of force, exceeding 100 g in certain cases. As the instrument is moved across the target tissue surface, the haptic interface provides a real-time indication (no user-perceivable delay) of target tissue structure deformation, stiffness, or force applied by the instrument. Thus, the user visually follows current location on the target tissue surface at which the instrument imparts its force to the target, and in real time, contemporaneously with the instrument providing a force to a given target tissue surface location.

As explained above with reference to FIG. 35, in accordance with some embodiments, the Q3D endoscopic system 101C, measures tissue displacement and then computes or approximates the amount of force imparted to the target tissue surface. In operation, during a stiffness determination, such as during a virtual palpation procedure, the force applied to the target tissue surface is maintained within a safe range described above. More particularly, in accordance with some embodiments, if substantially the same force is applied to each of the example discreet locations on the target tissue surface represented in FIGS. 36B-36E, then the tissue deflection represented by the haptic feedback interface information inversely proportional to the local tissue stiffness. In some embodiments, the user controls contact between the instrument and the target tissue structure so as to adjust force imposed by the instrument upon the target tissue structure. Thus, the force sensor can be used to achieve a substantially constant, normalized, force upon the target tissue structure throughout all of the stiffness determinations. Alternatively, force can be controlled automatically or semi-automatically by system 152. System 152 may also provide alerts to the surgeon or to surgical staff according to levels of instrument force determined from Q3D displacement measurements. For example, in FIG. 35, if the force exerted by the instrument exceeds a certain safety threshold, in addition to providing the appropriate visual index, system 152 may also sound an audible alarm or provide visual or tactile alerts.

The foregoing description and drawings of embodiments are merely illustrative of the principles of the invention. Various modifications can be made to the embodiments by those skilled in the art without departing from the spirit and scope of the invention, which is defined in the appended claims.

What is claimed is:

1. A method to provide haptic feedback during a medical procedure comprising:
    moving a surgical instrument across a surface of a tissue structure to impart a force to deform different tissue surface locations of the tissue structure;
    capturing image information, which includes the surface of the tissue structure and the surgical instrument imparting the force to the tissue structure, indicative of deformation distances at the different tissue surface locations of the tissue structure;
    producing in a non-transitory memory device a quantitative three dimensional (Q3D) model that provides a map of measures of tissue structure deformation for the contact between the surgical instrument and the tissue surface at the different locations of the tissue structure, based upon the captured image information; and
    producing haptic feedback indicative of the map of the measures of tissue structure deformation at the contact locations of the surface of the tissue structure.

2. The method of claim 1,
    wherein capturing the image information includes positioning a Q3D endoscope, having an imaging sensor array comprising at least three coplanar imaging sensors having coplanar overlapping fields of view, to capture the different tissue surface locations of the tissue structure within the overlapping fields of view.

3. The method of claim 1;
    wherein producing the haptic feedback includes producing a shape display indicative of the map of the measures of tissue structure deformation at the contact locations of the surface of the tissue structure.

4. The method of claim 1;
    wherein producing the haptic feedback includes providing a three-dimensional contour that models at least a portion of the tissue structure.

5. The method of claim 1,
    wherein producing the haptic feedback includes displacing one or more pins of a tangible user interface.

6. The method of claim 1 further including:
    producing an alarm in response to a measure of tissue structure deformation that is outside of a clinically safe range.

7. The method of claim 6,
    wherein the alarm includes an audible alarm.

8. The method of claim 6,
    wherein the alarm includes a visual alarm.

9. The method of claim 1 further including:
measuring a force imparted to the tissue structure during deformation of the tissue structure via a force sensor; and
providing a visual indication of force measured by the force sensor.

10. A method for determining force exerted onto tissue during a medical procedure comprising:
moving a surgical instrument across a surface of a tissue structure to impart a force to deform different tissue surface locations of the tissue structure;
capturing image information, which includes the surface of the tissue structure and the surgical instrument imparting the force to the tissue structure, indicative of deformation distances at the different tissue surface locations of the tissue structure;
producing in a non-transitory memory device a quantitative three-dimensional (Q3D) model that provides a map of measures of tissue structure deformation for the contact between the surgical instrument and the tissue surface at the different locations of the tissue structure, based upon the captured image information; and
determining a force exerted by the surgical instrument onto said tissue structure at at least one measured location of tissue structure deformation based upon, at least in part, a measure of tissue deformation at the at least one measured location of tissue structure deformation.

11. The method of claim 10,
wherein capturing the image information includes positioning a Q3D endoscope, having an imaging sensor array comprising at least three coplanar imaging sensors having coplanar overlapping fields of view, to capture the different tissue surface locations of the tissue structure within the overlapping fields of view.

12. The method of claim 10 further including:
producing an alarm in response to a determined force that is outside of a clinically safe range.

13. The method of claim 12 further including:
wherein the alarm includes an audible alarm.

14. The method of claim 12 further including:
wherein the alarm includes a visual alarm.

15. A method for providing virtual tissue palpation during medical procedures comprising:
moving a surgical instrument across a surface of a tissue structure to impart a force to deform different tissue surface locations of the tissue structure;
capturing image information, which includes the surface of the tissue structure and the surgical instrument imparting the force to the tissue structure, indicative of deformation distances at the different tissue surface locations of the tissue structure;
producing in a non-transitory memory device a quantitative three-dimensional (Q3D) model that provides a map of measures of tissue structure deformation for the contact between the surgical instrument and the tissue surface at the different locations of the tissue structure, based upon the captured image information; and
determining tissue stiffness at at least one measured location of tissue structure deformation based upon, at least in part, a measure of tissue deformation at the at least one measured location of tissue structure deformation
producing haptic feedback indicative of the determined tissue stiffness at the at least one measured location of tissue structure deformation.

16. The method of claim 15,
wherein capturing the image includes positioning a Q3D endoscope, having an imaging sensor array comprising at least three coplanar imaging sensors having coplanar overlapping fields of view, to capture the different tissue surface locations of the tissue structure within the overlapping fields of view.

17. The method of claim 15,
wherein moving the surgical instrument includes automatically moving the surgical instrument to a series of locations across the tissue surface.

18. The method of claim 15 further including:
producing an alarm in response to a determined stiffness outside a clinically safe range.

19. The method of claim 18,
wherein the alarm includes an audible alarm.

20. The method of claim 18,
wherein the alarm includes a visual alarm.

* * * * *

UNITED STATES PATENT AND TRADEMARK OFFICE
CERTIFICATE OF CORRECTION

PATENT NO. : 11,304,771 B2
APPLICATION NO. : 16/570917
DATED : April 19, 2022
INVENTOR(S) : Panescu et al.

It is certified that error appears in the above-identified patent and that said Letters Patent is hereby corrected as shown below:

On the Title Page

On page 2, in Column 2, Item (56) under "U.S. Patent Documents", Line 32, delete "2009/0157659" and insert --2009/0157059-- therefor On page 2, in Column 2, Item (56) under "U.S. Patent Documents", Line 49, delete "2010/0312696" and insert --2010/0312096-- therefor On page 3, in Column 2, Item (56) under "Other Publications", Line 29, delete "Culnat" and insert --Culjat-- therefor On page 4, in Column 1, Item (56) under "Other Publications", Line 4, delete ""Tactite" and insert --"Tactile-- therefor On page 4, in Column 1, Item (56) under "Other Publications", Line 8, delete "Aoplication" and insert --Application-- therefor On page 4, in Column 1, Item (56) under "Other Publications", Lines 10-11, delete "EP1 5767964.8," and insert --EP15767964.8,-- therefor On page 4, in Column 1, Item (56) under "Other Publications", Lines 16-17, delete "EP16770100.4," and insert --EP15770100.4,-- therefor On page 4, in Column 1, Item (56) under "Other Publications", Lines 18-19, delete "EP16770259.8," and insert --EP15770259.8,-- therefor On page 4, in Column 1, Item (56) under "Other Publications", Line 33, delete "2814]." and insert --2014].-- therefor Signed and Sealed this
Thirty-first Day of May, 2022

*Katherine Kelly Vidal*
Katherine Kelly Vidal
*Director of the United States Patent and Trademark Office*

CERTIFICATE OF CORRECTION (continued)
U.S. Pat. No. 11,304,771 B2

On page 4, in Column 1, Item (56) under "Other Publications", Line 39, delete "PCT/US16/23210," and insert --PCT/US15/23210,-- therefor On page 4, in Column 2, Item (56) under "Other Publications", Line 6, delete "Surqery" and insert --Surgery-- therefor On page 4, in Column 2, Item (56) under "Other Publications", Line 38, delete ""Shape-Ghanging" and insert --"Shape-Changing-- therefor In the Claims In Column 40, Line 48, in Claim 3, delete "claim 1;" and insert --claim 1,-- therefor In Column 40, Line 53, in Claim 4, delete "claim 1;" and insert --claim 1,-- therefor In Column 42, Line 17, in Claim 15, after "information;", delete "and"

In Column 42, Lines 21-22, in Claim 15, delete "deformation" and insert --deformation; and-- therefor